US006821978B2

(12) United States Patent
Chackalamannil et al.

(10) Patent No.: US 6,821,978 B2
(45) Date of Patent: Nov. 23, 2004

(54) XANTHINE PHOSPHODIESTERASE V INHIBITORS

(75) Inventors: Samuel Chackalamannil, East Brunswick, NJ (US); Yuguang Wang, North Brunswick, NJ (US); Craig D. Boyle, Branchburg, NJ (US); Andrew W. Stamford, Chatham Township, NJ (US)

(73) Assignee: Schering Corporation, Kenilworth, NJ (US)

(*) Notice: Subject to any disclaimer, the term of this patent is extended or adjusted under 35 U.S.C. 154(b) by 248 days.

(21) Appl. No.: 09/940,760

(22) Filed: Aug. 28, 2001

(65) Prior Publication Data

US 2002/0169174 A1 Nov. 14, 2002

Related U.S. Application Data

(60) Provisional application No. 60/233,567, filed on Sep. 19, 2000.

(51) Int. Cl.[7] ...................... A61K 31/505; A61K 31/52; C07D 473/00
(52) U.S. Cl. ................ 514/262.1; 514/257; 514/263.1; 514/263.34; 514/213.37; 544/262; 544/245; 544/264; 544/267
(58) Field of Search .................. 514/257, 263.1, 514/262.1, 263.34, 263.37; 544/262, 245, 264, 267

(56) References Cited

U.S. PATENT DOCUMENTS

| | | | |
|---|---|---|---|
| 5,250,534 A | 10/1993 | Bell et al. | 514/258 |
| 5,256,766 A | 10/1993 | Coughlin | 530/327 |
| 5,321,029 A | 6/1994 | Maschler et al. | 514/263 |
| 5,346,901 A | 9/1994 | Bell et al. | 514/258 |
| 5,393,755 A | 2/1995 | Neustadt et al. | 514/233.2 |
| 5,409,934 A | 4/1995 | Smith et al. | 514/263 |
| 5,470,579 A | 11/1995 | Bonte et al. | 424/450 |
| 5,637,593 A | 6/1997 | Porter et al. | 514/274 |
| 5,688,768 A | 11/1997 | Coughlin et al. | 514/15 |
| 5,719,283 A | 2/1998 | Bell et al. | 544/262 |
| 5,759,994 A | 6/1998 | Coughlin et al. | 514/9 |
| 5,798,248 A | 8/1998 | Coughlin et al. | 435/214 |
| 5,824,683 A | 10/1998 | McKittrick et al. | 514/257 |
| 5,856,448 A | 1/1999 | Coughlin | 530/388.22 |
| 5,859,006 A | 1/1999 | Daugan | 514/249 |
| 5,874,437 A | 2/1999 | Garvey et al. | 514/258 |
| 5,877,216 A | 3/1999 | Place et al. | 514/573 |
| 5,939,419 A | 8/1999 | Tulshian et al. | 514/257 |
| 5,955,611 A | 9/1999 | Dunn et al. | 544/262 |
| 5,958,926 A | 9/1999 | Garvey et al. | 514/253 |
| 5,981,527 A | 11/1999 | Daugan et al. | 514/250 |
| 5,981,563 A | 11/1999 | Lowrey | 514/400 |
| 6,023,640 A | 2/2000 | Ross | 607/2 |
| 6,024,936 A | 2/2000 | Coughlin et al. | 424/1.49 |
| 6,025,494 A | 2/2000 | Daugan | 546/64 |
| 6,037,346 A | 3/2000 | Doherty, Jr. et al. | 514/258 |
| 6,051,594 A | 4/2000 | Lowrey | 514/400 |
| 6,066,735 A | 5/2000 | Dunn et al. | 544/262 |
| 6,087,362 A | 7/2000 | El-Rashidy | 514/253 |
| 6,100,270 A | 8/2000 | Campbell | 514/258 |
| 6,124,101 A | 9/2000 | Coughlin | 435/7.1 |
| 6,140,329 A | 10/2000 | Daugan | 514/250 |
| 6,143,746 A | 11/2000 | Daugan et al. | 514/249 |
| 6,197,541 B1 | 3/2001 | Coughlin | 435/69.1 |
| 6,362,178 B1 | 3/2002 | Niewöhner et al. | 514/218 |
| 6,403,597 B1 | 6/2002 | Wilson et al. | 514/256 |
| 6,469,012 B1 | 10/2002 | Ellis et al. | 514/258 |
| 6,469,016 B1 | 10/2002 | Place et al. | 514/262 |
| 6,472,434 B1 | 10/2002 | Place et al. | 514/573 |
| 6,512,002 B2 | 1/2003 | Lee et al. | 514/427 |

FOREIGN PATENT DOCUMENTS

| | | |
|---|---|---|
| DE | P 19 38 016.6 | 1/1971 |
| EP | 0 258 191 A1 | 3/1988 |

(List continued on next page.)

OTHER PUBLICATIONS

Kremzer et al,"Synth. & Biol. activity of diprophylline anal.",Khim.–Farm.Zh.,15/6,59–64(1981);CAS ABS '81:532818.*

(List continued on next page.)

*Primary Examiner*—Mukund J. Shah
*Assistant Examiner*—Sudhaker B. Patel
(74) *Attorney, Agent, or Firm*—Gerald E. Reinhardt; Palaiyur S. Kalyanaraman

(57) ABSTRACT

A xanthine phosphodiesterase V inhibitor having the formula (I), with the variables defined herein, which is especially useful for treating male (erectile) and female sexual dysfunction and other physiological disorders:

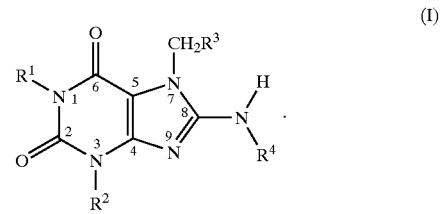

(I)

For example, a representative compound of the invention is:

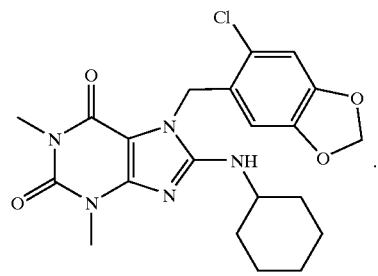

34 Claims, No Drawings

FOREIGN PATENT DOCUMENTS

| | | |
|---|---|---|
| EP | 0 389 282 A3 | 9/1990 |
| EP | 0 389 282 B1 | 9/1990 |
| EP | 389282 * | 9/1990 |
| EP | 0389 282 A2 | 9/1990 |
| EP | 0 389 282 A2 | 9/1990 |
| EP | 0 463 756 B1 | 1/1992 |
| EP | 0 463 756 A1 | 1/1992 |
| EP | 0 526 004 A1 | 2/1993 |
| EP | 0 702 555 B1 | 3/1996 |
| FR | 2.116.302 | 7/1972 |
| FR | 2 116 302 A | 7/1972 |
| WO | 89/10123 | 11/1989 |
| WO | WO 91/07945 | 6/1991 |
| WO | WO 91/07945 A1 | 6/1991 |
| WO | 91/19717 | 12/1991 |
| WO | WO91/19717 | 12/1991 |
| WO | 92/05175 | 4/1992 |
| WO | WO 92/05175 | 4/1992 |
| WO | 92/05176 | 4/1992 |
| WO | WO 92/05176 | 4/1992 |
| WO | WO92/05176 | 4/1992 |
| WO | WO 92/11260 | 7/1992 |
| WO | 9211260 * | 7/1992 |
| WO | 93/23401 | 11/1993 |
| WO | WO 93/23401 | 11/1993 |
| WO | 94/19351 | 9/1994 |
| WO | WO 94/28902 | 12/1994 |
| WO | 96/16644 | 6/1996 |
| WO | 96/16657 | 6/1996 |
| WO | 96/32379 | 10/1996 |
| WO | 97/03985 | 2/1997 |
| WO | 97/24334 | 7/1997 |
| WO | 97/43287 | 11/1997 |
| WO | 98/08848 | 3/1998 |
| WO | 98/15530 | 4/1998 |
| WO | 98/38168 | 9/1998 |
| WO | 98/49166 | 11/1998 |
| WO | 99/00359 | 1/1999 |
| WO | 99/00373 | 1/1999 |
| WO | 99/21558 | 5/1999 |
| WO | 99/21831 | 5/1999 |
| WO | WO 99/24433 | 5/1999 |
| WO | 99/42452 | 8/1999 |
| WO | 99/43674 | 9/1999 |
| WO | 99/43679 | 9/1999 |
| WO | WO 99/54331 A | 10/1999 |
| WO | WO 99/54331 | 10/1999 |
| WO | 99/54333 | 10/1999 |
| WO | WO 99/62905 | 12/1999 |

OTHER PUBLICATIONS

PCT International Search Report for PCT US 01/28983 mailed Feb. 15, 2002.

Murray, K.J., Phosphodiesterase $V_A$ Inhibitors, *DN&P* 6(3), pp. 150–155, Apr. 1993.

Youssef, S. et al., Purines XIV. [1] Reactivity of 8–Bromo–3–9–dimethylxanthine Towards Some Nucleophilic Reagents, J. Heterocyclic hem., 35, 949 (1998).

Nantka–Namirski, P. et al., *Synteza 7–Podstawionych Pochodnych 8–aminometylo–1,3–Dwumetloksantyny,* Acia Polan, Pharm. XXX1 Nr 1, (1974) [in Polish].

Nantka–Namirski, P. et al., *Synthesis of 7–Subtituted Deviates of 8–aminomethyl–1,3–dimethylxanthine,* Acta.Polon, Pharma. 31(1):5–11 (1974) [English translation].

Yoneda, F. et al., A New Synthesis of Substituted 8–Aminopurine Derivatives, Bulletin of the Chemical Society of Japan, vol. 46, pp. 1836–1839 (1973).

T. Katsushima et al., *Structure–Activity Relationships of 8–Cycloalkl–1,3–diprophylxanthines as Antagonists of Adenosine Receptors,* J. Med. Chem. 1990, 33, pp. 1906–1910.

XP–002188426, *Synthesis and biological activity of 3–methyl, 7– or 8–alkyl–, 7,8–dialkyl, heterocyclic, and cyclohexylaminoxanthines,* 6001 Chemical Abstracts, Columbus, Ohio, US, No. 106:95577n, (1987).

Dukarm R.C., et al., (1999) The cGMP–specific Phosphodiesterase Inhibitor E4021 Dilates the Pulmonary Circulation. *American Journal Respir. Crit. Care Med.,* vol. 160:858–865.

Gaine S.P., et al., (1998) Primary Pulmonary Hypertension. *The Lancet,* vol. 352:719–725.

Hanasato N., et al., (1999) E–4010, a Selective Phosphodiesterase 5 Inhibitor, Attenuates Hypoxic Pulmonary Hypertension in Rats. American Journal of Physiol., vol. 277 (Lung Cell. Mol. Physiol. 21): L225–L232.

Ohnishi M., et al., (1999) E4021, a Selective Phosphodiesterase 5 Inhibitor, Potentiates the Vasodilator Effect of Inhaled Nitric Oxide in Isolated Perfused Rat Lungs. *Journal of Cardiovascular Pharmacology,* vol. 33:619–624.

Ho–Sam Ahn et al., "Potent Tetracyclic Guanine Inhibitors of PDE1 and PDE5 Cyclic Guanosine Monophosphate Phosphodiesterases with Oral Antihypertensive Activity", *J. Med. Chem.* , vol. 40, No. 14, pp. 2196–2210 (1997).

J.L. Ambrus et al., "Studies on Vasoocclusive Crisis of Sickle Cell Disease. I. Effect of Pentoxifylline", *Journal of Medicine,* vol. 10, No. 6, pp. 445–456 (1979).

Bradley D. Anderson et al, "Preparation of Water–Soluble Compounds Through Salt Formation", The Practice of Medicinal Chemistry, C. G. Wermuth, Ed., *Academic Press,* New York, pp. 739–754 (1996).

M.I. Argel et al, "Effect of Phosphodiesterase Inhibitors on Heart Contractile Behavior, Protein Kinase Activity and Cyclic Nucleotide Levels", *J. Mol. Cell Cardiol,* vol. 12, No. 10, pp. 939–954, Abstract (1980).

Hans–Joachim Arnold et al, "Pharmacopoeia of Traditional Medicine in Venda", *Journal of Ethnopharmacology,* vol. 12, pp. 35–74 (1984).

William J. Aronson et al,"The Mediator of Human Corpus Cavernosum Relaxation is Nitric Oxide", *The Journal of Urology,* vol. 145, No. 4, p. 341A, Abstract No. 516 (1991).

Joseph A. Beavo, "Cyclic Nucleotide Phosphodiesterases: Functional Implications of Multiple Isoforms", *Physiological Reviews,* vol. 75, No. 5, pp. 725–748 (Oct. 1995).

Joseph A. Beavo & David H. Reifsnyder, "Primary sequence of cyclic nucleotide phosphodiesterase isozymes and the design of selective inhibitors", *Trends in Pharmacological Sciences,* vol. 11, No. 4, pp. 150–155 (Apr. 1990).

Stephen M. Berge et al, "Pharmaceutical Salts", J. of *Pharmaceutical Sciences,* Am. Pharm. Assoc. and Pergamon Press, vol. 66, No. 1, pp. 1–19 (Jan., 1977).

Anne Bowman et al, "Cyclic GMP mediates neurogenic relaxation in the bovine retractor penis muscle", *Br. J. Pharmac.,* vol. 81, pp. 665–674 (1984).

V. Mirone et al, letter to ed. re. "Intracavernous Cyclic GMP Products Produces Penile Erection in Patients with Erectile Dysfunction", *British Journal of Urology,* vol. 71, No. 3, p. 365 (Mar. 1993).

Gary Brooker et al, "Radioimmunoassay of Cyclic AMP and Cyclic GMP", *Advances in Cyclic Nucleotide Research,* Paul Greengard et al, Eds., vol. 10, pp. 1–33 (1979).

Margaret Ann Bush, "The role of the L–arginine–nitric oxide–cyclic GMP pathway in relaxation of corpus cavernosum smooth muscle", Ph.D. dissertation U.C.L.A. (UMI Dissertation Services Order No. 9319914) (179 pgs) (1993).

Peggy Bush et al, "Nitric Oxide is a Potent Relaxant of Human and Rabbit Corpus Cavernosum", *Journal of Urology*, vol. 147, pp. 1650–1655 (Jun. 1992).

S. Carrier et al, "Erectile Dysfunction," *Endocrinology and Metabolism Clinics of North America: Clinical Andrology*, vol. 23, No. 4, pp. 773–782 (Dec. 1994).

P. Cazzulani et al, "Pharmacological Activities of the Main Metabolite of Flavoxate 3–Methylflavone–8–carboxylic Acid", *Drug. Res.*, vol. 38 (1), No. 3, pp. 379–382 (1988).

J. Cortijo et al, "Investigation into the role of Phosphodiesterase IV in Bronchorelaxation, including Studies with Human Bronchus", *Br. J. Pharmacol.*, vol. 108, pp. 562–568 (1993).

Jacob de Boer et al, "Human bronchial cyclic nucleotide phosphodiesterase isoenzymes: biochemical and pharmacological analysis using selective inhibitors", *Br. J. Pharmacol.*, vol. 106, pp. 1028–1034 (1992).

Dario Doller et al, "The GIF System as a Tool in Medicinal Chemistry: The Oxidation of SCH57726 under GOAGG III Conditions", *Bioorganic and Medicinal Chemistry Letters*, vol. 7, No. 11, pp. 1381–1386 (1997).

I.J. Fishman, "Treating Erectile Dysfunction: New Approaches", *Drug Therapy*, vol. 8, pp. 102–110 (Aug. 1989).

P.G. Gillespie & J.A. Beavo, "Inhibition and Stimulation of Photoreceptor Phosphodiesterases by Dipyridamole and M & B 22, 948", *Molecular Pharmacology*, vol. 36, pp. 773–781 (Nov. 1988).

J.C. Gingell, et al, "Emerging pharmacological therapies for erectile dysfunction", *Exp. Opin. Ther. Patents*, vol. 9, No. 12, pp. 1689–1696 (1999).

Philip L. Gould, "Salt Selection for Basic Drugs", *Int'l J. of Pharmaceutics*, Elsevier, vol. 33, pp. 201–217 (1986).

Theodora W. Greene, "Protective Groups in Organic Synthesis", John Wiley & Sons, Inc., New York, pp. 1–9 (1981).

Alain Gregoire, "Viagra: on release", *BMJ*, vol. 317, pp. 759–760 (Sep. 19, 1998).

"Pharmaceutical Coloring Agents", Handbook of Pharmaceutical Excipients, American Pharmaceutical Association & the Pharmaceutical Society of Great Britain, pp. 81–90 (1986).

Takeru Higuchi, "Prodrug & Drug Delivery –An Overview", Bioreversible Carriers in Drug Design: Theory and Application, Edward B. Roche, Ed., Pergamon Press, New York, pp. 1–12 (1987).

T. Higuchi et al, Eds., "Pro–drugs as Novel Drug Delivery Systems", ACS Symposium Series 14, American Chemical Society, Wash., D.C., pp. 1–115 (1975).

F. Holmquist et al, "Actions of 3–Morpholinosydnonimin (SIN–1) on Rabbit Isolated Penile Erectile Tissue", *Journal of Urology*, vol. 150, No. 4, pp. 1310–1315 (Oct. 1993).

F. Holmquist et al, "Effects of the nitric oxide synthase inhibitor $N^G$–nitro–L–arginine on the erectile response to cavernous nerve stimulation in the rabbit", *Acta Physiol Scand*, vol. 143, pp. 299–304 (1991).

Sue Ellen Jackson et al, "Erectile Dysfunction: Therapy Health Outcomes", *Outcomes Research, Pfizer, Inc.*, Elsevier (Dec. 16, 1997).

Yasuo Kawanishi et al, "Double–Blind Trial of Oral Prostaglandin $E_1$ on Impotence", *The Japanese Urological Association*, vol. 83, No. 1, Abstract, pp. 1655–1661 (Oct. 1992).

Stanley G. Korenman et al, "Treatment of Vasculogenic Sexual Dysfunction with Pentoxifylline," *J. Am. Geriatrics Soc.*, vol. 41, No. 4, pp. 363–366 (Apr., 1993).

Robert J. Krane et al, "Impotence", *New England Journal of Medicine*, vol. 321, No. 24, pp. 1648–1658 (Dec. 14, 1989).

W.R. Kukovetz et al, "Evidence for Cyclic GMP–Mediated Relaxant Effects of Nitro–Compounds in Coronary Smooth Muscle", *Naunyn–Schmiedeberg's Archives of Pharmacology*, vol. 310, pp. 129–138 (1979).

Y.–M. Lin et al, "The rabbit as an intracavernous injection study model", *Urol. Res*, vol. 24, pp. 27–32 (1996).

Tom F. Lue, "Topical and Oral Agents for Erectile Dysfunction", *J. Formos Med. Assoc*, vol. 98, No. 4, pp. 233–241(Mar. 9, 1999).

James A. Lugg et al, "The Role of Nitric Oxide in Erectile Function," *J. of Andrology*, vol. 16, No. 1, pp. 2–4 (Jan./Feb. 1995).

E.G. McMahon et al, "Depressor and Natriuretic Effects of M & B 22, 948, a Guanosine Cyclic 3',5'–Monophosphate–Selective Phosphodiesterase Inhibitor", *Journal of Pharmacology and Experimental Therapeutics*, vol. 2513, pp. 1000–1005 (1989).

W. Meinhardt et al, "The influence of medication on erectile function", *International Journal of Impotence Research*, vol. 9, pp. 17–26 (1997).

M.F. Meyer et al, "Intracavernous Application of SIN–I in Rabbit and Man: Functional and Toxicological Results", *Ann. Urol.*, vol. 27, No. 3, pp. 179–182 (1993).

Alvaro Morales et al, "Oral and Topical Treatment of Erectile Dysfunction", *Urologic Clinics of North America*, vol. 22, No. 4, pp. 879–886 (Nov. 1995).

John E. Morley, "Management of Impotence, Diagnostic considerations and therapeutic options", *Impotence*, vol. 93, No. 3, pp. 65–67, 71–72 (Feb. 15, 1993).

C. David Nicholson et al, "Differential modulation of tissue function and therapeutic potential of selective inhibitors of cyclic nucleotide phosphodiesterase isoenzymes", *Trends in Pharmacological Sciences*, vol. 12, pp. 19–27 (Jan. 1991).

Elizabeth Palmer, "Making the love drug", *Chemistry in Britain*, vol. 35, No. 1, pp. 24–26 (Jan. 1999).

Pfizer, "Erectile Dysfunction", 1998 Annual Report, p. 21.

Physicians' Desk Reference, Medical Economics Company, $55^{th}$ Ed., pp. 2534–2537 (2001).

Physician's Desk Reference, Medical Economics Company, 46th Ed., pp. 1099–1100 (1992).

Physician's Desk Reference, Medical Economics Company, 46th Ed., Product Identification Dayton Himbin Tablets and Yohimex Tablets, pp. 409, 905 & 1190 (1992).

Jacob Rajfer et al, "Nitric Oxide as a Mediator of Relaxation of the Corpus Cavernosum in Response to Nonadrenergic, Noncholinergic Neurotransmission", *New England Journal of Medicine*, vol. 326, No. 2, pp. 90–94 (Jan. 9, 1992).

J. Reiser et al, "The Effect of Zaprinast (M&B 22, 948, an Orally Absorbed Mast Cell Stabilizer) on Exercise–Induced Asthma in Children", *Br. J. Dis. Chest.*, vol. 80, pp. 157–163 (1986).

Remington's Pharmaceutical Sciences, "Coloring, Flavoring and Diluting Agents", 18th Ed., A.R. Gennaro, Ed., Mack Publishing Co., pp. 1288–1300 (1990).

Remington's Pharmaceutical Sciences, 18th Ed., A.R. Gennaro, Ed., Mack Publishing Co., pp. 1519–1712 (1990).

Alan Riley, "Oral Treatments for Erectile Dysfunction", *International Journal of STD & AIDS*, vol. 7, Suppl 3, pp. 16–18 (1996).

N.I. Romanenko et al, "Synthesis and biological activity of 3–methyl, 7–or 8–alkyl–, 7,8–dialkyl, heterocyclic, and cyclohexylaminoxanthines", *Chemical Abstracts*, 106: 95577n (1986).

Raymond C. Rosen et al, "The process of care model for evaluation and treatment of erectile dysfunction", *International Journal of Impotence Research*, vol. 11, pp. 59–74 (1999).

David P. Rotella et al, "N–3–Substituted Imidazoquinazolinones: Potent and Selective PDE5 Inhibitors as Potential Agents for Treatment of Erectile Dysfunction", *J. Med. Chem*, vol. 43, No. 7, pp. 1257–1263 (2000).

Robin M. Rudd et al, "Inhibition of Exercise–Induced Asthma by an Orally Absorbed Mast Cell Stabilizer (M & B 22,948)", *Br. J. Dis. Chest*, vol. 77, pp. 78–84 (1983).

Richard Sachse et al, "Safety, Tolerability and Pharmacokinetics of Bay 38–9456 in Patients with Erectile Dysfunction", *Journal of Urology*, vol. 163, No. 4, p. 204 (May 2000).

T. Saeki & I. Saito, "Isolation of Cyclic Nucleotide Phosphodiesterase Isozymes from Pig Aorta", *Biochemistry Pharmacology*, vol. 46, No. 5, pp. 833–839 (1993).

Junichi Shimada et al, "A Convenient Synthesis of Tricyclic Purine Derivatives", *J. of Heterocyclic Chemistry*, vol. 30, pp. 241–246, (1993).

Christian G. Stief et al, "Preliminary Results with the Nitric Oxide Donor Linsidomine Chlorhydrate in the Treatment of Human Erectile Dysfunction", *The Journal of Urology*, vol. 148, No. 5, pp. 1437–1440 (Nov. 1992).

Christian G. Stief et al, "Preliminary report on the effect of the nitric oxide donor SIN–1 on human cavernous tissue in vivo", *World J. Urol*, vol. 9, pp. 237–239 (1991).

Christian G. Stief et al, "The Effect of the Specific Phosphodiesterase (PDE) Inhibitors on Human and Rabbit Cavernous Tissue *in Vitro* and *in Vivo*," *J. of Urology*, Am. Urological Assoc., vol. 159, pp. 1390–1393 (1998).

A. Taher et al, "Phosphodiesterase Activity in Human Cavernous Tissue and the Effect of Various Selective Inhibitors", *The Journal of Urology*, vol. 149, No. 4, p. 285 (Abstract) (Apr. 1993).

A. Taher et al, "Cyclic Nucleotide Phosphodiesterase Activity in Human Cavernous Smooth Muscle and the Effect of Various Selective Inhibitors", *Int. J. Impotence Res.*, vol. 4, Suppl. 2, p. 11 (1992).

Yoshlastu Takahashi et al, "Pharmacological Effects of Adenosine on Canine Penile Erection", *Tohoku J. Exp. Med.*, vol. 165, pp. 49–58 (1991).

Harvey C. Taub et al, "Relationship between Contraction and Relaxation in Human and Rabbit Corpus Cavernosum", *Urology*, vol. 42, No. 6, pp. 698–704 (Dec. 1993).

W. Joseph Thompson, "Cyclic Nucleotide Phosphodiesterases: Pharmacology, Biochemistry and Function", *Pharmac. Ther.*, vol. 51, pp. 13–33 (1991).

Flavio Trigo–Rocha et al, "The Role of Cyclic Adenosine Monophosphate, Cyclic Guanosine Monophosphate, Endothelium and Nonadrenergic, Noncholinergic Neurotransmission in Canine Penile Erection", *Journal of Urology*, vol. 149, No. 4, pp. 872–877 (Apr. 1993).

Flavio Trigo–Rocha et al, "Nitric oxide and cGMP: mediators of pelvic nerve–stimulated erection in dogs", *Am. J. Physiol.*, vol. 264, pp. H419–H422 (1993).

Flavio Trigo–Rocha et al, "Intracellular Mechanism of Penile Erection in Monkeys," *Neurology and Urodynamics*, vol. 13, pp. 71–80 (1994).

Flavio Trigo–Rocha et al, "The Effect of Intracavernous Injection of Potassium Channel Openers in Monkeys and Dogs," *Int. J. of Impotence Research*, Smith–Gordon, London, vol. 7, pp. 41–48 (1995).

Flavio Trigo–Rocha et al, "Sodium Nitroprusside: Physiologic Effects as a Nitric Oxide Donor in Three Species," *Int. J. of Impotence Research*, Smith–Gordon, London, vol. 7, pp. 49–56 (1995).

Michael C. Truss et al, "Role of the Nitric Oxide Donor Linsidomine Chlorhydrate (SIN–1) in the Diagnosis and Treatment of Erectile Dysfunction," *Urology*, vol. 44, No. 4, pp. 553–556 (Oct. 1994).

Subbarao Vemulapalli et al, "Antiplatelet and Antiproliferative Effects of SCH 51866, a Novel Type 1 and Type 5 Phosphodiesterase Inhibitor", *Journal of Cardiovascular Pharmacology*, vol. 28, pp. 862–869 (1996).

Richard J. Weiss, "Effects of Antihypertensive Agents on Sexual Function," *Am. Family Physician*, vol. 44, No. 6, pp. 2075–2082 (Dec. 1991).

E. Douglas Whitehead et al, "Treatment alternatives for impotence", *PGM Symposium*, vol. 88, No. 2, pp. 139–149, 152 (Aug. 1990).

Chackalamannil, Application #09/940,760. Filed Aug. 28, 2001.

Asberom, Application #10/227,778. Filed Aug. 26, 2002.

Asberom, Application #10/290,011. Filed Nov. 7, 2002.

* cited by examiner

XANTHINE PHOSPHODIESTERASE V INHIBITORS

CROSS-REFERENCE TO RELATED APPLICATIONS

This application claims the benefit of U.S. Provisional Application Ser. No. 60/233,567, filed Sep. 19, 2000.

BACKGROUND OF THE INVENTION

1. Field of the Invention

The invention relates to polycyclic nucleotide xanthine phosphodiesterase V inhibitors.

2. Description of Related Art

Phosphodiesterase ("PDE") V inhibitor compounds are described by Kenneth J. Murray in *Phosphodiesterase $V_A$ Inhibitors, DN & P* 6(3), pp. 150–156 (April, 1993), which is hereby incorporated herein by reference in its entirety, to have potential therapeutic value for a number of physiological disorders. One compound disclosed in the Murray article is MIMAX, a polycyclic xanthine PDE V inhibitor substituted at its 8-position with a —NHCH$_3$ group.

U.S. Pat. No. 5,409,934, which is hereby incorporated herein by reference in its entirety, discloses a series of xanthine PDE V inhibitors that are substituted at the 8-position with, among other possibilities, one of the following groups: —NO$_2$, —NR$^s$R$^t$ or —NR$^6$SO$_2$R$^5$, where R$^s$ and R$^t$, independently of one another, are each a hydrogen atom or an alkyl group, or R$^s$ and R$^t$, together with the nitrogen atom to which they are both attached, form a phthalimido group, R$^5$ is an alkyl or aryl group, and R$^6$ is a hydrogen atom or —SO$_2$R$^7$, where R$^7$ is an alkyl or aryl group.

U.S. Pat. No. 5,470,579, which is hereby incorporated herein by reference in its entirety, discloses a xanthine PDE V inhibitor having a substituted or unsubstituted —NH$_2$ group at the 8-position, for example, —NHR, where R is a C$_1$–C$_6$ alkyl group.

WO 93/23401, which is hereby incorporated herein by reference in its entirety, discloses xanthine PDE V inhibitors that are substituted at the 8-position with —NH(CH$_2$)$_2$CH(CH$_2$OR$^4$)$_2$.

WO 92/05176, which is hereby incorporated herein by reference in its entirety, discloses 8-acylaminoxanthine PDE V inhibitors that are substituted at the 8-position with —NHCOC$_6$H$_5$COOH.

WO 92/05175, which is hereby incorporated herein by reference in its entirety, discloses 8-aminoxanthine PDE V inhibitors that are substituted at the 8-position with —NH$_2$ or —NHR, where R is an alkyl, arylalkyl or unsaturated heterocyclic (e.g., heteroaryl) group.

Specific PDE V inhibitors have been found useful for specific indications. For example, the use of PDE V inhibitors for treating impotence has met with commercial success with the introduction of sildenafil citrate, better known as Viagra® (Pfizer, N.Y., N.Y.). The chemistry and use of Viagra®, including its mechanism of action in treating erectile dysfunction, are taught in EP 0 702 555 B1, which is hereby incorporated herein by reference in its entirety. Additional PDE V inhibitors useful for treating erectile dysfunction are disclosed in WO 99/24433, which is hereby incorporated herein by reference in its entirety.

Erectile dysfunction is a treatable and highly recognized health concern, affecting more than 30 million men in the United States, including one in four over age 65. Erectile dysfunction occurs when a man consistently is unable to sustain an erection sufficient for conducting sexual intercourse. In the past, psychological reasons were the most common explanation for erectile dysfunction or it was considered a natural part of aging. However, researchers today acknowledge that more than 70 percent of instances of erectile dysfunction are due to physical or medical problems. There are several factors that may contribute to erectile dysfunction, including:

Poor blood circulation—atherosclerosis or hardening of the arteries, high blood pressure and high cholesterol.

Neurological disorders—multiple sclerosis, Alzheimer's disease and Parkinson's disease.

Hormone imbalances—diabetes, thyroid disorders and low testosterone levels.

Trauma—spinal cord injury, prostate surgery or other trauma to the pelvic area.

Prescription and over-the-counter medications—blood pressure medications, antidepressants and certain drug combinations.

Lifestyle habits—smoking, alcohol abuse and using illegal drugs.

U.S. Pat. No. 5,939,419 and U.S. Pat. No. 5,393,755, both of which are hereby incorporated herein by reference in their entirety, disclose polycyclic guanine PDE V derivatives that are useful for the treatment of cardiovascular and pulmonary disorders.

As has been shown by the representative art cited above, certain xanthine/guanine PDE V inhibitors have been found to be useful for treating cardiovascular and pulmonary disorders, while some others have been found useful for treating impotence. It has been further shown that certain xanthine PDE V inhibitors can be substituted at the 8-position by a variety of groups, including nitro and unsubstituted or substituted amino groups. The substituted amino groups include saturated heterocycles, where the nitrogen atom and its substituents together form an unsaturated heterocyclic group (e.g., —NR$^x$R$^y$ can form a heterocycle).

It is an object of this invention to provide a polycyclic xanthine PDE V inhibitor that possesses beneficial therapeutic properties.

It is a further object of the invention to provide a polycyclic xanthine PDE V inhibitor that has especially useful pharmacological properties.

It is yet another object of the invention to provide a polycyclic xanthine PDE V inhibitor that has good metabolic stability.

It is still another object of the invention to provide a polycyclic xanthine PDE V inhibitor that is effective for treating a variety of physiological symptoms and diseases in which PDE V plays a role.

It is also an object of the invention to provide a polycyclic xanthine PDE V inhibitor that is especially effective for treating erectile dysfunction with minimal side effects.

These and other objects of the invention will become apparent as the description progresses.

Definitions and Usage of Terms

The following definitions and terms are used herein or are otherwise known to a skilled artisan. Except where stated otherwise, the following definitions apply throughout the specification and claims. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

The term "chemically-compatible," as used herein, means that a substituent or variable in a structure, process or the like is selected to be capable of resulting in a stable compound.

The term "substituted" or the phrase "with . . . one or more substituents," as used herein, means the replacement of one or more atoms or radicals, usually hydrogen atoms, in a given structure with a chemically-compatible atom(s) or radical(s) selected from a specified group. In the situations where more than one atom or radical may be replaced with substituents selected from the same specified group, the substituents may be, unless otherwise specified, either the same or different at every position. Radicals of specified groups, such as alkyl, cycloalkyl, alkenyl, cycloalkenyl, alkynyl, arylalkyl, alkylaryl, heterocycloalkyl, aryl and heteroaryl groups, independently of or together with one another, may be substituents for any substituted group, unless otherwise known, stated or shown to be to the contrary.

Representative substituents for alkyl, cycloalkyl, alkenyl, cycloalkenyl, alkynyl, arylalkyl, alkylaryl, aryl, heteroaryl and heterocycloalkyl groups include, but are not limited to, the following moieties: alkyl, cycloalkyl, alkenyl, cycloalkenyl, alkynyl, arylalkyl, alkylaryl, aryl, heteroaryl, heterocycloalkyl, hydroxyalkyl, arylalkyl, aminoalkyl, haloalkyl, thioalkyl, alkylthioalkyl, carboxyalkyl, imidazolylalkyl, indolylalkyl, mono-, di- and trihaloalkyl, mono-, di- and trihaloalkoxy, amino, alkylamino, dialkylamino, alkoxy, hydroxy, halo (e.g., —Cl and —Br), nitro, oximino, —COOR$^{50}$, —COR$^{50}$, —SO$_{0-2}$R$^{50}$, —SO$_2$NR$^{50}$R$^{51}$, NR$^{52}$SO$_2$R$^{50}$, =C(R$^{50}$R$^{51}$), =N—OR$^{50}$, =N—CN, =C(halo)$_2$, =S, =O, —CON(R$^{50}$R$^1$), —OCOR$^{50}$, —OCON(R$^{50}$R$^{51}$), —N(R$^{52}$)CO(R$^{50}$), —N(R$^{52}$)COOR$^{50}$ and —N(R$^{52}$)CON(R$^{50}$R$^{51}$), where:

R$^{50}$, R$^{51}$ and R$^{52}$ may be independently selected from the following: a hydrogen atom and a branched or straight-chain, C$_{1-6}$ alkyl, C$_{3-6}$ cycloalkyl, C$_{4-6}$ heterocycloalkyl, heteroaryl and aryl group, with or without substituents. When permissible, R$^{50}$ and R$^{51}$ can be joined together to form a carbocyclic or heterocyclic ring system. R$^{50}$, R$^{51}$ and R$^{52}$ may also include:

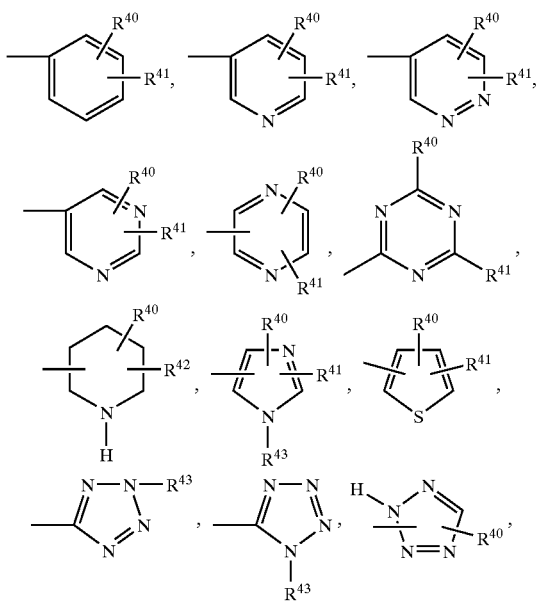

where,

R$^{40}$ and R$^{41}$ are, independently of one another, each a hydrogen atom or a branched or straight-chain, optionally substituted, alkyl, cycloalkyl, heterocycloalkyl, halo, aryl, imidazolylalkyl, indolylalkyl, heteroaryl, arylalkyl, arylalkoxy, heteroarylalkyl, heteroarylalkoxy, aminoalkyl, haloalkyl, mono-, di- or trihaloalkyl, mono-, di- or trihaloalkoxy, nitro, cyano, alkoxy, hydroxy, amino, phosphino, phosphate, alkylamino, dialkylamino, formyl, alkylthio, trialkylsilyl, alkylsulfonyl, arylsulfonyl, alkylsulfinyl, aminoalkyl, alkylaminoalkyl, dialkylaminoalkyl, hydroxyalkyl, morpholino, thioalkyl, alkylthioalkyl, carboxyalkyl, oximino, —COOR$^{50}$, —COR$^{50}$, —SO$_{0-2}$R$^{50}$, —SO$_2$NR$^{50}$R$^{51}$, —NR$^{52}$SO$_2$R$^{50}$, —CON(R$^{50}$R$^{51}$), —OCON(R$^{50}$R$^{51}$), —N(R$^{52}$)CO(R$^{50}$), —N(R$^{52}$)COOR$^{50}$, —N(R$^{52}$)CON(R$^{50}$R$^{51}$) or —OCONR$^{50}$ group, where, R$^{50}$, R$^{51}$ and R$^{52}$ are as defined above;

R$^{42}$ is a hydrogen atom or a branched or straight-chain, optionally substituted, alkyl, alkenyl, arylalkyl or acyl group; and R$^{43}$ is a hydrogen atom or a branched or straight-chain, optionally substituted, alkyl or aryl group;

wherein, the optional substituents are defined the same as above for the one or more substituents.

Preferred substituents on aryl and heteroaryl groups include, but are not limited to, any of the moieties recited above in the definition for R$^{40}$ and R$^{41}$.

The term "heteroatom," as used herein, means a nitrogen, sulfur, or oxygen atom. Multiple heteroatoms in the same group may be the same or different.

The term "hydrocarbon," as used herein, means a compound or radical consisting of only carbon and hydrogen atoms, including aliphatic, aromatic, normal, saturated and unsaturated hydrocarbons.

The term "alkyl," as used herein, means an unsubstituted or substituted, straight or branched, hydrocarbon chain (i.e., comprising carbon and hydrogen atoms bonded together), having, preferably, from one to twenty-four carbon atoms, more preferably, from one to twelve carbon atoms, and most preferably, from one to eight carbon atoms.

The term "cycloalkyl" or "cycloalkane," as used herein, means an unsubstituted or substituted, saturated, stable non-aromatic carbocyclic ring, having, preferably, from three to fifteen carbon atoms, more preferably, from three to eight carbon atoms. The carbon ring radical is saturated and may be fused, for example, benzofused, with one to three cycloalkyl, aromatic, heterocyclic or heteroaromatic rings. The cycloalkyl may be attached at any endocyclic carbon atom that results in a stable structure. Preferred carbocycles have from five to six carbons. Examples of carbocycle radicals include cyclopropyl, cyclobutyl, cyclopentyl, cyclohexyl, cycloheptyl and the like.

The term "alkenyl," as used herein, means an unsubstituted or substituted, unsaturated, straight or branched, hydrocarbon chain having at least one double bond present and, preferably, from two to fifteen carbon atoms, more preferably, from two to twelve carbon atoms.

The term "cycloalkenyl," as used herein, means an unsubstituted or substituted, unsaturated carbocyclic ring having at least one double bond present and, preferably, from three to fifteen carbon atoms, more preferably, from five to eight carbon atoms. A cycloalkenyl goup is an unsaturated carbocyclic group. Examples of cycloalkenyl groups include cyclopentenyl and cyclohexenyl.

The term "alkynyl," as used herein, means an unsubstituted or substituted, unsaturated, straight or branched, hydrocarbon chain having at least one triple bond present and, preferably, from two to twelve carbon atoms, more preferably, two to ten carbon atoms.

The term "bicycloalkyl," as used herein, represents a saturated linearly fused or bridged carbocyclic ring having, preferably, from 5 to 12 carbon atoms.

The term "aryl," as used herein, means a substituted or unsubstituted, aromatic, mono- or bicyclic carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl and the like. If desired, the carbocyclic moiety can be substituted with from one to five, preferably, one to three moieties, such as mono-through pentahalo, alkyl, trifluoromethyl, phenyl, hydroxy, alkoxy, phenoxy, amino, monoalkylamino, dialkylamino and the like.

The term "heteroaryl," as used herein, means a mono- or bicyclic ring system containing one or two aromatic rings and at least one nitrogen, oxygen or sulfur atom in an aromatic ring. Heteroaryl groups (including bicyclic heteroaryl groups) can be unsubstituted or substituted with a plurality of substituents, preferably, one to five substituents, more preferably, one, two or three substituents (e.g., mono-through pentahalo, alkyl, trifluoromethyl, phenyl, hydroxy, alkoxy, phenoxy, amino, monoalkylamino, dialkylamino and the like). Typically, a heteroaryl group represents a cyclic group of five or six atoms, or a bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "arylalkyl," as used herein, means an alkyl moiety substituted with an optionally substituted, aryl or heteroaryl group. Representative arylalkyl groups include a benzyl group and fused bicyclic systems which contain one aryl group.

The term "alkylaryl," as used herein, means an aryl or heteroaryl moiety substituted with an optionally substituted, alkyl group. Representative alkylaryl groups include o-, m- and p-linked tolyl and xylyl groups.

Unless otherwise known, stated or shown to be to the contrary, the point of attachment for a multiple term substituent (multiple terms that are combined to identify a single moiety) to a subject structure is through the last named term of the multiple term. For example, an "arylalkyl" substituent attaches to a targeted structure through the "alkyl" portion of the substituent. Conversely, when the substituent is "alkylaryl", it attaches to a targeted structure through the "aryl" portion of the substituent. Similarly, a cycloalkylalkyl substituent attaches to a targeted through the latter "alkyl" portion of the substituent (e.g., Structure-alkyl-cycloalkyl).

The term "heterocycloalkyl," as used herein, means an unsubstituted or substituted, saturated cyclic ring system having from three to fifteen members, preferably, from three to eight members, and comprising carbon atoms and at least one heteroatom as part of the ring.

The term "heterocyclic ring" or "heterocycle," as used herein, means an unsubstituted or substituted, saturated, unsaturated or aromatic ring, comprised of carbon atoms and one or more heteroatoms in the ring. Heterocyclic rings may be monocyclic or polycyclic. Monocyclic rings preferably contain from three to eight atoms, most preferably, five to seven atoms. Polycyclic ring systems consisting of two rings preferably contain from six to sixteen atoms, most preferably, ten to twelve atoms. Polycyclic ring systems consisting of three rings contain, preferably, from thirteen to seventeen atoms, most preferably, fourteen to fifteen atoms. Each heterocyclic ring has at least one hetero atom. Unless otherwise stated, the heteroatoms may be independently selected from the following: nitrogen, sulfur and oxygen atoms.

The term "carbocyclic ring" or "carbocycle," as used herein, means an unsubstituted or substituted, saturated, unsaturated or aromatic (e.g., aryl), hydrocarbon ring, unless otherwise specifically identified. Carbocycles may be monocyclic or polycyclic. Monocyclic rings preferably contain from three to eight atoms, most preferably, five to seven atoms. Polycyclic rings having two rings preferably contain from six to sixteen atoms, most preferably, ten to twelve atoms, and those having three rings preferably contain from thirteen to seventeen atoms, most preferably, fourteen to fifteen atoms.

The term "alkoxy," as used herein, means an oxygen atom bonded to a hydrocarbon chain, such as an alkyl or alkenyl group (e.g., —O-alkyl or —O-alkenyl). Representative alkoxy groups include methoxy, ethoxy, a isopropoxy groups.

The term "hydroxyalkyl," as used herein, means a substituted hydrocarbon chain, preferably, an alkyl group, having at least one hydroxy substituent (ie., —OH). Additional substituents to the alkyl group may also be present. Representative hydroxyalkyl groups include hydroxymethyl, hydroxyethyl and hydroxypropyl groups.

The term "carboxyalkyl," as used herein, means a substituted hydrocarbon chain, preferably, a substituted alkyl group, which has a carboxyl substituent (e.g., —COOH) and may also have additional substituents (such as one of the representative substituents identified above for the term "substituted"). Representative carboxyalkyl groups include carboxymethyl (—CH$_2$CO$_2$H) and carboxyethyl (—CH$_2$CH$_2$CO$_2$H) groups, and derivatives thereof, such as the corresponding esters.

The term "aminoalkyl," as used herein, means an alkyl group substituted with an amine moiety (e.g., —alkylNH$_2$), such as aminomethyl.

The term "alkylamino," as used herein, means an amino moiety having from one or two alkyl substituents (e.g., —NH-alkyl), such as dimethylamino.

The term "alkenylamino," as used herein, means an amino moiety having from one or two alkenyl substituents, where the nitrogen atom of the amino group is not attached to the alkene-forming carbon atom (e.g., —NH—CH$_2$-alkenyl), such as dibutenylamino.

The term "arylamino," as used herein, means an amine moiety substituted with an aryl group (i.e., —NH-aryl).

The term "alkylimino," as used herein, means an imino moiety having one alkenyl or two alkyl substituents (e.g., —C=N-alkyl).

The term "oximino," as used herein, means compounds containing the —C=N—OR$^{69}$ radical, where R$^{69}$ is a hydrogen atom or an alkyl or aryl group.

The term "aroyl," as used herein, means the radical R—CO—; where R is an aromatic group. Representative aroyls are benzoyl and naphthoyl.

The term "aryloxy," as used herein, means an oxygen atom having an aryl substituent (e.g., —O-aryl).

The term "ester," as used herein, means compounds containing a substituted carboxylic acid (e.g., —COO-aryl).

The term "acyl" or "carbonyl," as used herein, means a carbon to oxygen double bond, (e.g., R—C(=O)—), which can be a radical of a carboxylic acid having the formula alkyl-CO—, aryl-CO—, arylalkyl-CO—, cycloalkyl-CO—, alkylcycloalkyl-CO— or heteroaryl-CO—. Representative acyl groups include acetyl, propionyl, butanoyl and benzoyl groups.

The term "acyloxy," as used herein, means an oxygen atom having an acyl substituent (e.g., —O-acyl), for example, —O—C(=O)-alkyl.

The term "acylamino," as used herein, means an amino moiety having an acyl substituent (e.g., —NH-acyl), for example, an amide with the formula —NH—(C=O)-alkyl, a urea with the formula —NH—(C=O)—NH-alkyl or a carbamate with the formula —NH—(C=O)—OR, where R is an alkyl, cycloalkyl, alkenyl, cycloalkenyl, alkynyl, arylalkyl or heterocycloalkyl group.

The term "halo," "halogen" or "halide," as used herein, means a chloro, bromo, fluoro or iodo atom radical. Chlorides, bromides and fluorides are preferred halides.

The term "lower hydrocarbon" (e.g., "lower alkyl"), as used herein, means a hydrocarbon chain comprised of from, unless otherwise stated, one to eight carbon atoms, preferably, one to six carbon atoms, and most preferably, one to four carbon atoms.

The term "polyhalo," as used herein, represents substitution of at least two halo atoms to a group modified by the term "polyhalo."

The term "aminosulfonyl," as used herein, represents a group having the formula: —SO$_2$NR$^{79}$R$^{89}$, where R$^{79}$ and R$^{89}$ are, independently of one another, each a hydrogen atom or a lower alkyl (e.g., from 1 to 6 carbon atoms) or aryl group.

The term "sulfonyl," as used herein, represents a group having the formula: —S(O)$_2$—.

When a variable appears more than once in a structural formula, for example, R$^{59}$ for where X is —C(OR$^{59}$)$_2$—, the identity of each variable appearing more than once may be independently selected from the definition for that variable.

The term "prodrug," as used herein, represents a compound that is a drug precursor, which following administration to a patient, releases a drug in vivo via some kind of chemical and/or physiological process (e.g., a prodrug on being brought to a physiological pH and/or through an enzyme action is converted to a desired drug form).

The term "compound of the formula (I.1) or (II.1)", as used herein, represents a compound having a chemical structure encompassed by the formula (I.1) or (II.1), and includes any and all enantiomers, stereoisomers, rotomers, tautomers and prodrugs of the compound. Compounds of the formula (I.1) or (II.1) also include their corresponding pharmaceutically-acceptable salts, solvates, esters and derivatives.

The term "pharmaceutically-acceptable excipients," as used herein, includes any physiologically inert, pharmacologically inactive material known to one skilled in the art, which is compatible with the physical and chemical characteristics of the particular active ingredient selected for use. Pharmaceutically-acceptable excipients include polymers, resins, plasticizers, fillers, binders, lubricants, glidants, disintegrates, solvents, co-solvents, buffer systems, surfactants, preservatives, sweetening agents, flavoring agents, pharmaceutical grade dyes or pigments, and viscosity agents.

The term "pharmaceutical composition," as used herein, means a combination of at least one inventive compound (e.g., PDE V inhibitor) and at least one pharmaceutically-acceptable excipient.

The terms "compound [having the formula (I)] or a pharmaceutical composition thereof" include neutral, acidic and alkaline forms of the compound or composition, as well as solvates, esters and salts (as are defined below) thereof, and further includes derivatives of the inventive compounds.

The term "pharmaceutically-acceptable salt," as used herein, means a cationic salt formed at an acidic (e.g., carboxyl) group or an anionic salt formed at a basic (e.g., amino) group of the compound. Many such salts are known in the art, for example, those that are described in WO 87/05297 (1987), which is hereby incorporated in its entirety by reference herein. Preferred cationic salts include the alkali-metal salts (e.g., sodium and potassium) and alkaline earth metal salts (e.g., magnesium and calcium). Preferred anionic salts include the halide (e.g., chloride), acetate and phosphate salts.

The phrase "effective amount," as used herein, means an amount of a compound or composition which is sufficient to significantly and positively modify the symptoms and/or conditions to be treated (e.g., provide a positive clinical response). The phrase "safe and effective amount," as used herein, means that an "effective amount" must also be safe, that is, an amount that is sufficient to provoke a positive response, yet is small enough to avoid serious side effects (at a reasonable benefit/risk ratio), within the scope of sound medical judgment. The effective amount of an active ingredient for use in a pharmaceutical composition will vary with the particular condition being treated, the severity of the condition, the duration of the treatment, the nature of concurrent therapy, the particular active ingredient being employed, the particular pharmaceutically-acceptable excipients utilized and like factors within the knowledge and expertise of the attending physician.

The phrase "administering [to a patient a safe and effective amount of the inventive compound]," as used herein, refers to any mode of introducing any form (e.g., solid, liquid or gas) of the inventive compounds in vivo to a patient (e.g., human or mammal). For example, introduction of the inventive compound to a patient may be accomplished via oral ingestion (e.g., tablets, capsules, gels, solutions, etc.), adsorption, absorption (e.g., transmucosal sublingual or buccal administration), transdermal applications (e.g., topical applications via patches, lotions, etc.), suppositories, etc.

The term "oral dosage form," as used herein, means any pharmaceutical composition intended to be systemically administered to an individual by delivering the composition to the gastrointestinal tract of an individual, via the mouth of the individual. For purposes of the invention, the delivered form can be a tablet (coated or non-coated), solution, suspension or capsule (coated or non-coated).

The term "injection," as used herein, means any pharmaceutical composition intended to be systemically administered to a human or other mammal, via delivery of a solution or emulsion containing the active ingredient, by puncturing the skin of said individual, in order to deliver the solution or emulsion to the circulatory system of the individual either by intravenous, intramuscular, intraperitoneal or subcutaneous injection.

Other than as shown in the operating examples or where is otherwise indicated, all numbers used in the specification and claims expressing quantities of ingredients, reaction conditions, and so forth, are understood as being modified in all instances by the term "about."

SUMMARY OF THE INVENTION

The invention comprises a compound having the formula (I):

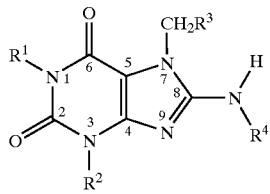

(I)

where, (a) $R^1$ and $R^2$ are, independently of one another, each a $C_{1-15}$ alkyl group, branched or straight chain, with or without one or more substituents, such as a hydroxy or alkoxy substituent group, a $C_{2-15}$ alkenyl group, branched or straight chain, with or without one or more substituents, a $C_{2-15}$ alkynyl group, branched or straight chain, with or without one or more substituents, a $C_{3-15}$ cycloalkyl group, with or without one or more substituents, an arylalkyl group, with or without one or more substituents, an aryl group, with or without one or more substituents, a heteroaryl group, with or without one or more substituents, —$OR^5$, —$COOR^5$, —$C(O)R^5$ or —$C(O)N(R^5)_2$, where $R^5$ is a hydrogen atom or a hydrocarbon radical, with or without one or more substituents, preferably, $R^5$ is a hydrogen atom or an alkyl group, branched or straight chain, with or without one or more substituents; or one of $R^1$ and $R^2$ is equal to a hydrogen atom, and the other one of $R^1$ and $R^2$ is defined the same as above;

(b) $R^3$ is an aryl group, with or without one or more substituents, such as a hydroxy or alkoxy substituent group, a heteroaryl group, with or without one or more substituents, or a heterocyclic group having from 1 to 3 heteroatoms fused to a 5-or 6-membered aryl ring, with or without one or more substituents, with the proviso that $R^3$ is not an aryl group substituted at its para position with a —Y-aryl group, where Y is a carbon—carbon single bond, —CO—, —O—, —S—, —$N(R^{21})$—, —$CON(R^{22})$—, —$N(R^{22})CO$—, —$OCH_2$—, —$CH_2O$—, —$SCH_2$—, —$CH_2S$—, —$NHC(R^{23})(R^{24})$—, —$NR^{23}SO_2$—, —$SO_2NR^{23}$—, —$C(R^{23})(R^{24})NH$—, —CH=CH—, —CF=CF—, —CH=CF—, —CF=CH—, —$CH_2CH_2$—, —$CF_2CF_2$—,

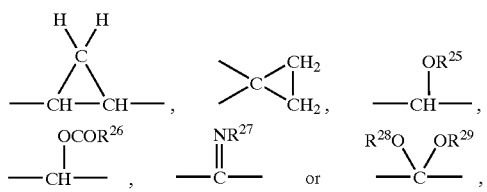

where, $R^{21}$ is a hydrogen atom or a —$CO(C_{1-4}$ alkyl), $C_{1-6}$ alkyl, allyl, $C_{3-6}$ cycloalkyl, phenyl or benzyl group;

$R^{22}$ is a hydrogen atom or a $C_{1-6}$ alkyl group;

$R^{23}$ is a hydrogen atom or a $C_{1-5}$ alkyl, aryl or —$CH_2$-aryl group;

$R^{24}$ is a hydrogen atom or a $C_{1-4}$ alkyl group;

$R^{25}$ is a hydrogen atom or a $C_{1-8}$ alkyl, $C_{1-8}$ perfluoroalkyl, $C_{3-6}$ cycloalkyl, phenyl or benzyl group;

$R^{26}$ is a hydrogen atom or a $C_{1-6}$ alkyl, $C_{3-6}$ cycloalkyl, phenyl or benzyl group;

$R^{27}$ is —$NR^{23}R^{24}$, —$OR^{24}$, —$NHCONH_2$, —$NHCSNH_2$,

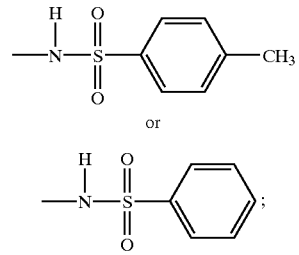

and $R^{28}$ and $R^{29}$ are, independently of one another, each a $C_{1-4}$ alkyl group or, taken together, a —$(CH_2)_q$— group, where q is 2 or 3;

Wherein, $R^{21}$ through $R^{29}$ are with or without one or more substituents; and (c) $R^4$ is a $C_{3-15}$ cycloalkyl group, with or without substituents, such as a hydroxy substituent group, a $C_{3-15}$ cycloalkenyl group, with or without one or more substituents, or a heterocycloalkyl group of 3 to 15 members, with or without one or more substituents;

wherein, the optional one or more substituents for all the groups are chemically-compatible and are, independently of one another, each defined the same as recited above in the definition section.

The invention comprises at least one compound of the formula (I), which includes any and all enantiomers, stereoisomers, rotomers, tautomers and prodrugs of the at least one inventive compound. Compounds of the formula (I) also include their corresponding salts, solvates (e.g., hydrates), esters, and the like. The invention further comprises pharmaceutically-acceptable compositions prepared from an inventive compound or a mixture of inventive compounds, or a salt, solvate or ester thereof. The compounds of formula (I) can be useful for treating a variety of diseases, symptoms and physiological disorders, such as sexual dysfunction, especially impotence (e.g., erectile dysfunction).

A further understanding of the invention will be had from the following description of preferred embodiments.

DESCRIPTION OF PREFERRED EMBODIMENTS

The inventive compounds having the formula (I) are substituted at the 8-position on the chemical structure with an amino group that itself is substituted with one of the following groups: an unsaturated or saturated carbocyclic group and a saturated heterocyclic group. The inventive substituted xanthines exhibited unexpectedly enhanced properties with respect to enzyme activity and enzyme selectivity. It is believed that the substitution at the 8-position of the subject PDE V inhibitor compounds with these specific groups, helped produce unexpectedly highly potent and selective xanthines, which exhibited increased isozyme selectivity when compared to conventional xanthines. Pharmaceutical compositions comprising the inventive compounds possess unexpectedly superior therapeutic properties.

Referring above to the inventive xanthine PDE V inhibitor compounds having the formula (I), the 8-position on the chemical structure is substituted with a —NHR$^4$ group, where R$^4$ represents a carbocyclic or heterocyclic system defined as follows: a C$_{3-15}$ cycloalkyl group, a C$_{3-15}$ cycloalkenyl group or a heterocycloalkyl group of 3 to 15 members. All of the cyclic systems are optionally substituted. Preferred substituents on the cyclic systems include a C$_{3-6}$ cycloalkyl group, a C$_{1-6}$ alkoxy C$_{1-6}$ alkyl group, a C$_{1-6}$ alkyl group, an amino C$_{1-6}$ alkyl group, a C$_{1-6}$ dialkylamino C$_{1-6}$ alkyl group, a C$_{3-6}$ dicycloalkylamino C$_{1-6}$ alkyl group, a hydroxy group, an alkoxy group, an oximino group, —COR$^6$, —SO$_2$R$^6$, —COOR$^6$, —CONR$^6$R$^7$, —SO$_2$NR$^6$R$^7$, —N(R$^8$)SO$_2$R$^6$ and —NR$^6$R$^7$, where:

R$^6$ is a hydrogen atom or an optionally substituted, C$_{1-6}$ alkyl, C$_{3-6}$ cycloalkyl, C$_{3-6}$ heterocycloalkyl, aryl or heteroaryl group;

R$^7$ is a hydrogen atom or an optionally substituted, C$_{1-6}$ alkyl, C$_{3-6}$ cycloalkyl, C$_{3-6}$ heterocycloalkyl, aryl or heteroaryl group; or R$^6$ and R$^7$, when applicable, may be joined together to form a heterocyclic ring system; and R$^8$ is a hydrogen atom or an optionally substituted, C$_{1-6}$ alkyl, C$_{3-6}$ cycloalkyl, C$_{3-6}$ heterocycloalkyl, aryl or heteroaryl group.

Furthermore, R$^4$ may also be substituted with —ZR$^{70}$Z'—, where R$^{70}$, together with Z and Z', form a spiro-fused 5- to 7-membered ring or a linearly fused 4- to 7-membered ring system, and Z and Z', independently of one another, are each an oxygen, sulfur or nitrogen atom. For example, when Z=Z'=O, R$^4$ may be substituted by the following structure having the formula (VIII):

(VIII)

Preferred substituents are defined above for the groups. Other substituents may also be used, such as ketones, oximes, cyclic systems, including lineraly fused and bridged, mono-, bi- and tricyclic rings, spiro-cyclic systems, including ketals and thioketals directly attached to R$^4$, halogens and sulfonamides. One skilled in the art can determine other possible substituents depending on the conditions employed and the desired properties.

A preferred structure of the invention is represented by formula (II):

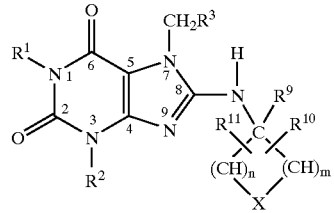

(II)

where,

R$^1$, R$^2$ and R$^3$ are defined the same as above for the compound of formula (I);

R$^9$ is one of the following atoms or groups:
(a) a hydrogen atom;
(b) an oximino group;
(c) a carboxyalkyl group;
(d) a C$_{1-6}$ alkoxy C$_{1-6}$ alkyl group;
(e) an aryloxy C$_{1-6}$ alkyl group;
(f) a C$_{3-6}$ cycloalkoxy C$_{1-6}$ alkyl group;
(g) a heteroaryloxy C$_{1-6}$ alkyl group;
(h) a —COOH group;
(i) an ester group;
(j) a C$_{1-6}$ alkyl group;
(k) a C$_{3-6}$ cycloalkyl group;
(l) a C$_{3-6}$ heterocyclic group;
(m) a hydroxy C$_{1-6}$ alkyl group;
(n) an aryl group; or
(o) a heteroaryl group;
wherein, all of the above groups are optionally substituted;

R$^{10}$ and R$^{11}$ are substituents on the same or different carbon atoms of the ring and, independently of one another, are each defined the same as above for R$^9$ and, additionally, may each be one of the following groups:
(a) a hydroxy group;
(b) an ester group derived from a hydroxy-group with a:
(i) C$_{1-6}$ carboxylic acid;
(ii) C$_{3-6}$ cycloalkyl C$_{1-6}$ carboxylic acid;
(iii) aryl C$_{1-6}$ carboxylic acid; or
(iv) heteroaryl C$_{1-6}$ carboxylic acid group;
(c) a C$_{1-6}$ alkoxy group;
(d) an amino group;
(e) a C$_{1-6}$ mono- or dialkylamino group;
(f) a C$_{1-6}$ alkylacylamino group;
(g) a C$_{1-6}$ alkylsulfonylamino group; or
(h) a —NHCON(R$^{14}$)$_2$ group, where R$^{14}$ is a hydrogen atom or an optionally substituted, alkyl or aryl group; or R$^{10}$ and R$^{11}$, taken together with each other and, optionally, with one or more carbon and/or hetero atoms of the ring, form an optionally substituted, spiro-fused, linearly fused, bi- or tri-cyclic ring system of from 8 to 12 members, including from 0 to 4 hetero atoms, where, all of the above R$^{10}$, R$^1$ and R$^{14}$ groups are optionally substituted;

m and n are, independently of one another, each from 1 to 3; and

X is a chemcially-compatible group, which is —C(R$^{10}$R$^{11}$)—, —S(O)$_y$, —O—, —N(R$^{60}$)—, where:
R$^{10}$ and R$^{11}$ are, independently of one another, each defined the same as previously;
y is from 0 to 2;
R$^{60}$ is a hydrogen atom or a C$_{1-8}$ alkyl, C$_{1-8}$ alkynyl, C$_{1-8}$ alkenyl, C$_{3-8}$ cycloalkyl, aryl, heteroaryl, C$_{4-8}$ heterocycloalkyl, COR$^{61}$, SO$_2$R$^{61}$, COOR$^{61}$, CONR$^{61}$R$^{62}$ or SO$_2$NR$^{61}$R$^{62}$ group, with or without substituents, where:
R$^{61}$ is a hydrogen atom or a C$_{1-8}$ alkyl, C$_{1-8}$ alkynyl, C$_{1-8}$ alkenyl, C$_{3-8}$ cycloalkyl, aryl, heteroaryl or C$_{4-8}$ heterocyclic group, with or without substituents;
R$^{62}$ is a hydrogen atom or a C$_{1-8}$ alkyl, C$_{1-8}$ alkynyl, C$_{1-8}$ alkenyl, C$_{3-8}$ cycloalkyl, aryl, heteroaryl or C$_{4-8}$ heterocyclic group, with or without substituents; and
when R$^{61}$ and R$^{62}$ are (the same or different) alkyl groups, they can, if desired, be joined together to form a carbocyclic or heterocyclic ring system;
wherein, the optional substituents and the one or more substituents are defined the same as for the one or more substituents of formula (I) above.

In the compound of formula (II), the different carbon atoms to which R$^{10}$ and R$^{11}$ may be connected can be adjacent or non-adjacent. Preferably, R$^9$, R$^{10}$ and R$^{11}$ are all hydrogen atoms. In another embodiment of the invention, one of R$^{10}$ or R$^{11}$ is, advantageously, a hydroxy group.

In the compounds of formulas (I) and (II), R$^1$ is, preferably, an alkyl group or an arylalkyl group, particularly, a benzyl group. More preferably, $R^1$ is a lower alkyl group of from 1 to 4 carbon atoms, and most preferably, a methyl or ethyl group.

$R^2$, in the compounds of formulas (I) and (II), is, preferably, an alkyl group, particularly, an alkyl group substituted with a hydroxy group. More preferably, $R^2$ is a lower alkyl group of from 1 to 3 carbon atoms or a hydroxyalkyl group, and most preferably, $R^2$ is a methyl, ethyl, iso-butyl or hydroxyethyl group.

In the compounds of formulas (I) and (II), $R^3$ is, preferably, an aryl group, particularly, an aryl group substituted with a hydroxy-, alkoxy- or amino-sulfonyl group, which may be, advantageously, substituted with 1 or 2 halogen atoms. When $R^3$ is a heteroaryl group in the compounds of formulas (I) and (II), it is generally preferable to utilize heteroaryl groups other than furan. Most preferably, $R^3$ is a methoxyaryl group substituted on its aryl ring with at least one halogen atom, for example, a substitution with 1 or 2 halogen atoms, such as chlorine or bromine. For instance, $R^3$ can be 4-hydroxyphenyl, 3-chloro-4-hydroxyphenyl, 3-bromo-4-hydroxyphenyl, 4-methoxyphenyl, 3-chloro-4-methoxyphenyl, 3-bromo-4-methoxyphenyl, 4-aminosulfonylphenyl group, 3-chloro-4-aminosulfonylphenyl group or 3-bromo-4-aminosulfonylphenyl.

$R^4$, in the compound of formula (I), is, preferably, a cycloalkyl or heterocycloalkyl group, particularly, a cycloalkyl group substituted with a hydroxy group. More preferably, $R^4$ is a cyclohexyl, hydroxycyclopentyl or tetrahydropyranyl group. Most preferably, $R^4$ is a hydroxycyclopentyl group. For instance, $R^4$ can be a 2(R)-hydroxy-1(R)-cyclopentyl group. All of the preferred embodiments may be unsubstituted or substituted.

The compounds of formulas (I) and (II) are useful for treating urogenital diseases, such as male (e.g., impotence/erectile dysfunction) and female sexual dysfunction. The following compounds listed in Tables I and II are illustrative of the invention:

TABLE I

| Compound No. | Structure |
| --- | --- |
| 10 | |
| 11 | |
| 12 | 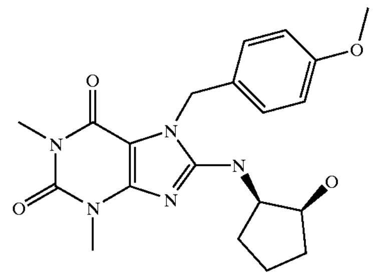 |
| 13 | 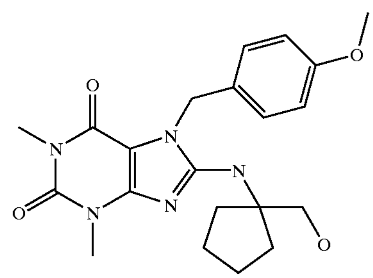 |
| 14 | 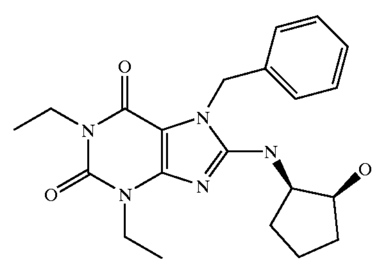 |
| 15 | 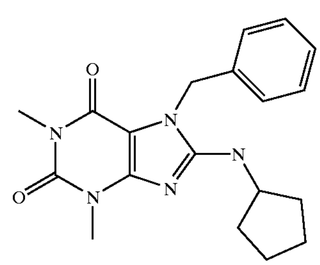 |
| 16 | 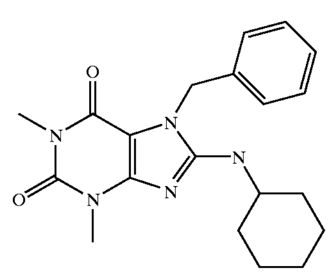 |

TABLE I-continued

| Compound No. | Structure |
|---|---|
| 17 | |
| 18 | |
| 19 | |
| 20 | |
| 21 | 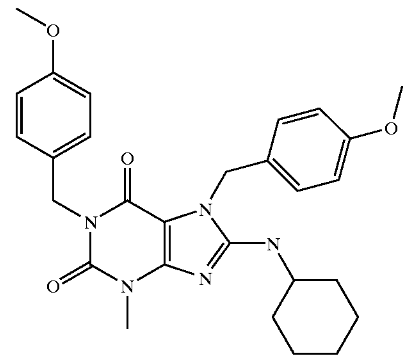 |
| 22 | 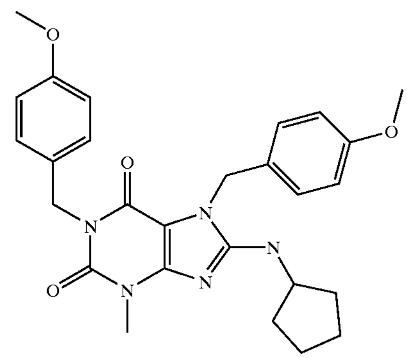 |
| 23 | 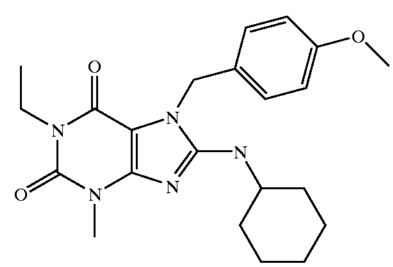 |
| 24 | 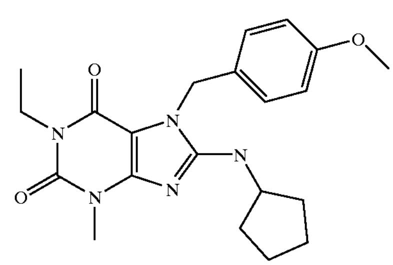 |
| 25 | 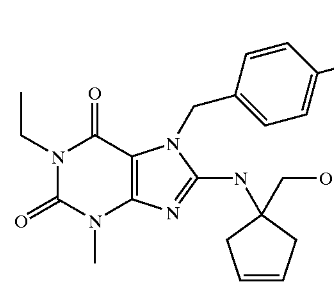 |

TABLE I-continued
| Compound No. | Structure |
|---|---|
| 28 | 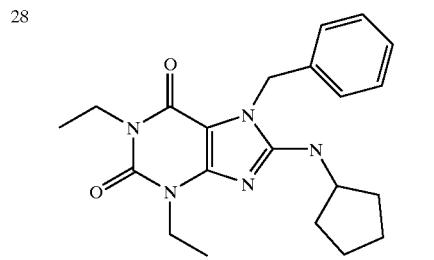 |
| 29 | 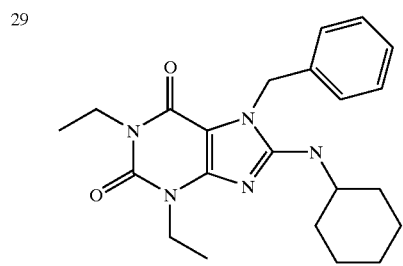 |
| 30 | 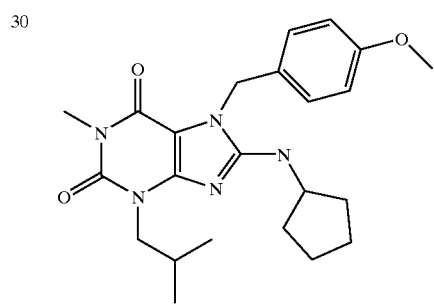 |
| 31 | 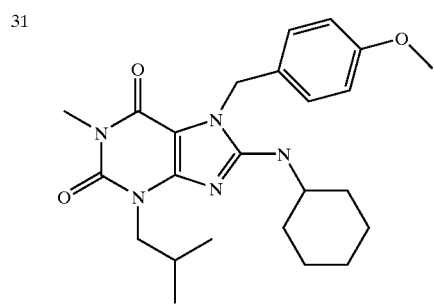 |
| 32 | 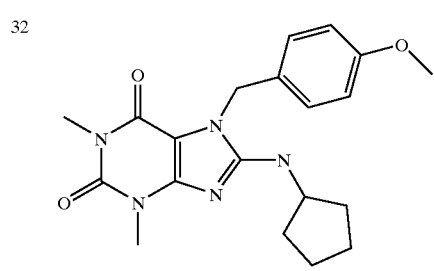 |
| 33 | 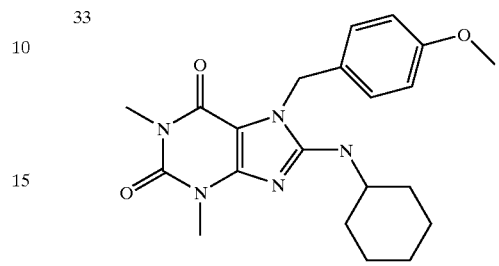 |
| 34 | 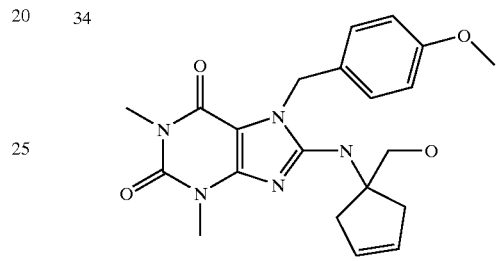 |
| 35 | 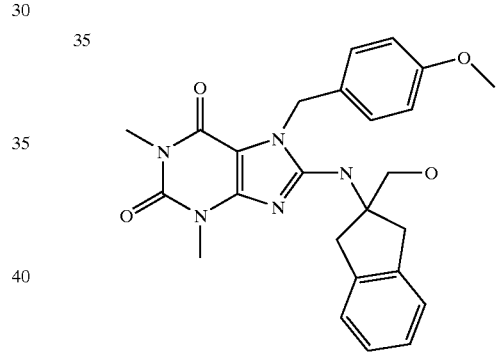 |
| 36 | 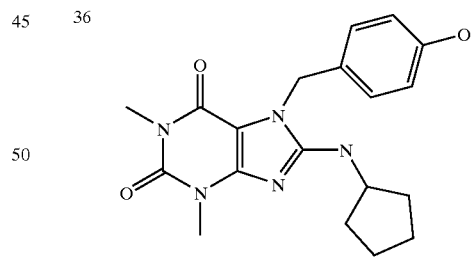 |
| 37 | 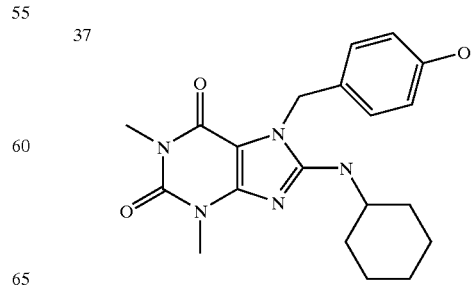 |

TABLE I-continued
| Compound No. | Structure |
|---|---|
| 38 | 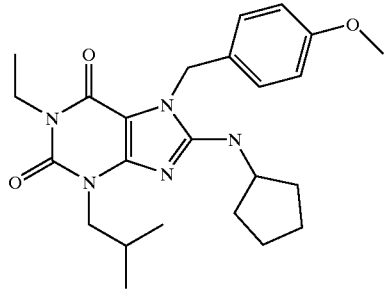 |
| 39 | 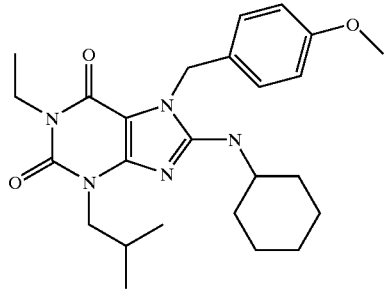 |
| 40 | 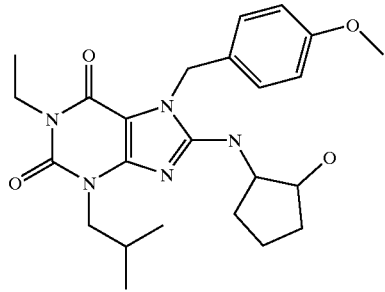 |
| 41 | 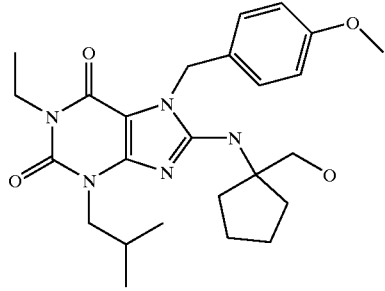 |
| 42 | 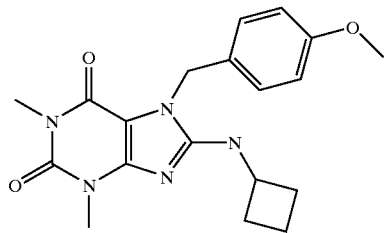 |
| 43 | 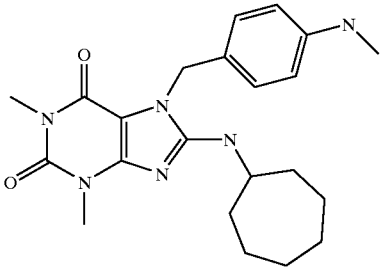 |
| 44 | 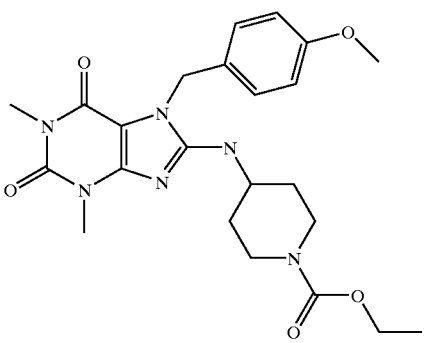 |
| 47 | 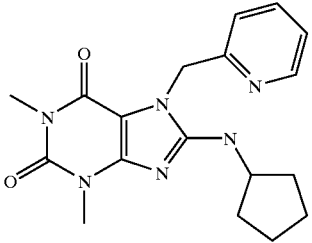 |
| 48 | 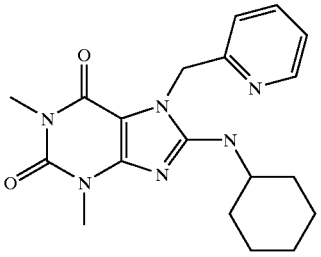 |
| 49 | 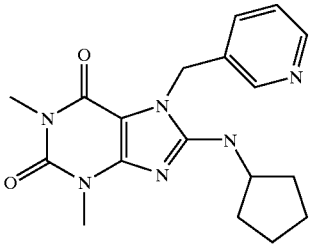 |

TABLE I-continued
| Compound No. | Structure |
|---|---|
| 50 | 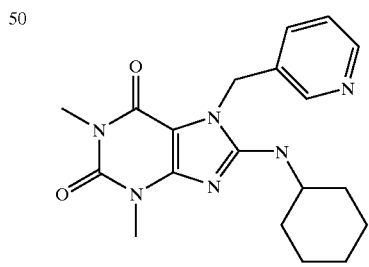 |
| 51 | 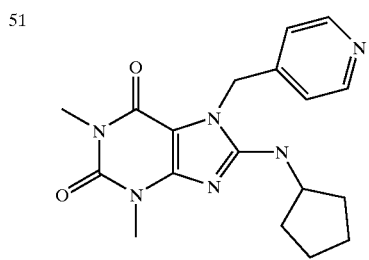 |
| 52 | 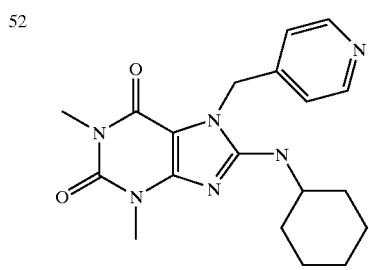 |
| 53 | 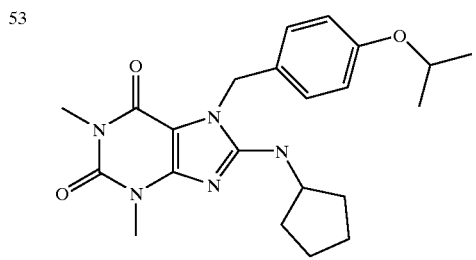 |
| 54 | 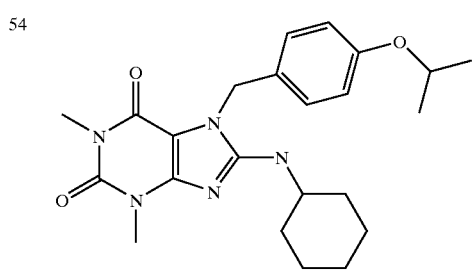 |
| 55 | 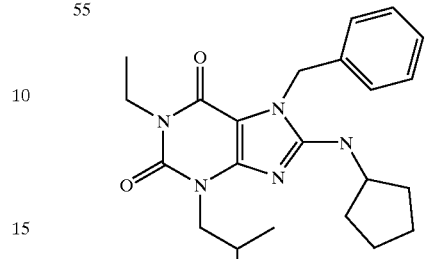 |
| 56 | 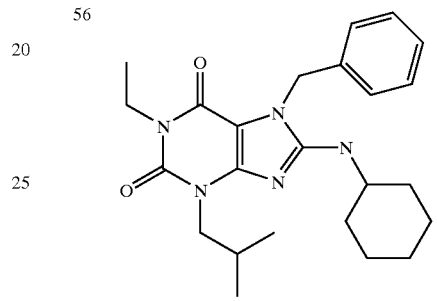 |
| 57 | 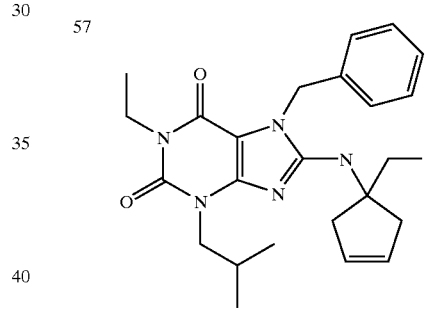 |
| 58 | 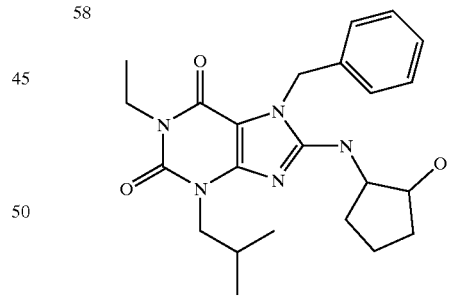 |
| 59 | 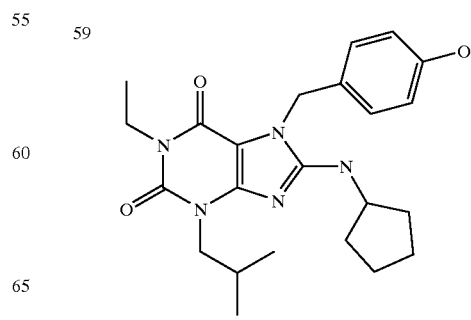 |

TABLE I-continued
| Compound No. | Structure |
|---|---|
| 60 | 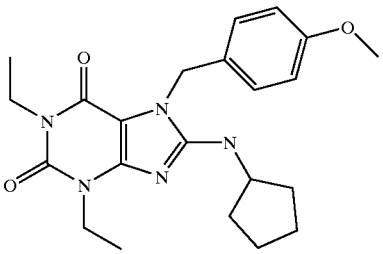 |
| 61 | 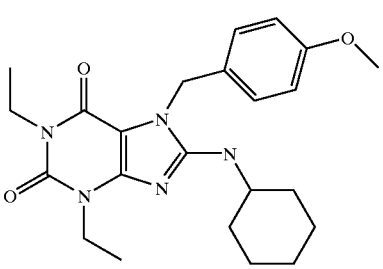 |
| 62 | 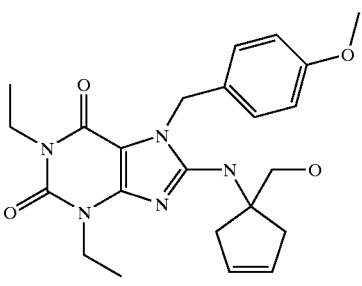 |
| 63 | 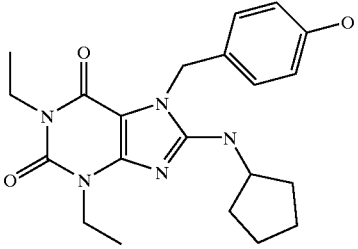 |
| 64 | 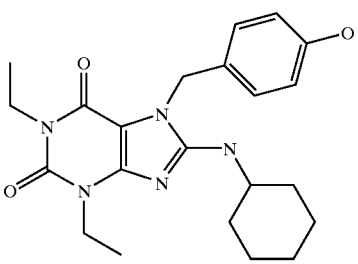 |
| 65 | 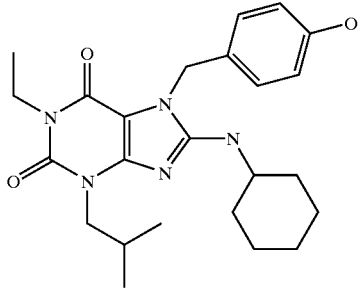 |
| 66 | 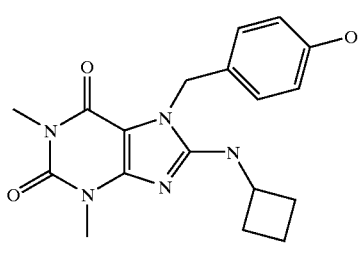 |
| 67 | 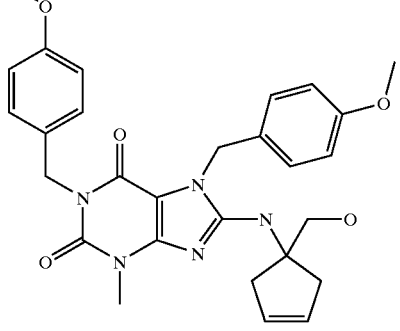 |
| 68 | 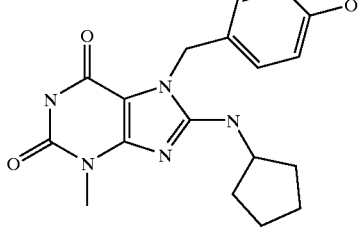 |
| 69 | 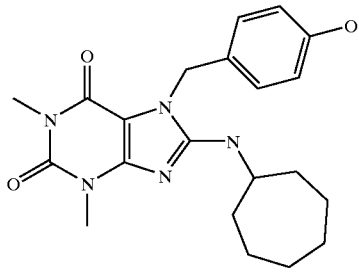 |

TABLE I-continued
| Compound No. | Structure |
|---|---|
| 70 | 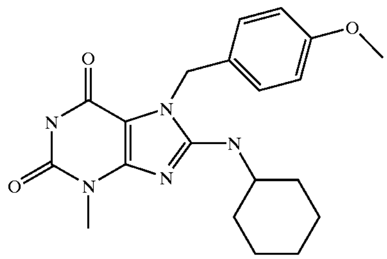 |
| 71 | 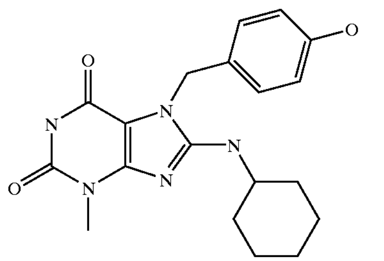 |
| 72 | 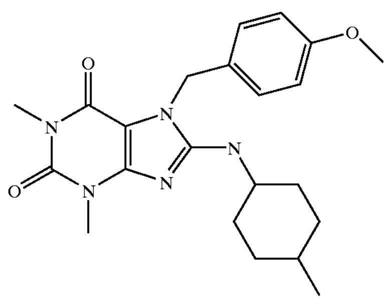 |
| 73 | 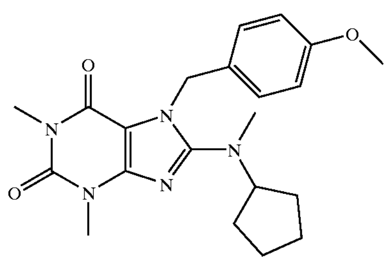 |
| 74 | 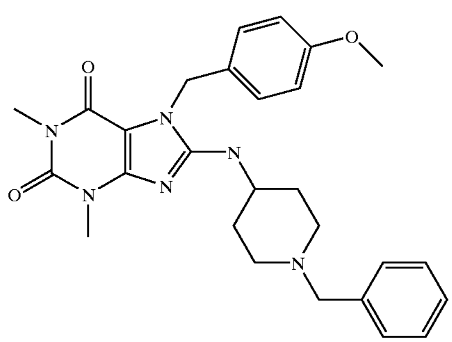 |
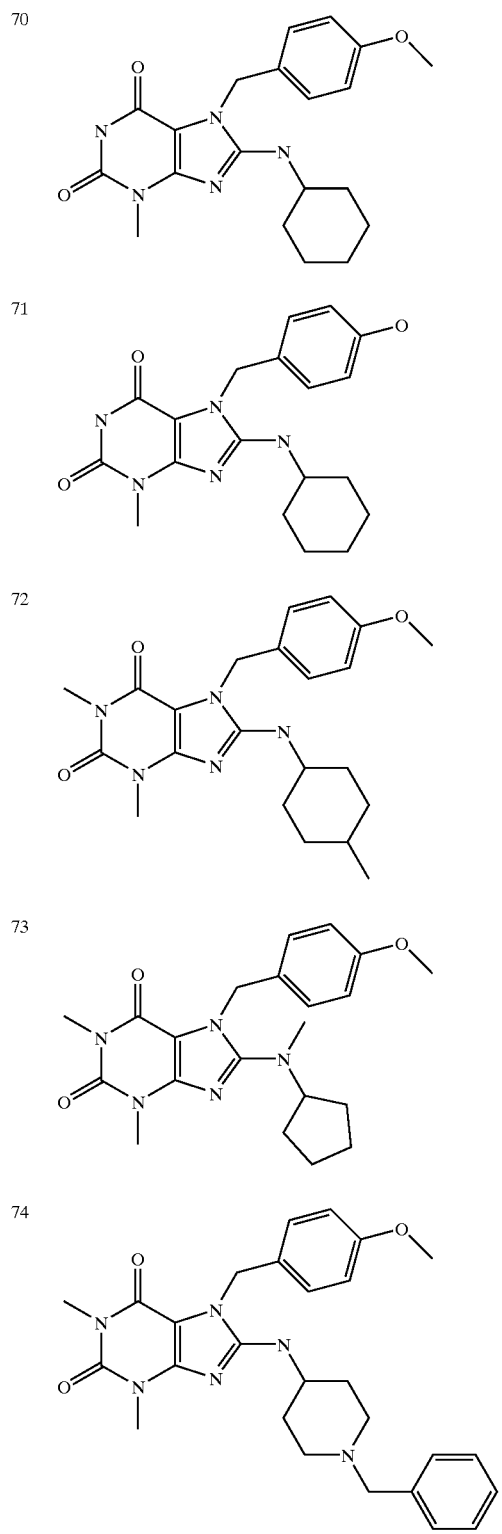
TABLE I-continued
| Compound No. | Structure |
|---|---|
| 75 | 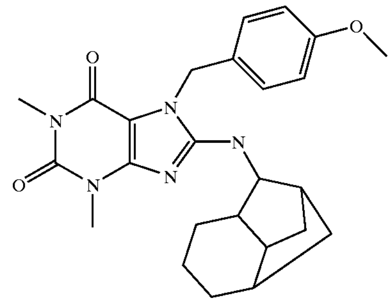 |
| 76 | 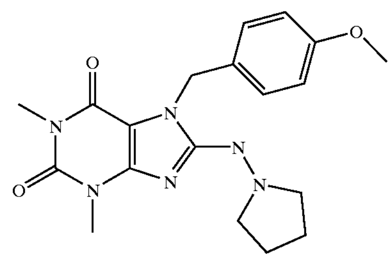 |
| 77 | 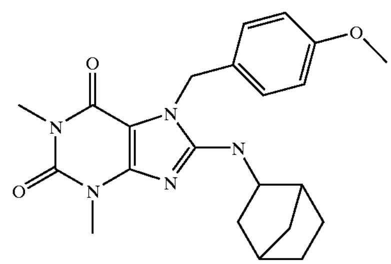 |
| 78 | 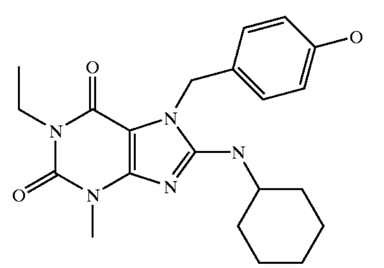 |
| 79 | 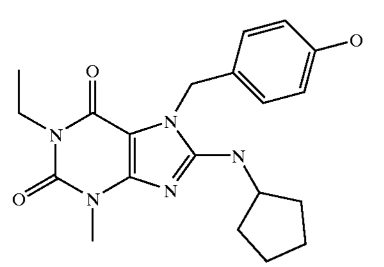 |
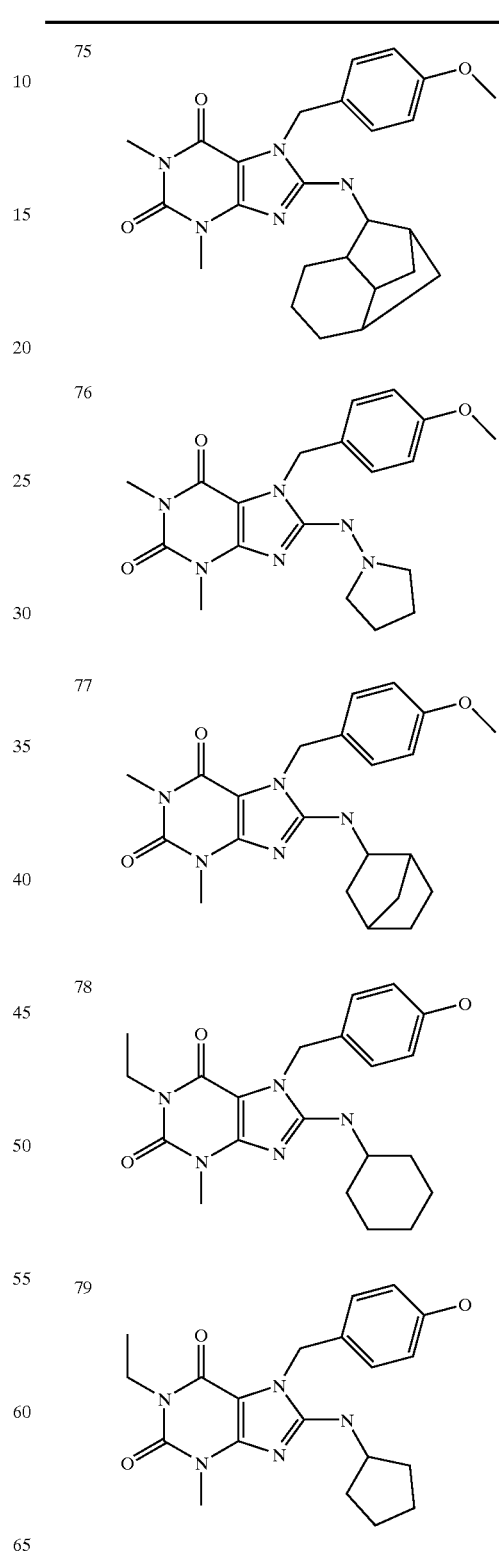

TABLE I-continued

| Compound No. | Structure |
|---|---|
| 80 | |
| 81 | |
| 82 | |
| 83 | |
| 84 | 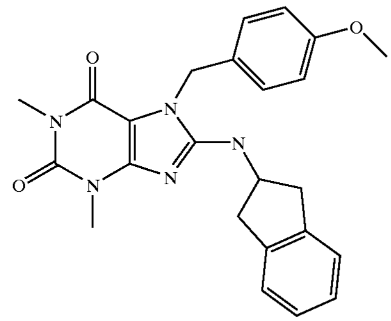 |
| 85 | 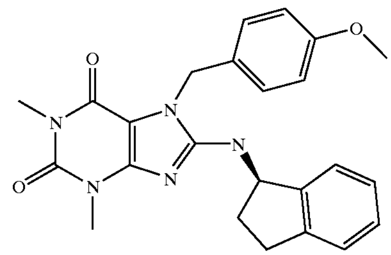 |
| 86 | 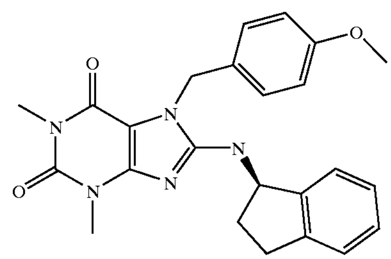 |
| 87 | 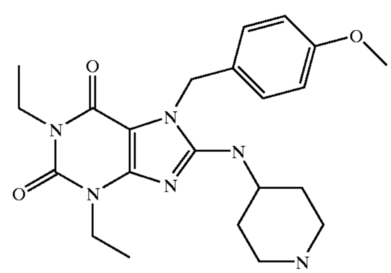 |
| 88 | 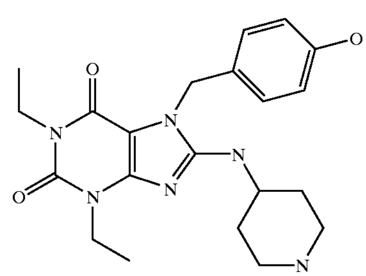 |

TABLE I-continued

| Compound No. | Structure |
|---|---|
| 89 | [structure] |
| 90 | [structure] |
| 91 | [structure] |
| 92 | [structure] |
| 93 | [structure] |
| 94 | [structure] |
| 95 | [structure] |
| 96 | [structure] |
| 97 | [structure] |
| 98 | [structure] |

TABLE I-continued

| Compound No. | Structure |
|---|---|
| 99 | (structure) |

TABLE II

| Compound No. | STRUCTURE | HRMS Calc. | HRMS Found | M, M + 1 |
|---|---|---|---|---|
| 100 | (structure) | 439.2821 | 439.2821 | (M + 1) |
| 101 | (structure) | 412.2349 | 412.2346 | (M + 1) |
| 102 | (structure) | 526.3213 | 526.3203 | (M+) |

TABLE II-continued

| Compound No. | STRUCTURE | HRMS Calc. | HRMS Found | M, M + 1 |
|---|---|---|---|---|
| 103 | 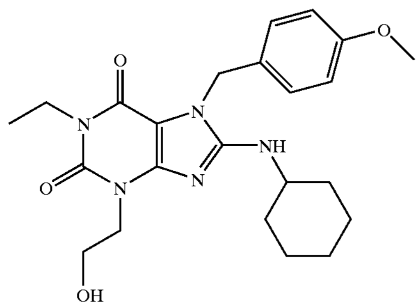 | 442.2454 | 442.2451 | (M + 1) |
| 104 | 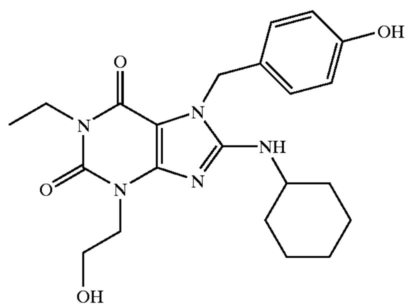 | 428.2298 | 428.2294 | (M + 1) |
| 105 | 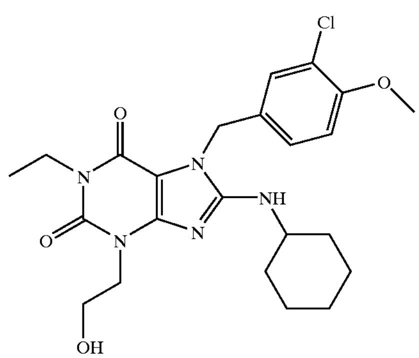 | 476.2065 | 476.2057 | (M + 1) |
| 106 | 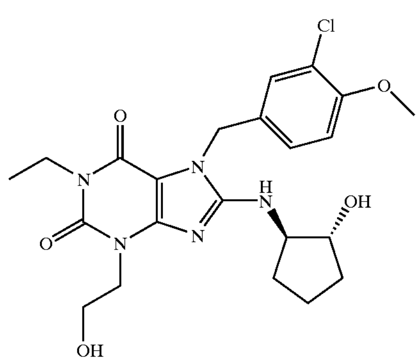 | 478.1857 | 478.1851 | (M + 1) |

TABLE II-continued

| Compound No. | STRUCTURE | HRMS Calc. | HRMS Found | M, M + 1 |
|---|---|---|---|---|
| 107 | 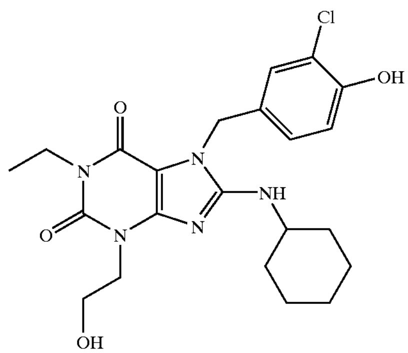 | 462.1908 | 462.191 | (M + 1) |
| 108 | 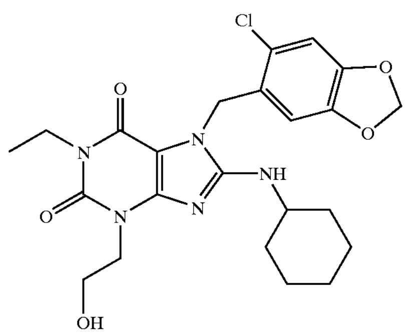 | 490.1857 | 490.1853 | (M + 1) |
| 109 | 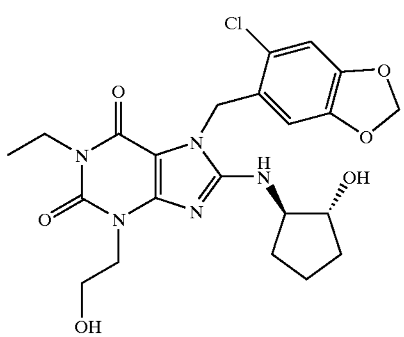 | 492.1650 | 492.1641 | (M + 1) |
| 110 | 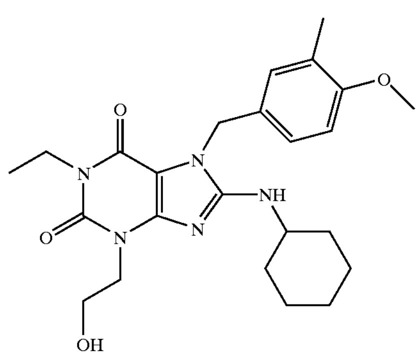 | 455.2533 | 455.2518 | (M+) |

TABLE II-continued

| Compound No. | STRUCTURE | HRMS Calc. | HRMS Found | M, M + 1 |
|---|---|---|---|---|
| 111 | 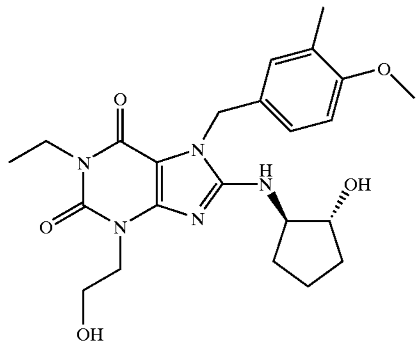 | 458.2403 | 458.2395 | (M + 1) |
| 112 | 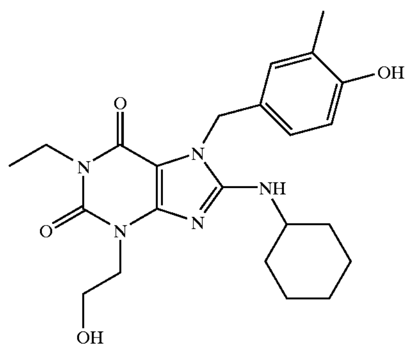 | 442.2454 | 442.2448 | (M + 1) |
| 113 | 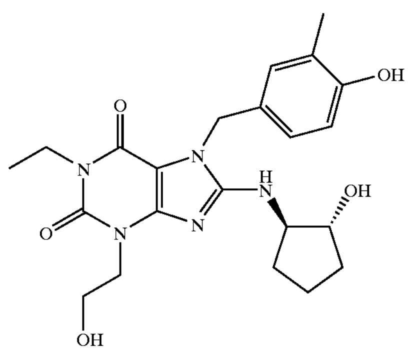 | 444.2247 | 444.2252 | (M + 1) |
| 114 | 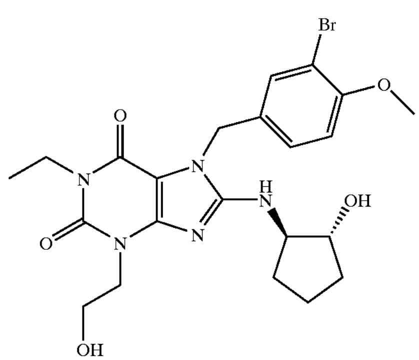 | 522.1352 | 522.1346 | (M + 1) |

TABLE II-continued
| Compound No. | STRUCTURE | HRMS Calc. | HRMS Found | M, M + 1 |
|---|---|---|---|---|
| 115 | 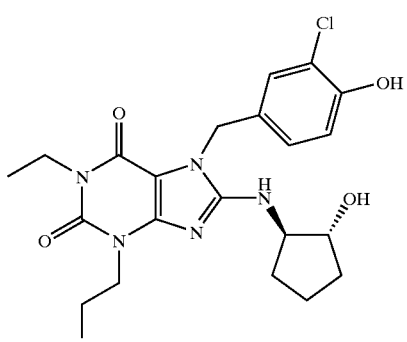 | 464.1701 | 464.1696 | (M + 1) |
| 116 | 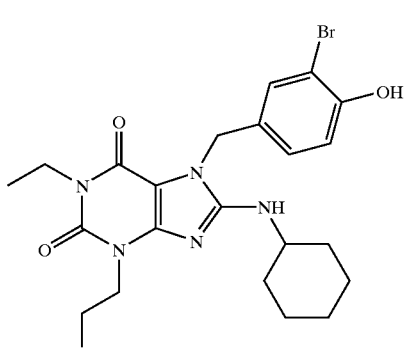 | 506.1403 | 506.141 | (M + 1) |
| 117 | 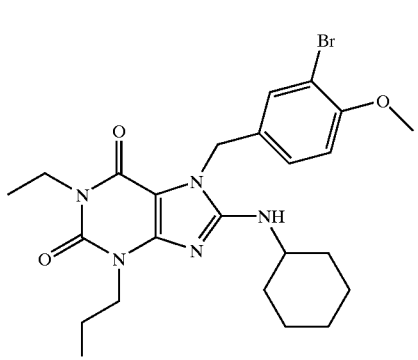 | 520.1559 | 520.1568 | (M + 1) |
| 118 | 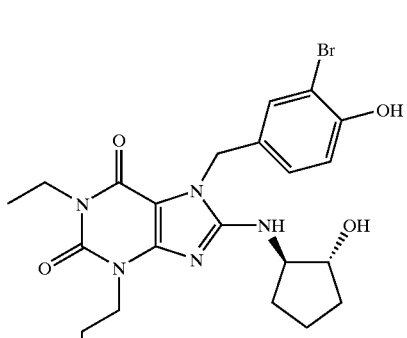 | 508.1196 | 508.119 | (M + 1) |

TABLE II-continued

| Compound No. | STRUCTURE | HRMS Calc. | HRMS Found | M, M + 1 |
|---|---|---|---|---|
| 119 | 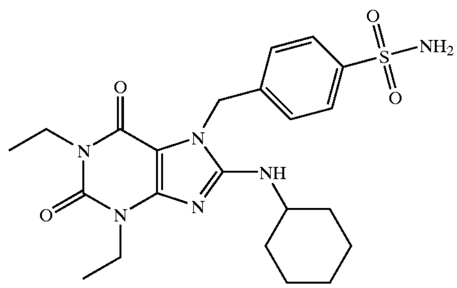 | 475.2128 | 475.2134 | (M + 1) |
| 120 | 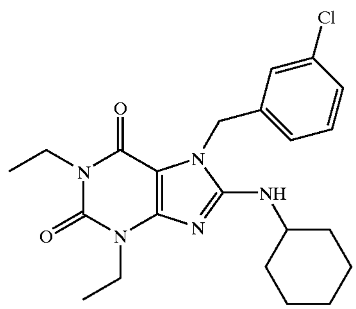 | 429.1932 | 429.1931 | (M+) |
| 121 | 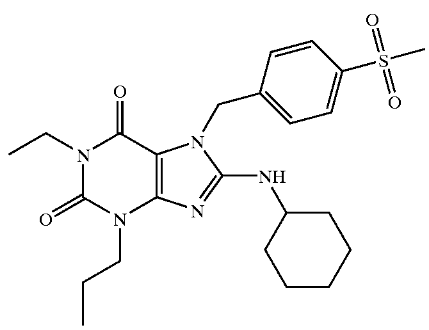 | 488.2332 | 488.2333 | (M + 1) |
| 122 | 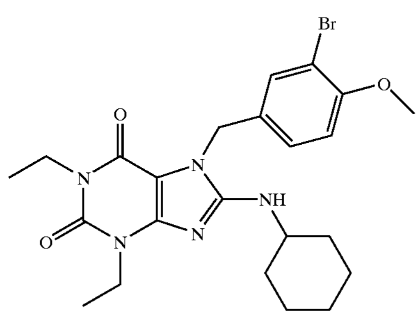 | 504.1610 | 504.1605 | (M + 1) |
| 123 | 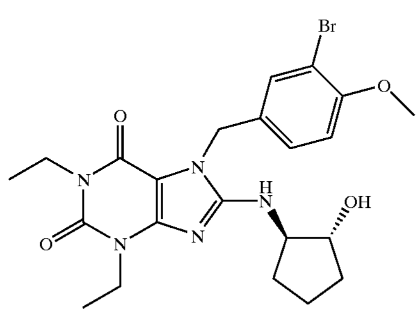 | 506.1403 | 506.1395 | (M + 1) |

TABLE II-continued

| Compound No. | STRUCTURE | HRMS Calc. | HRMS Found | M, M + 1 |
|---|---|---|---|---|
| 124 | 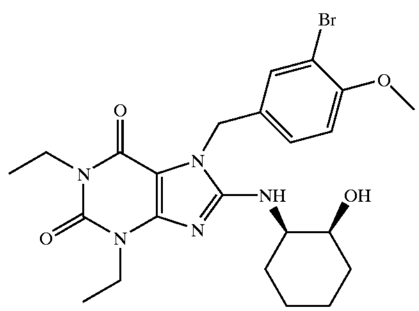 | 522.1542 | 522.1542 | (M + 1) |
| 125 | 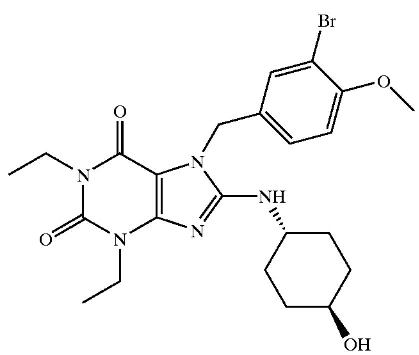 | 520.1559 | 520.1552 | (M + 1) |
| 126 | 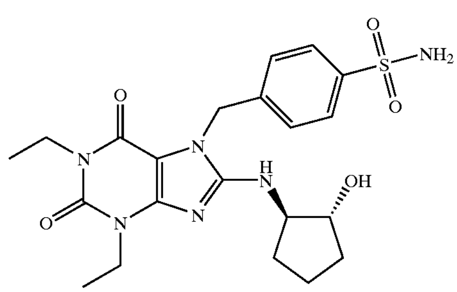 | 477.1920 | 477.1919 | (M + 1) |
| 127 | 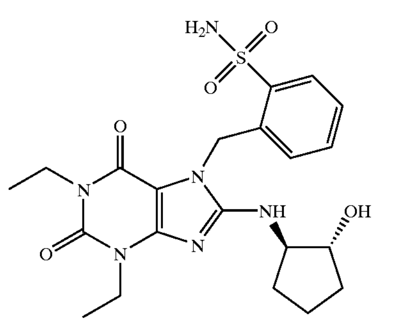 | 477.1920 | 477.1914 | (M + 1) |

TABLE II-continued

| Compound No. | STRUCTURE | HRMS Calc. | HRMS Found | M, M + 1 |
|---|---|---|---|---|
| 128 | 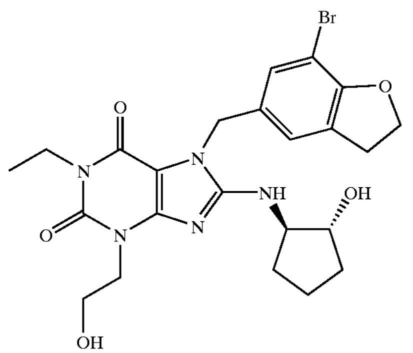 | 536.1335 | 536.1335 | (M + 1) |
| 129 | 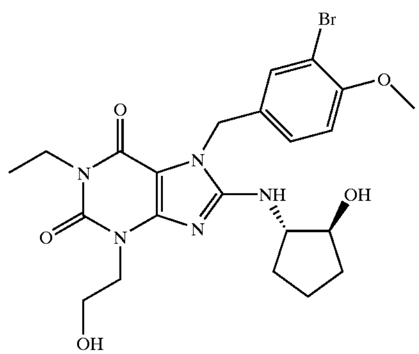 | 522.1352 | 522.136 | (M + 1) |
| 130 | no structure | n/a | n/a | n/a |
| 131 | 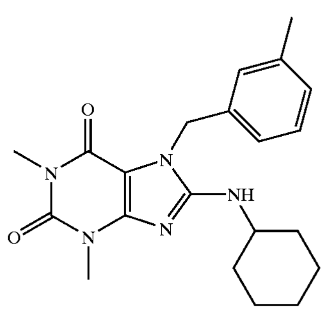 | 382.2243 | 382.2242 | (M + 1) |
| 132 | 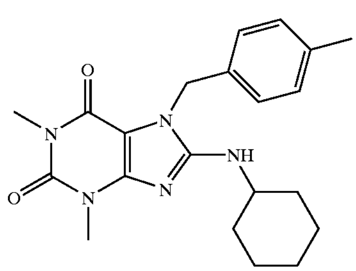 | 382.2243 | 382.2238 | (M + 1) |

TABLE II-continued
| Compound No. | STRUCTURE | HRMS Calc. | HRMS Found | M, M + 1 |
|---|---|---|---|---|
| 133 | 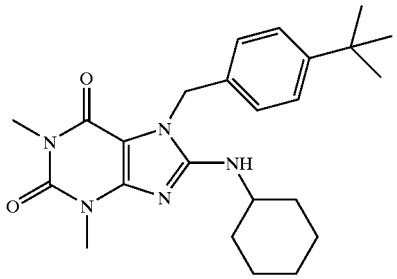 | 424.2713 | 424.2717 | (M + 1) |
| 134 | 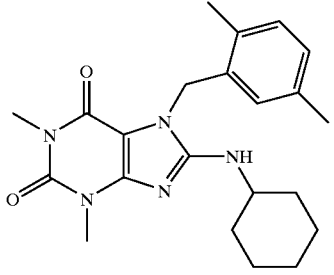 | 396.2400 | 396.2396 | (M + 1) |
| 135 | 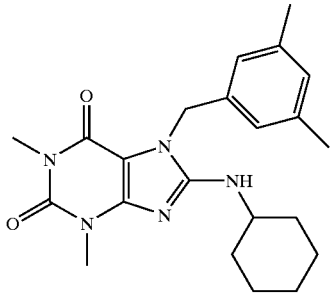 | 396.2400 | 396.2393 | (M + 1) |
| 136 | 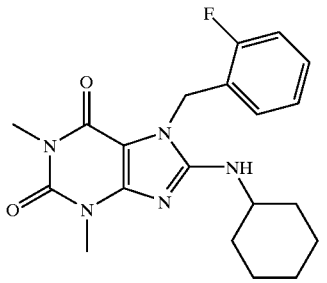 | 386.1992 | 386.1988 | (M + 1) |
| 137 | 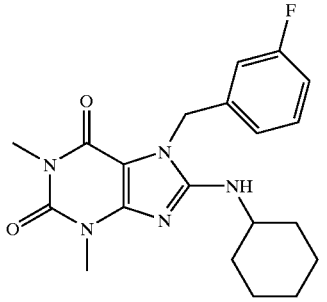 | 386.1992 | 386.1988 | (M + 1) |

TABLE II-continued

| Compound No. | STRUCTURE | HRMS Calc. | HRMS Found | M, M + 1 |
|---|---|---|---|---|
| 138 | 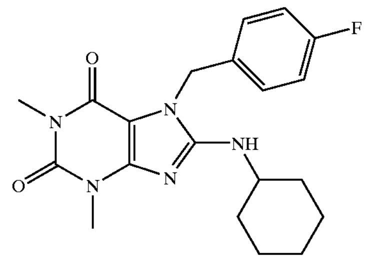 | 386.1992 | 386.1985 | (M + 1) |
| 139 | 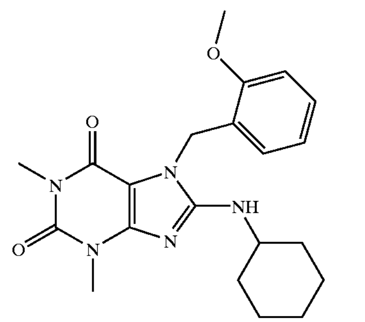 | 398.2192 | 398.2196 | (M + 1) |
| 140 | 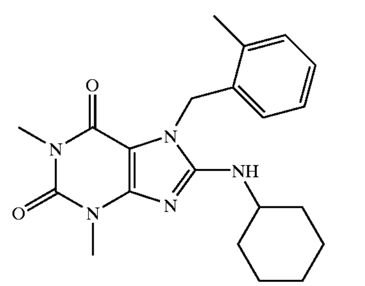 | 382.2243 | 382.2238 | (M + 1) |
| 141 | 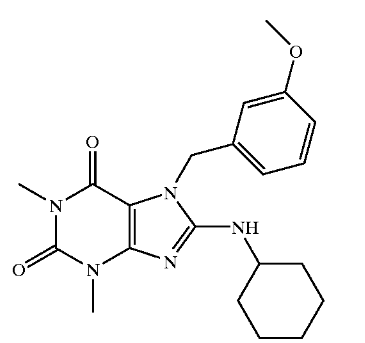 | 398.2192 | 398.2192 | (M + 1) |
| 142 | 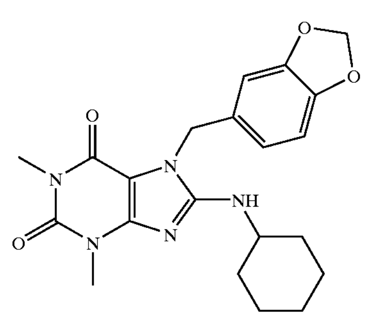 | 412.1985 | 412.1982 | (M + 1) |

TABLE II-continued

| Compound No. | STRUCTURE | HRMS Calc. | HRMS Found | M, M + 1 |
|---|---|---|---|---|
| 143 | 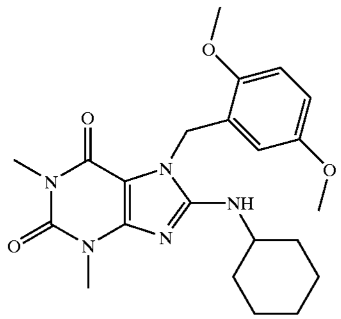 | 428.2298 | 428.2294 | (M + 1) |
| 144 | 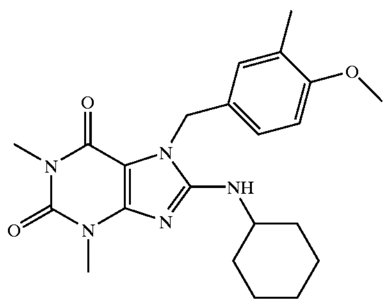 | 412.2349 | 412.2346 | (M + 1) |
| 145 | 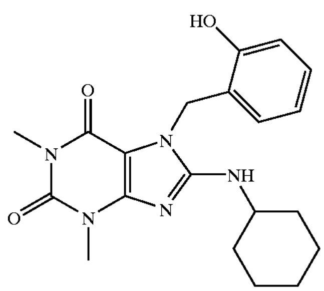 | 384.2036 | 384.2041 | (M + 1) |
| 146 | 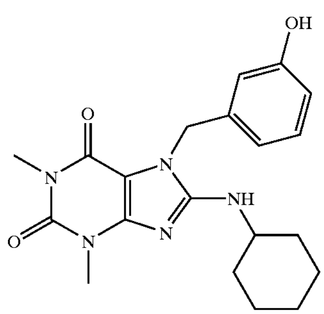 | 384.2036 | 384.2033 | (M + 1) |
| 147 | 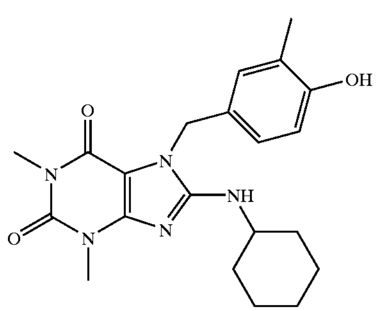 | 398.2192 | 398.2184 | (M + 1) |

TABLE II-continued

| Compound No. | STRUCTURE | HRMS Calc. | HRMS Found | M, M + 1 |
|---|---|---|---|---|
| 148 | 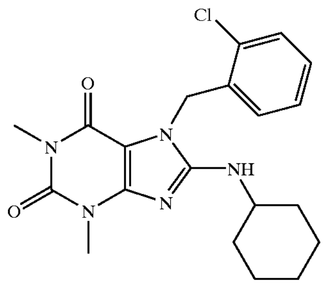 | 402.1697 | 402.1691 | (M + 1) |
| 149 | 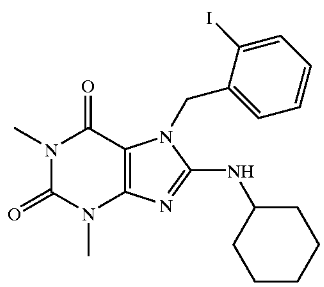 | 493.0975 | 493.098 | (M+) |
| 150 | 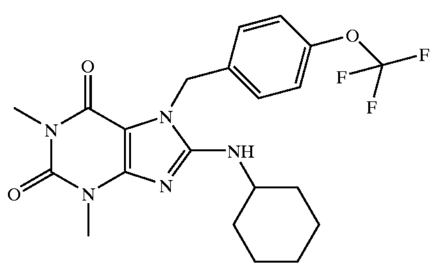 | 451.1831 | 451.1819 | (M+) |
| 151 | 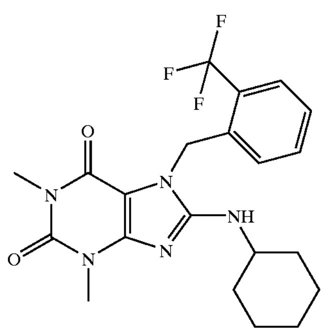 | 435.1882 | 435.1879 | (M+) |
| 152 | 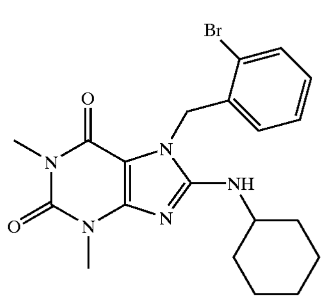 | 446.1192 | 446.1187 | (M + 1) |

TABLE II-continued

| Compound No. | STRUCTURE | HRMS Calc. | HRMS Found | M, M + 1 |
|---|---|---|---|---|
| 153 | 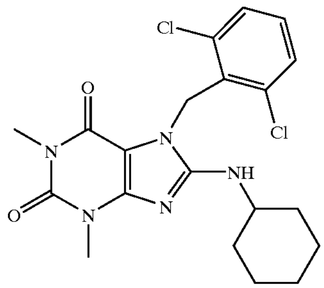 | 435.1229 | 435.1219 | (M+) |
| 154 | 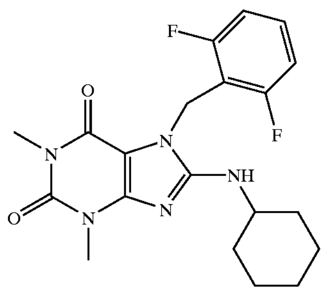 | 404.1898 | 404.1895 | (M + 1) |
| 155 | 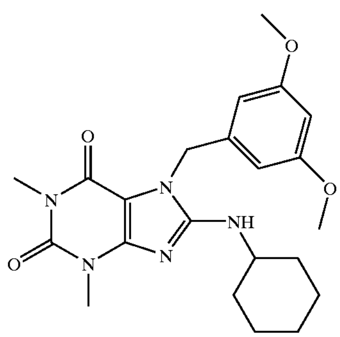 | 428.2298 | 428.2292 | (M + 1) |
| 156 | 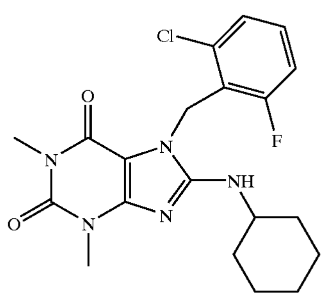 | 420.1603 | 420.1603 | (M + 1) |
| 157 | 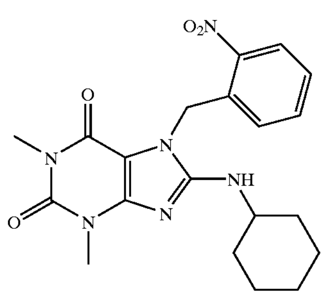 | 413.1937 | 413.1932 | (M + 1) |

TABLE II-continued
| Compound No. | STRUCTURE | HRMS Calc. | HRMS Found | M, M + 1 |
|---|---|---|---|---|
| 158 | 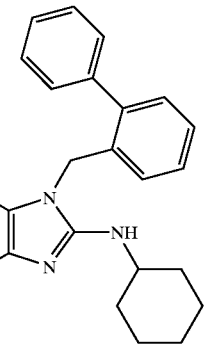 | 444.2400 | 444.2394 | (M + 1) |
| 159 | 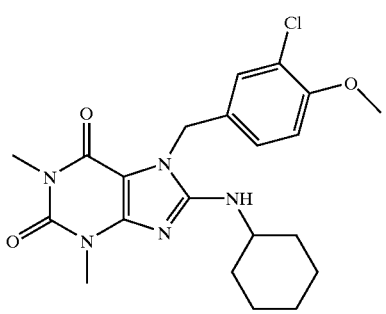 | 431.1724 | 431.173 | (M+) |
| 160 | 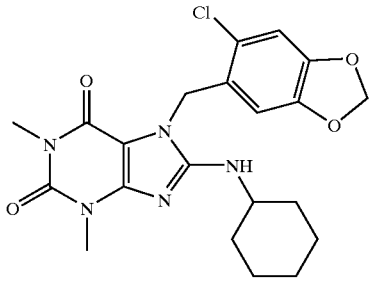 | 446.1595 | 446.1588 | (M + 1) |
| 161 | 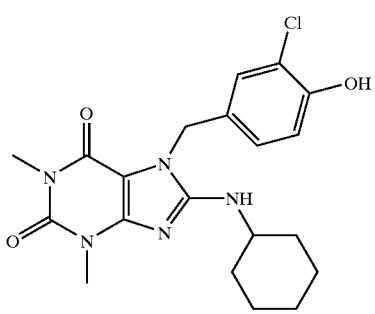 | 418.1646 | 418.164 | (M + 1) |
| 162 | 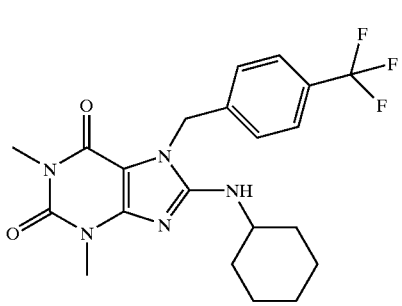 | 436.1960 | 436.1962 | (M + 1) |

TABLE II-continued
| Compound No. | STRUCTURE | HRMS Calc. | HRMS Found | M, M + 1 |
|---|---|---|---|---|
| 163 | 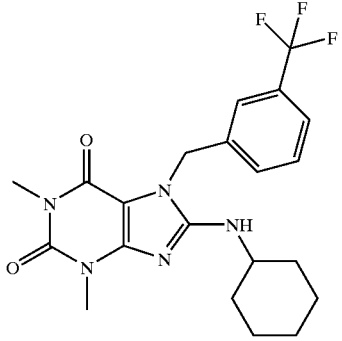 | 436.1960 | 436.1957 | (M + 1) |
| 164 | 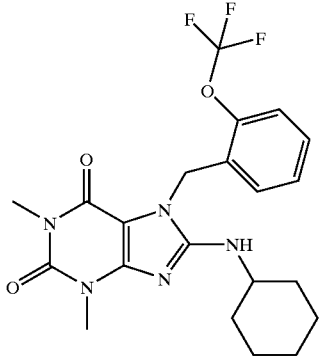 | 452.1909 | 452.1919 | (M + 1) |
| 165 | 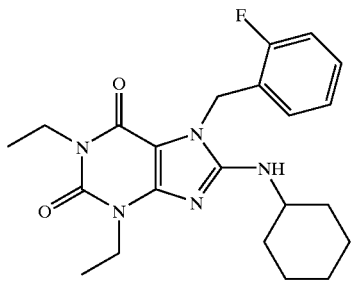 | 414.2305 | 414.2303 | (M + 1) |
| 166 | 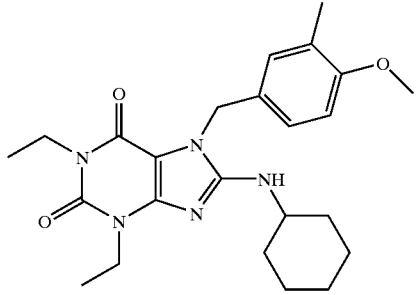 | 440.2662 | 440.2657 | (M + 1) |

TABLE II-continued

| Compound No. | STRUCTURE | HRMS Calc. | HRMS Found | M, M + 1 |
|---|---|---|---|---|
| 167 | 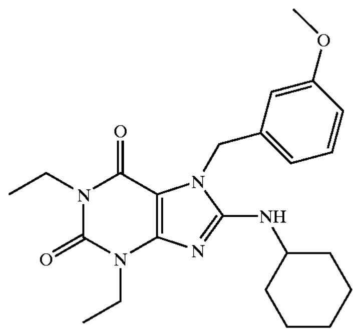 | 426.2505 | 426.2509 | (M + 1) |
| 168 | 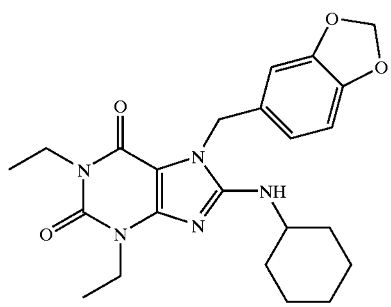 | 440.2298 | 440.2295 | (M + 1) |
| 169 | 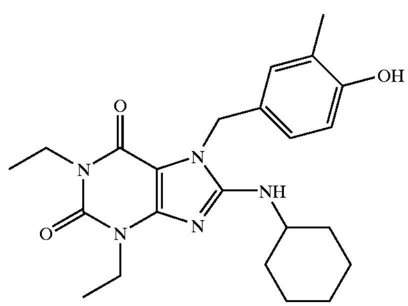 | 426.2505 | 426.2498 | (M + 1) |
| 170 | 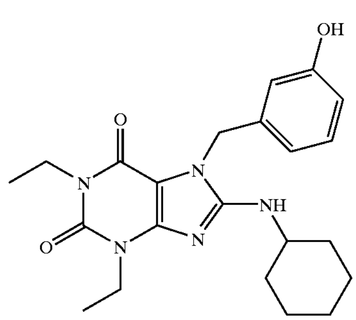 | 412.2349 | 412.2345 | (M + 1) |

TABLE II-continued

| Compound No. | STRUCTURE | HRMS Calc. | HRMS Found | M, M + 1 |
|---|---|---|---|---|
| 171 | 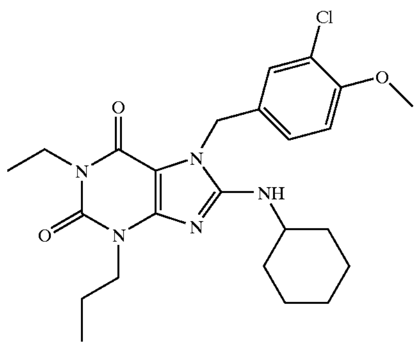 | 474.2272 | 474.2277 | (M + 1) |
| 172 | 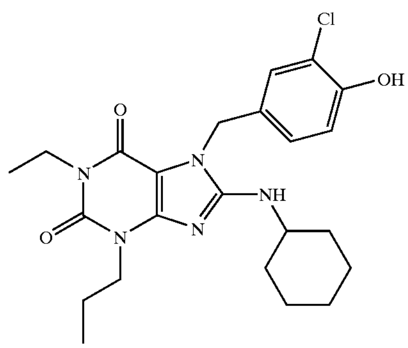 | 459.2037 | 459.2055 | (M+) |
| 173 | 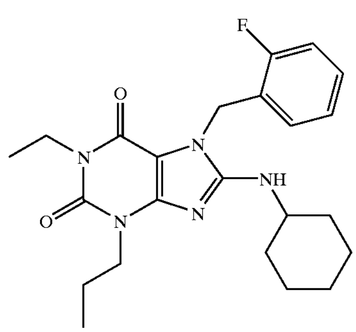 | 428.2462 | 428.2457 | (M + 1) |
| 174 | 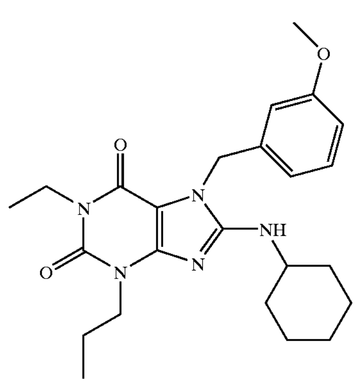 | 440.2662 | 440.2657 | (M + 1) |

TABLE II-continued

| Compound No. | STRUCTURE | HRMS Calc. | HRMS Found | M, M + 1 |
|---|---|---|---|---|
| 175 | 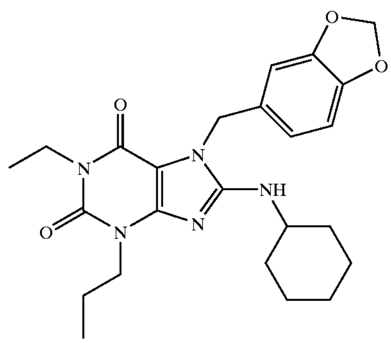 | 454.2454 | 454.2449 | (M + 1) |
| 176 | 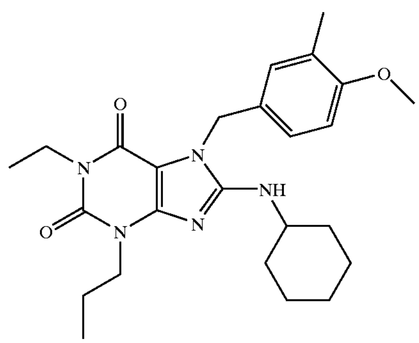 | 454.2818 | 454.2812 | (M + 1) |
| 177 | 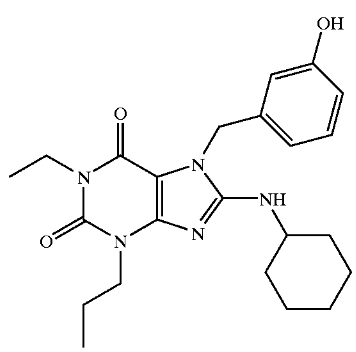 | 426.2505 | 426.2503 | (M + 1) |
| 178 | 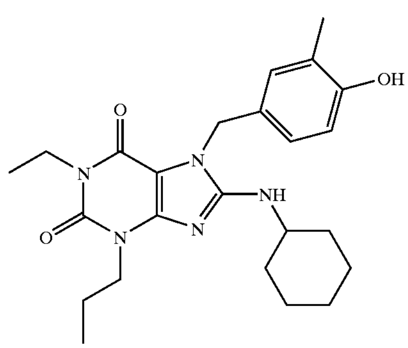 | 440.2662 | 440.2666 | (M + 1) |

TABLE II-continued

| Compound No. | STRUCTURE | HRMS Calc. | HRMS Found | M, M + 1 |
|---|---|---|---|---|
| 179 | 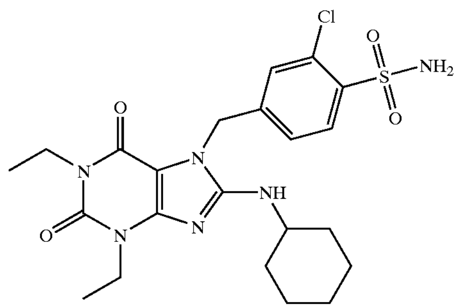 | 509.1738 | 509.1729 | (M + 1) |
| 180 | 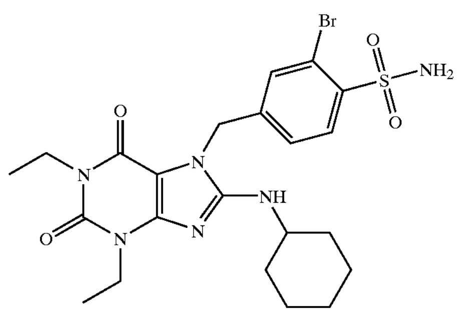 | 555.1233 | 555.123 | (M + 1) |
| 181 | 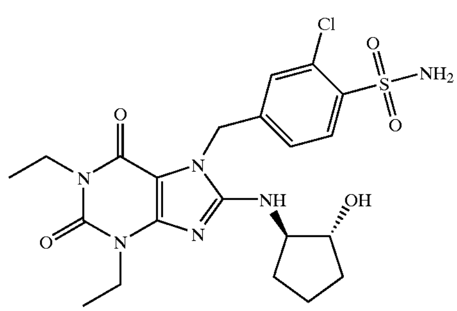 | 511.153 | 511.1524 | (M + 1) |
| 182 | 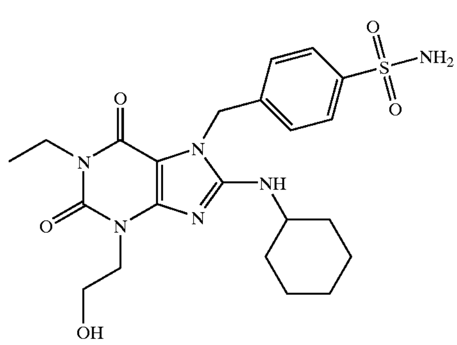 | 491.2077 | 491.2087 | (M + 1) |

TABLE II-continued

| Compound No. | STRUCTURE | HRMS Calc. | HRMS Found | M, M + 1 |
|---|---|---|---|---|
| 183 | 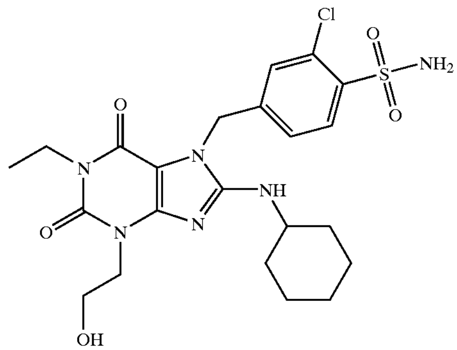 | 525.1687 | 525.1697 | (M + 1) |
| 184 | 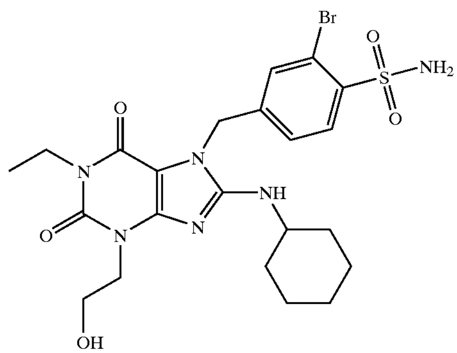 | 571.1164 | 571.1138 | (M + 1) |
| 185 | 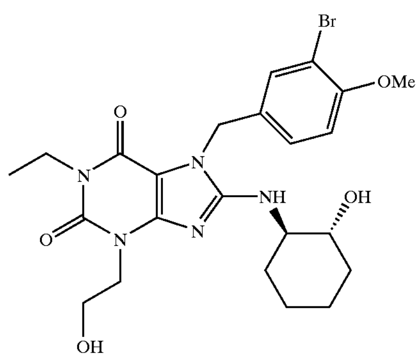 | 538.1492 | 538.1498 | (M + 1) |
| 186 | 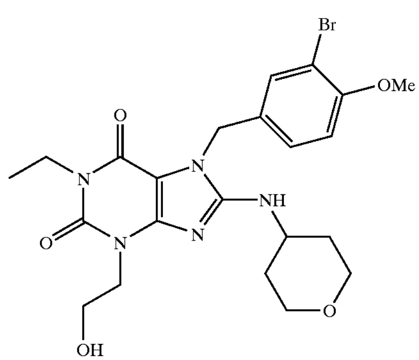 | 524.1335 | 524.1344 | (M + 1) |

TABLE II-continued

| Compound No. | STRUCTURE | HRMS Calc. | HRMS Found | M, M + 1 |
|---|---|---|---|---|
| 187 | 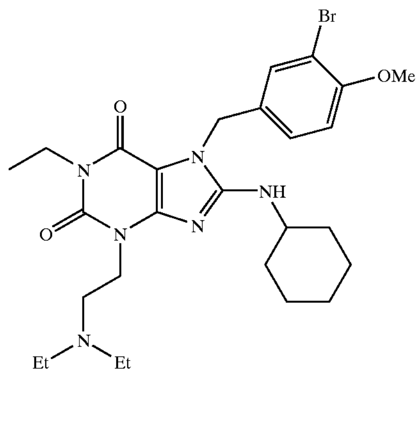 | 575 | 575 | (M) LRMS |
| 188 | 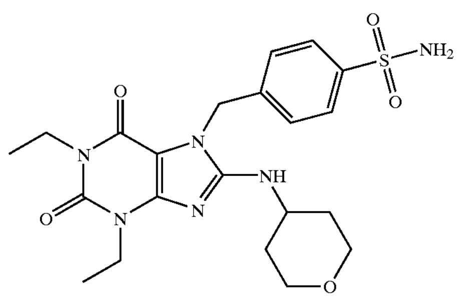 | 477.192 | 477.1919 | (M + 1) |
| 189 | 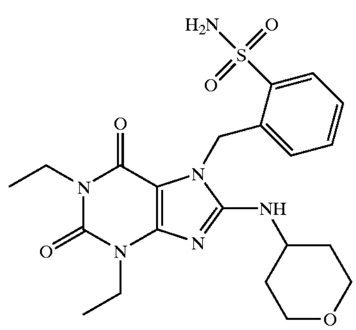 | 477.192 | 477.1919 | (M + 1) |
| 190 | 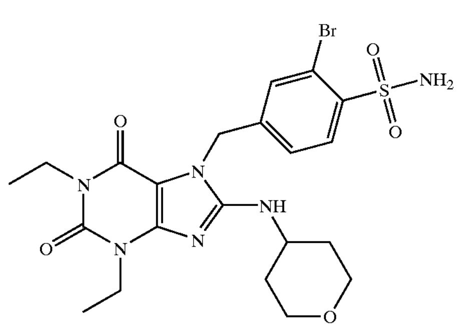 | 557.1007 | 557.0997 | (M + 1) |

TABLE II-continued

| Compound No. | STRUCTURE | HRMS Calc. | HRMS Found | M, M + 1 |
|---|---|---|---|---|
| 191 | 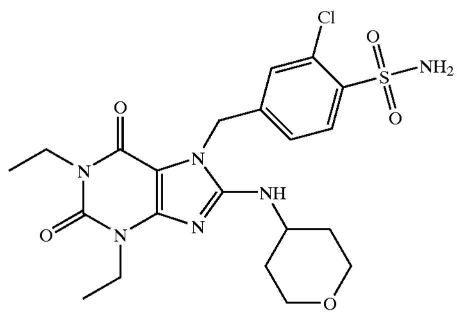 | 511.153 | 511.1519 | (M + 1) |
| 192 | 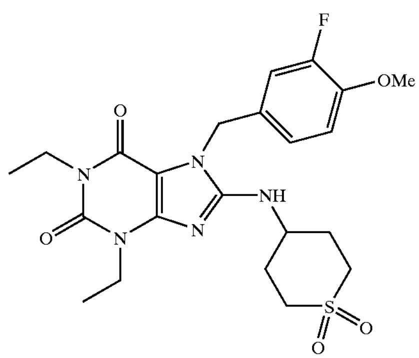 | 494.1637 | 494.1636 | (M + 1) |
| 193 | 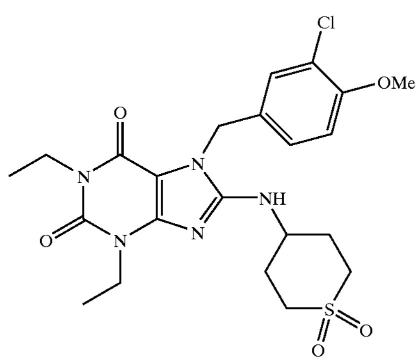 | 510.1578 | 510.1574 | (M + 1) |
| 194 | 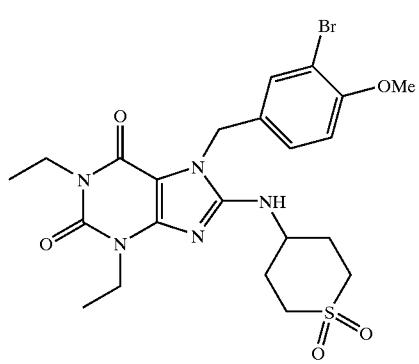 | 554.1073 | 554.1066 | (M + 1) |

TABLE II-continued
| Compound No. | STRUCTURE | HRMS Calc. | HRMS Found | M, M + 1 |
|---|---|---|---|---|
| 195 | 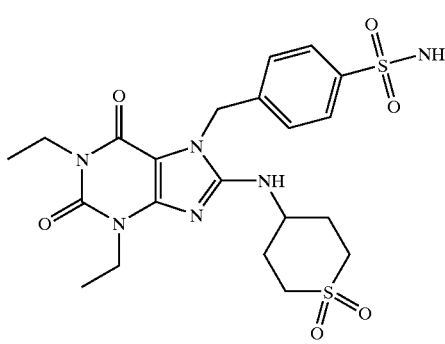 | 525.159 | 525.1582 | (M + 1) |
| 196 | 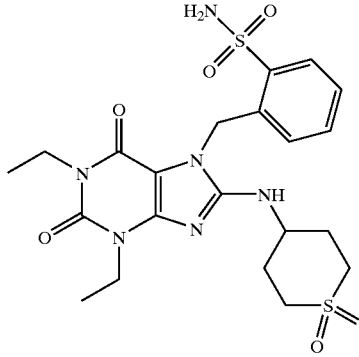 | 525.159 | 525.1597 | (M + 1) |
| 197 | 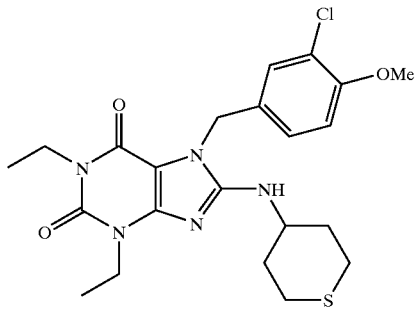 | 478.168 | 478.1683 | (M + 1) |
| 198 | 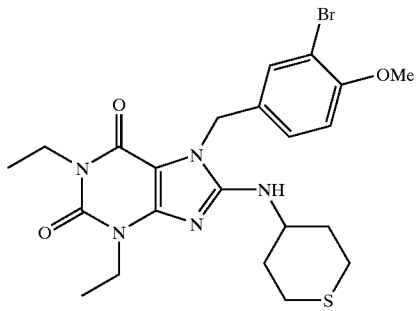 | 522.1174 | 522.1169 | (M + 1) |

TABLE II-continued

| Compound No. | STRUCTURE | HRMS Calc. | HRMS Found | M, M + 1 |
|---|---|---|---|---|
| 199 | 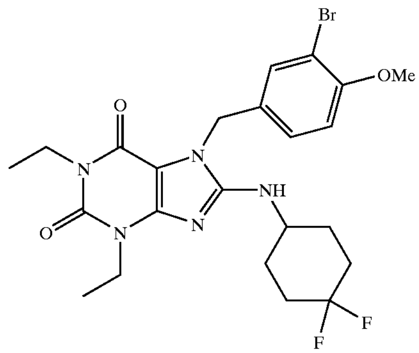 | 542.1405 | 542.143 | (M + 1) |

The compounds of the invention are useful for inhibiting PDE V enzymes. Their enzyme activities and enzyme selectivities can be evaluated in a number of ways. In particular, enzyme activity can be measured by the PDE V $IC_{50}$ value, which is the concentration (in nM) of the compound required to provide 50% inhibition of PDE V. The lower the value of $IC_{50}$, the more active is the compound. Measurements on the compounds in Tables I and II gave the following data (all numbers are modified by the word "about"):

- A. all compounds had a PDE V $IC_{50}$ within the range of from <1 nM to >100 nM;
- B. compound nos. 13–18, 25, 30–32, 38, 41–43, 55–58, 69–71, 77, 85, 92, 96, 98, 101, 113, 120, 121, 126, 128, 131, 137, 138, 141, 146–48, 165, 166, 173, 176, 181, 182, 184, 185, 193 and 194 had a PDE V $IC_{50}$ within the range of from >15 to 100 nM;
- C. compound nos. 23, 24, 29, 33, 34, 39, 40, 93, 94, 108, 111, 112, 125, 136, 144, 160 and 161 had a PDE V $IC_{50}$ within the range of from >10 to 15 nM.
- D. compound nos. 21, 22, 28, 36, 37, 59, 66, 68, 78, 79, 89, 95, 99, 110, 115, 132, 159, 171, 172, 175, 180, 183, 190 and 199 had a PDE V $IC_{50}$ within the range of from >5 to 10 nM; and
- E. compound nos. 60–65, 67, 103–07, 114, 116–19, 122–24, 142, 168–70, 177, 178, 179, 186–88, 191, 197 and 198 had a PDE V $IC_{50}$ within the range of up to 5 nM.

In addition, another type of measurement that can be made is the ratio of PDE VI $IC_{50}$/PDE V $IC_{50}$ (identified as "PDE VI/PDE V"), which is an indicator of enzyme selectivity—the higher the ratio, the more selective is the compound to inhibiting PDE V enzyme relative to PDE VI enzyme. Measurements on the compounds (except for compound nos. 189, 192, 195 and 196) in Table II gave the following data (all numbers are modified by the word "about"):

- F. compound nos. 1–188, 190, 191, 193, 194 and 197–99 had a PDE VI/PDE V ratio of >0;
- G. compound nos. 165 and 193 had a PDE VI/PDE V ratio within the range of from >0 to 10;
- H. compound nos. 101, 108, 136, 141, 146, 148, 168, 173 and 194 had a PDE VI PDE V ratio within the range of from >10 to 25;
- I. compound nos. 104, 125, 131–32, 137–38, 142, 144, 170, 175, 177, 185 and 199 had a PDE VI/PDE V ratio within the range of from >25 to 50;
- J. compound nos. 103, 110, 111, 117, 159, 166, 182 and 187 had a PDE VI/PDE V ratio within the range of from >50 to 75;
- K. compound nos. 105, 106, 147 and 171 had a PDE VI/PDE V ratio within the range of from >75 to 100;
- L. compound nos. 112, 113, 123, 124, 126, 169, 172 and 184 had a PDE VI/PDE V ratio within the range of from >100 to 140; and
- M. compound nos. 107, 114–16, 118–22, 128, 160–61, 176, 178–81, 183, 186, 188, 190, 191, 197 and 198 had a PDE VI/PDE V ratio of from >140.

Preferred compounds of the invention include those found in classes E and/or M: compound nos. 60–65, 67, 103–07, 114–24, 128, 142, 160–61, 168–70, 176–78, 179, 186, 188, 191, 197 and 198. More preferred compounds of the invention are compound nos. 107, 114, 116, 118, 119, 122, 160, 178 and 186 of Table II.

Another preferred compound of the invention would have the following chemical structure:

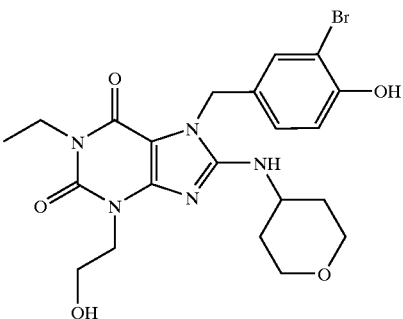

Specific and general procedures for producing three preferred compounds follow below (compound nos. 107, 114 and 160). Obvious modifications to these procedures may be undertaken by one of ordinary skill in the art. Other compounds of the invention may be produced along the same lines.

Synthesis of Compound No. 107 in Table II (7)

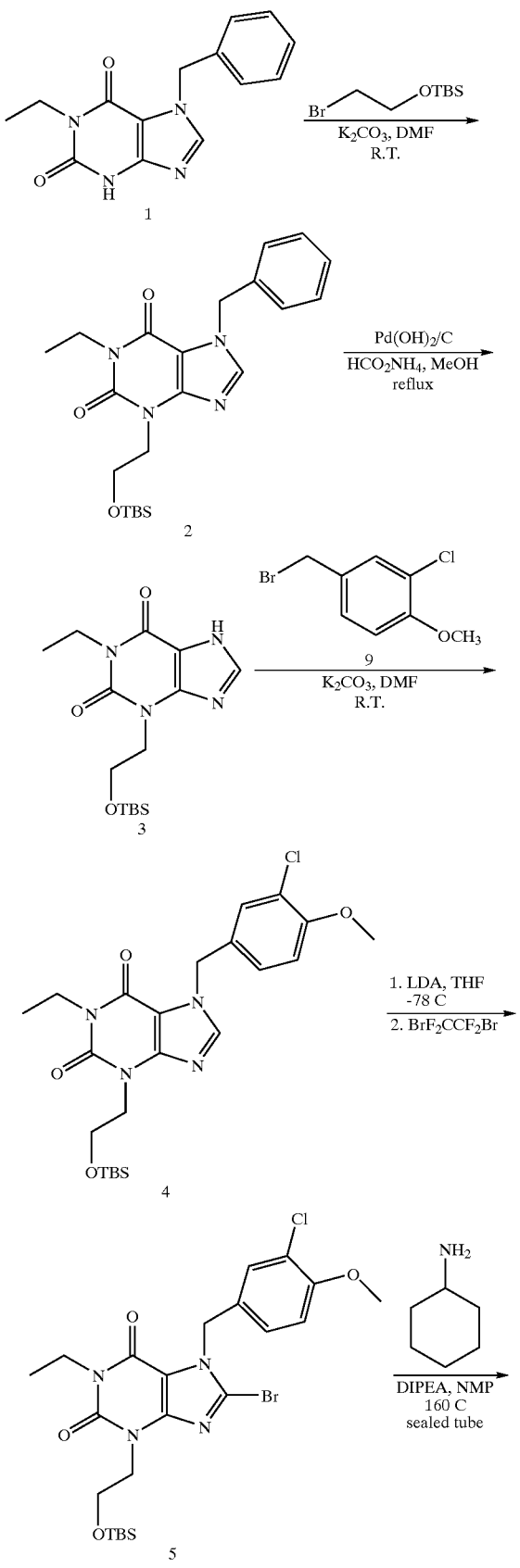

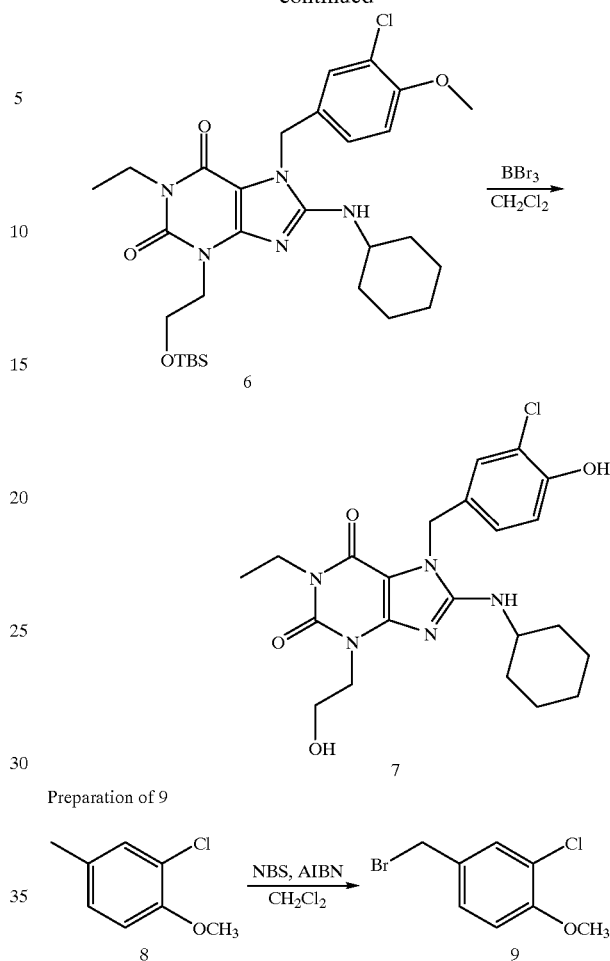

EXPERIMENTAL PROCEDURE

Compound No. 107 in Table II (7)

1 (20.0 g, 74.0 mmol) was dissolved in dimethylformamide (370 mL) under nitrogen and (2-bromoethoxy)-tert-butyldimethylsilane (31.8 mL, 148 mmol) was added dropwise. The reaction was stirred at room temperature for 115 hrs., then diluted with ethyl acetate and washed with water several times. The organic mixture was dried over potassium carbonate, filtered and concentrated under vacuum. Purification via flash chromatography (30/70 ethyl acetate/hexanes) yielded 2 (28.1 g, 88%).

$^1$H NMR (400 MHz, CDCl$_3$): δ 7.52 (s, 1H), 7.29–7.39 (m, 5H), 5.49 (s, 2H), 4.25 (t, 2H, J=6.0 Hz), 4.07 (q, 2H, J=7.2 Hz), 3.93 (t, 2H, J=6.0 Hz), 1.24 (t, 3H, J=7.2 Hz), 0.75 (s, 9H), 0.08 (s, 6H). HRMS: Calcd for C$_{22}$H$_{32}$N$_4$O$_3$Si (M+H): 429.2322. Found: 429.2329.

To a solution of 2 (2.10 g, 4.89 mmol) in methanol (375 mL) was added ammonium formate (4.64 g, 73.6 mmol) and 20% palladium hydroxide on carbon (980 mg). The reaction was heated to reflux for 1.5 hrs., then cooled to room temperature, filtered and concentrated under vacuum. Purification via flash chromatography (50/50 ethyl acetate/hexanes) yielded 3 (1.26 g, 94%).

$^1$H NMR (400 MHz, CDCl$_3$): δ 7.82 (s, 1H), 4.33 (t, 2H, J=6.0 Hz), 4.16 (q, 2H, J=7.2 Hz), 3.99 (t, 2H, J=6.0 Hz), 1.29 (t, 3H, J=7.2 Hz), 0.78 (s, 9H), 0.06 (s, 6H). HRMS: Calcd for C$_{15}$H$_{26}$N$_4$O$_3$Si(M+H): 339.1852. Found: 339.1864.

To 3 (970 mg, 2.86 mmol) was added dimethylformamide (14 mL), 3-chloro-4-methoxybenzyl bromide 9 (1.72 g, 5.70 mmol), and potassium carbonate (785 mg, 5.70 mmol) under nitrogen. The reaction mixture was stirred at room temperature for 24 hrs., then diluted with ethyl acetate and washed with water several times. The organic mixture was dried over potassium carbonate, filtered and concentrated under vacuum. Purification by flash chromatography (30/70 ethyl acetate/hexanes) yielded 4 (1.14 g, 81%).

$^1$H NMR (400 MHz, CDCl$_3$): δ 7.52 (s, 1H), 7.33 (d, 1H, J=2.4 Hz), 7.25 (dd 1H, J=2.0 Hz, J=8.4 Hz), 6.90 (d, 1H, J=8.8 Hz), 5.40 (s, 2H), 4.25 (t, 2H, J=6.0 Hz), 4.07 (q, 2H, J=7.2 Hz), 3.93 (t, 2H, J=6.0 Hz), 3.89 (s, 3H), 1.25 (t, 3H, J=7.2 Hz), 0.75 (s, 9H), 0.08 (s, 6H). HRMS: Calcd for C$_{23}$H$_{33}$ClN$_4$O$_4$Si(M+H): 493.2038. Found: 493.2032.

To solution of 4 (1.14 g, 2.32 mmol) in tetrahydrofuran (20 mL) under nitrogen at −78° C. (dry ice/acetone bath) was added lithium diisopropylamide (2M in THF/heptane, 1.7 mL, 3.48 mmol). After stirring for thirty minutes, 1,2-dibromotetrafluoroethane (0.55 mL, 4.63 mmol) was added dropwise over five minutes. The reaction was stirred for 1.5 hrs. at −78° C. then quenched with saturated aqueous sodium bicarbonate and warmed to room temperature. The mixture was extracted with dichloromethane, dried over potassium carbonate, filtered and concentrated under vacuum. Purification via flash chromatography (30/70 ethyl acetate/hexanes) yielded 5 (640 mg, 48%).

$^1$H NMR (400 MHz, CDCl$_3$): δ 7.42 (d, 1H, J=2.4 Hz), 7.31 (dd, 1H, J=2.0 Hz, J=8.4 Hz), 6.88 (d, 1H, J=8.8 Hz), 5.45 (s, 2H), 4.22 (t, 2H, J=5.6 Hz), 4.07 (q, 2H, J=7.2 Hz), 3.92 (t, 2H, J=5.6 Hz), 3.88 (s, 3H), 1.25 (t, 3H, J=7.2 Hz), 0.74 (s, 9H), 0.08 (s, 6H). HRMS: Calcd for C$_{23}$H$_{32}$BrClN$_4$O$_4$Si(M+H): 571.1143. Found: 571.1149.

To 5 (320 mg, 0.56 mmol) was added cyclohexylamine (0.25 mL, 2.24 mmol), diisopropylethylamine (2.8 mL), and 1-methyl-2-pyrrolidinone (2.8 mL). The reaction mixture was heated to 160° C. in a sealed tube for 18 hrs., then cooled to room temperature. Water was added, then the mixture was extracted with ethyl acetate and washed with water several times. The organic mixture was dried over potassium carbonate, filtered and concentrated under vacuum. Purification via flash chromatography (30/70 ethyl acetate/hexanes) yielded 6 (210 mg, 64%).

$^1$H NMR (400 MHz, CDCl$_3$): δ 7.27 (d, 1H, J=2.0 Hz), 7.13 (dd, 1H, J=2.0 Hz, J=8.4 Hz), 6.89 (d, 1H, J=8.8 Hz), 5.23 (s, 2H), 4.19 (t, 2H, J=6.2 Hz), 4.05 (q, 2H, J=7.2 Hz), 3.93 (t, 2H, J=6.2 Hz), 3.89 (s, 3H), 3.86–3.91 (m, 1H), 3.69–3.80 (m, 1H), 1.88–1.96 (m, 2H), 1.52–164(m, 3H), 1.28–1.42 (m, 2H), 1.23 (t, 3H, J=7.2 Hz), 1.04–1.22 (m, 3H), 0.81 (s, 9H), 0.01 (s, 6H). HRMS: Calcd for C$_{29}$H$_{44}$ClN$_5$O$_4$Si (M+H): 590.2937. Found: 590.2929.

6 (191 mg, 0.324 mmol) was dissolved in dichloromethane (4.0 mL) under nitrogen and cooled to 0° C. in an ice bath. Boron tribromide (0.14 mL, 1.42 mmol) was added to the reaction mixture and warmed to room temperature. After 1.25 hr., the reaction was diluted with dichloromethane and washed with water several times. The organic phase was dried over potassium carbonate, filtered and concentrated under vacuum. Purification via PTLC (70/30 ethyl acetate/hexanes) yielded 7 (compound no.107 in Table II) (122 mg, 74%).

$^1$H NMR (400 MHz, CDCl$_3$): δ 7.25–7.28 (m, 1H), 7.09 (dd, 1H, J=2.0 Hz, J=8.0 Hz), 7.01 (d, 1H, J=8.0 Hz), 5.69 (s, 1H), 5.23 (s, 2H), 4.32–4.36 (m, 2H), 4.16 (t, 1H, J=6.0Hz), 4.06 (q, 2H, J=7.2Hz), 3.90–3.98 (m, 3H), 3.62–3.72 (m, 1 H), 1.87–1.96 (m, 2H), 1.54–1.66 (m, 3H), 1.31–1.43 (m, 2H), 1.25 (t, 3H, J=7.2 Hz), 1.06–1.22 (m, 3H). HRMS: Calcd for C$_{22}$H$_{28}$ClN$_5$O$_4$ (M+H): 462.1908. Found: 462.1901.

3-Chloro-4-methoxytoluene 8 (2.6 mL, 19.2 mmol) was dissolved in dichlomethane (30 mL) and N-bromosuccinimide (3.75 g, 21.1 mmol) was added followed by AIBN (36.0 mg). The reaction was heated to reflux for 19 hrs., then cooled to room temperature and the precipitate was filtered off. The filtrate was diluted with dichloromethane and washed with 0.5 M aqueous sodium bicarbonate, followed by water. The organic mixture was dried over sodium sulfate, filtered and concentrated under vacuum to yield 9 (4.73 g, 82%). The benzyl bromide was used as the crude material without further purification.

$^1$H NMR (400 MHz, CDCl$_3$): δ 7.42 (d, 1H, J=2.4 Hz), 7.26 (dd, 1H, J=2.4 Hz, J=8.4 Hz), 6.88 (d, 1H, J=8.4 Hz), 4.44 (s, 2H), 3.90 (s, 3H).

General Synthesis of Compound No. 107 in Table II (7)

a) Reacting 1 with an alkyl halide and base to form 2;
b) Debenzylation of 2 to form 3;
c) Alkylation of 3 with a benzyl halide to form 4;
d) Deprotonation of 4 followed by addition of a brominating agent to form 5;
e) Displacement of bromo 5 with an amine to form 6; and
f) Treatment of 6 with boron tribromide to form compound no. 107 in Table II (7) via cleavage of both silyl and methyl ethers.

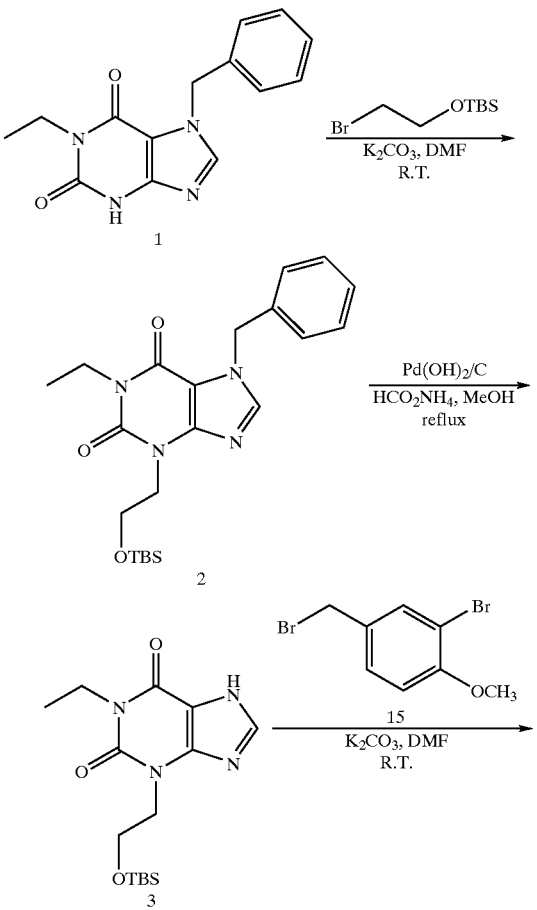

Synthesis of Compound 114 in Table II (13)

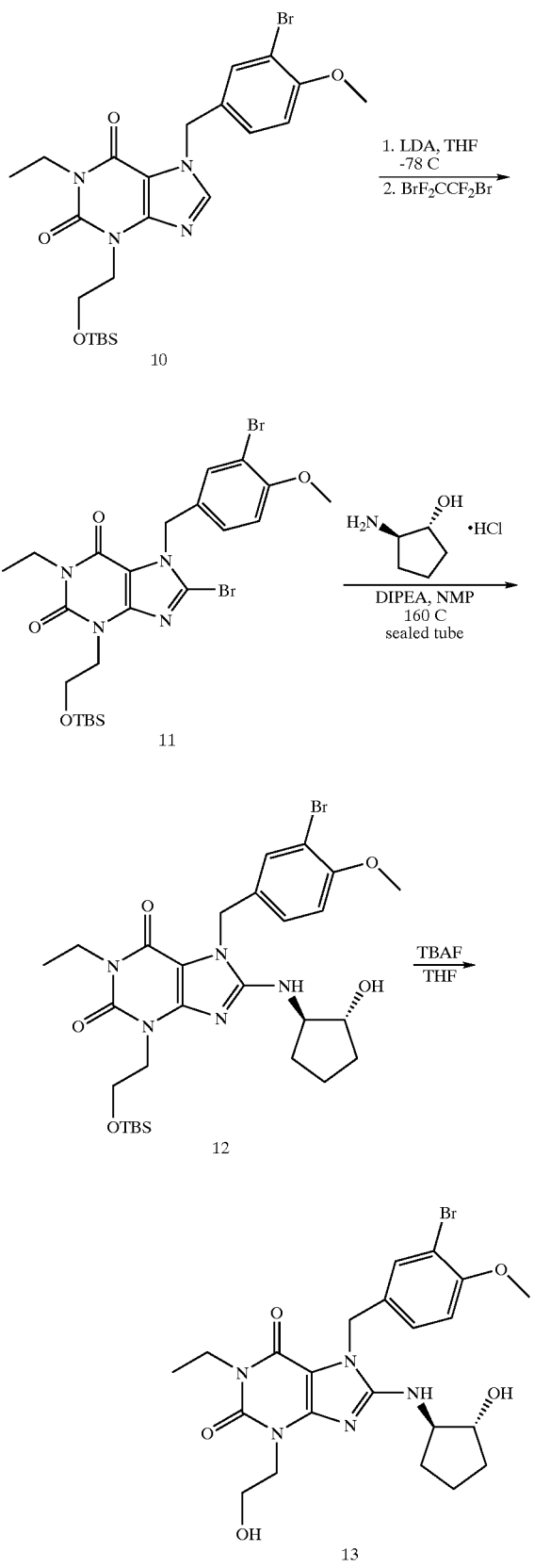

Preparation of 15

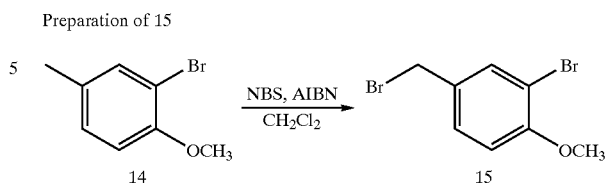

EXPERIMENTAL PROCEDURE

Compound 114 in Table II (13)

1 (20.0 g, 74.0 mmol) was dissolved in dimethylformamide (370 mL) under nitrogen and (2-bromoethoxy)-tert-butyldimethylsilane (31.8 mL, 148 mmol) was added dropwise. The reaction was stirred at room temperature for 115 hrs., then diluted with ethyl acetate and washed with water several times. The organic mixture was dried over potassium carbonate, filtered and concentrated under vacuum. Purification via flash chromatography (30/70 ethyl acetate/hexanes) yielded 2 (28.1 g, 88%).

$^1$H NMR (400 MHz, CDCl$_3$): δ 7.52 (s, 1H), 7.29–7.39 (m, 5H), 5.49 (s, 2H), 4.25 (t, 2H, J6.0 Hz), 4.07 (q, 2H, J=7.2 Hz), 3.93 (t, 2H, J=6.0 Hz), 1.24 (t, 3H, J=7.2 Hz), 0.75 (s, 9H), 0.08 (s, 6H). HRMS: Calcd for C$_{22}$H$_{32}$N$_4$O$_3$Si (M+H): 429.2322. Found: 429.2329.

To a solution of 2 (2.10 g, 4.89 mmol) in methanol (375 mL) was added ammonium formate (4.64 g, 73.6 mmol) and 20% palladium hydroxide on carbon (980 mg). The reaction was heated to reflux for 1.5 hrs., then cooled to room temperature, filtered and concentrated under vacuum. Purification via flash chromatography (50/50 ethyl acetate/hexanes) yielded 3 (1.26 g, 94%).

$_1$H NMR (400 MHz, CDCl$_3$): δ 7.82 (s, 1H), 4.33 (t, 2H, J=6.0 Hz), 4.16 (q, 2H, J=7.2 Hz), 3.99 (t, 2H, J=6.0 Hz), 1.29 (t, 3H, J=7.2 Hz), 0.78 (s, 9H), 0.06 (s, 6H). HRMS: Calcd for C$_{15}$H$_{26}$N$_4$O$_3$Si (M+H): 339.1852. Found: 339.1864.

To 3 (970 mg, 2.86 mmol) was added dimethylformamide (25 mL), 3-bromo-4-methoxybenzyl bromide 15 (1.62 g, 5.79 mmol), and potassium carbonate (800 mg, 5.79 mmol) under nitrogen. The reaction mixture was stirred at room temperature for 21 hrs., then diluted with ethyl acetate and washed with water several times. The organic mixture was dried over potassium carbonate, filtered and concentrated under vacuum. Purification by flash chromatography (30/70 ethyl acetate/hexanes) yielded 10 (1.55 g, 100%).

$^1$H NMR (400 MHz, CDCl$_3$): δ 7.52 (s, 1H), 7.51 (d, 1H, J=2.4 Hz), 7.30 (dd 1H, J=2.0 Hz, J=8.4 Hz), 6.87 (d, 1H, J=8.8 Hz), 5.40 (s, 2H), 4.25 (t, 2H, J=6.0 Hz), 4.07 (q, 2H, J=7.0 Hz), 3.93 (t, 2H, J=6.0 Hz), 3.88 (s, 3H), 1.25 (t, 3H, J=7.0 Hz), 0.75 (s, 9H), 0.08 (s, 6H). HRMS: Calcd for C$_{23}$H$_{33}$BrN$_4$O$_4$Si(M+H): 537.1533. Found: 537.1540.

To solution of 10 (1.50 g, 2.80 mmol) in tetrahydrofuran (24 mL) under nitrogen at −78° C. (dry ice/acetone bath) was added lithium diisopropylamide (2M in THF/heptane, 2.2 mL, 4.33 mmol). After stirring for thirty minutes, 1,2-dibromotetrafluoroethane (0.69 mL, 5.77 mmol) was added dropwise over five minutes. The reaction was stirred for 1.25 hrs. at −78° C. then quenched with saturated aqueous sodium bicarbonate and warmed to room temperature. The mixture was extracted with dichloromethane, dried over potassium carbonate, filtered and concentrated under vacuum. Purification via flash chromatography (30/70 ethyl acetate/hexanes) yielded 11 (600 mg, 34%).

$^1$H NMR (400 MHz, CDCl$_3$): δ 7.60 (d, 1H, J=2.4 Hz), 7.35 (dd, 1H, J=2.0 Hz, J=8.4 Hz), 6.84 (d, 1H, J=8.4 Hz), 5.45 (s, 2H), 4.21 (t, 2H, J=5.6 Hz), 4.07 (q, 2H, J=6.8 Hz), 3.90 (t, 2H, J=5.6 Hz), 3.87 (s, 3H), 1.24 (t, 3H, J=6.8 Hz), 0.73 (s, 9H), 0.08 (s, 6H). HRMS: Calcd for C$_{23}$H$_{32}$Br$_2$N$_4$O$_4$Si (M+H): 615.0638. Found: 615.0633.

To 11 (1.89 g, 3.07 mmol) was added the amino alcohol hydrochloride salt (1.31 g, 12.27 mmol), diisopropylethylamine (15.4 mL), and 1-methyl-2-pyrrolidinone (15.4 mL). The reaction mixture was heated to 160° C. in a sealed tube for 13 hrs., then cooled to room temperature. Water was added, then the mixture was extracted with ethyl acetate and washed with water several times. The organic mixture was dried over potassium carbonate, filtered and concentrated under vacuum. Purification via flash chromatography (3/97 methanol/dichloromethane) yielded 12 (1.77 g, 90%).

$^1$H NMR (400 MHz, CDCl$_3$): δ 7.45 (d, 1H, J=2.0 Hz), 7.17 (dd, 1H, J=2.4 Hz, J=8.6 Hz), 6.86 (d, 1H, J=8.4 Hz), 5.18–4.34 (m, 3H), 4.00–4.23 (m, 5H), 3.86–3.98 (m, 6H), 3.69–3.79 (m, 1H), 2.10–2.21 (m, 1H), 1.99–2.10 (m, 1H), 1.60–1.84 (m, 3H), 1.32–1.43 (m, 1H), 1.24 (t, 3H, J=7.2 Hz), 0.75 (s, 9H), 0.07 (d, 6H, J=4.0 Hz). HRMS: Calcd for C$_{28}$H$_{43}$BrN$_5$O$_5$Si (M+H): 636.2217. Found: 636.2207.

12 (1.77 g, 2.78 mmol) was dissolved in tetrahydrofuran (28 mL) under nitrogen and tetrabutylammonium fluoride (1M in THF, 28 mL) was added dropwise. The reaction was stirred at room temperature for 15 hrs., then diluted with dichloromethane and washed with water several times. The organic mixture was dried over potassium carbonate, filtered and concentrated under vacuum. Purification via flash chromatography (3/97 methanol/dichloromethane) yielded 13 (compound no.114 in Table II) (760 mg, 52%).

$^1$H NMR (400 MHz, CDCl$_3$): δ 7.47 (d, 1H, J=2.0 Hz), 7.19 (dd, 1H, J=2.0 Hz, J=8.4 Hz), 6.88 (d, 1H, J=8.4 Hz), 5.25 (s, 2H), 5.09 (s, 1H), 4.21–4.27 (m, 3H), 4.06 (q, 2H, J=7.0 Hz), 3.90–3.97 (m, 3H), 3.89 (s, 1H), 3.74–3.82 (m, 1H), 3.08 (s, 1H), 2.12–2.22 (m, 1H), 1.98–2.08 (m, 1H), 1.60–1.86 (m, 3H), 1.33–1.43 (m, 1H), 1.25 (t, 3H, J=7.0 Hz), 1.06–1.22 (m, 3H). HRMS: Calcd for C$_{22}$H$_{28}$BrN$_5$O$_5$ (M+H): 522.1352. Found: 522.1346.

2-Bromo-4-methyl anisole 14 (2.2 mL, 14.9 mmol) was dissolved in dichlomethane (30 mL) and N-bromosuccinimide (3.75 g, 16.4 mmol) was added followed by AIBN (26.0 mg). The reaction was heated to reflux for 19 hrs., then cooled to room temperature and the precipitate was filtered off. The filtrate was diluted with dichloromethane and washed with 0.5 M aqueous sodium bicarbonate, followed by water. The organic mixture was dried over sodium sulfate, filtered and concentrated under vacuum to yield 15 (4.16 g, 100%). The benzyl bromide was used as the crude material without further purification.

$^1$ H NMR (400 MHz, CDCl$_3$): δ 7.59 (d, 1H, J=2.0 Hz), 7.30 (dd, 1H, J=2.4 Hz, J=8.4 Hz), 6.85 (d, 1H, J=8.4 Hz), 4.37 (s, 2H), 3.90 (s, 3H).

General Synthesis of Compound No. 114 in Table II (13)
a) Reacting 1 with an alkyl halide and base to form 2;
b) Debenzylation of 2 to form 3;
c) Alkylation of 3 with a benzyl halide to form 10;
d) Deprotonation of 10 followed by addition of a brominating agent to form 11;
e) Displacement of bromo 11 with an amine to form 12; and
f) Silyl ether cleavage of 12 to form compound no. 114 in Table II (13).

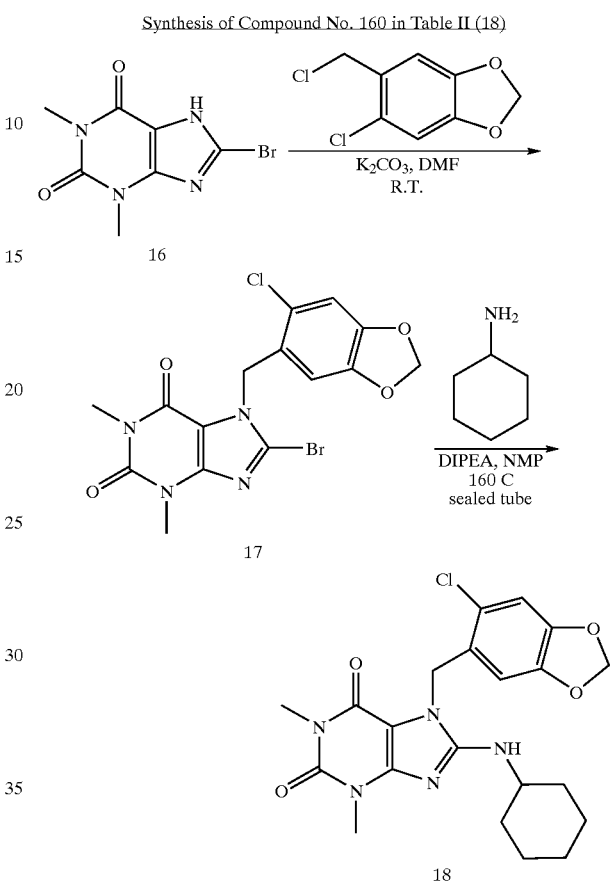

Synthesis of Compound No. 160 in Table II (18)

EXPERIMENTAL PROCEDURE

Compound No. 160 in Table II (18)

To 16 (150 mg, 0.579 mmol) was added dimethylformamide (3 mL), 6-chloropiperonyl chloride (142 mg, 0.694 mmol) and potassium carbonate (120 mg, 0.868 mmol) under nitrogen. The reaction mixture was stirred at room temperature for 137 hrs., then diluted with ethyl acetate and washed with water several times. The organic mixture was dried over magnesium sulfate, filtered and concentrated under vacuum. Purification via PTLC (1/1 ethyl acetate/hexanes) yielded 17 (84.1 mg, 34%).

$^1$H NMR (400 MHz, CDCl$_3$): δ 6.89 (s, 1H), 6.09 (s, 1H), 5.95 (s, 2H), 5.59 (s, 2H), 3.60 (s, 3H), 3.38 (s, 3H). HRMS: Calcd for C$_{15}$H$_{12}$BrClN$_4$O$_4$ (M+H): 426.9809. Found: 426.9802.

To 17 (72.0 mg, 0.169 mmol) was added cyclohexylamine (86.7 mg, 0.883 mmol), diisopropylethylamine (0.8 mL) and 1-methyl-2-pyrrolidinone (0.8 mL). The reaction mixture was heated to 160° C. in a sealed tube for 17 hrs., then cooled to room temperature. Water was added, then the mixture was extracted with ethyl acetate and washed with water several times. The organic mixture was dried over magnesium sulfate, filtered and concentrated under vacuum. Purification via PTLC (1/1 ethyl acetate/hexanes) yielded compound no. 160 in Table II (18) (50.9 mg, 68%).

87

$^1$H NMR (400 MHz, CDCl$_3$): δ 66.84 (s, 1H), 6.815 (s, 1H), 5.96 (s, 2H), 5.33 (s, 2H), 4.42 (d, 1H, J=7.2 Hz), 3.68–3.79 (m, 1 H), 3.53 (s, 3H), 3.40 (s, 3H), 1.94–2.05 (m, 2H), 1.55–1.74 (m, 3H), 1.25–1.42 (m, 2H), 1.10–1.22 (m, 3H). HRMS: Calcd for C$_{21}$H$_{24}$ClN$_5$O$_4$ (M+H): 444.2400. Found: 444.2394.

General Synthesis of Compound No. 160 in Table II (18)

a) Alkylation of 16 with a benzyl halide to form 17; and
b) Displacement of bromo 17 with an amine to form compound no. 160 in Table II (18).

Accordingly, the invention includes a method for producing a compound having the formula (I), comprising:

(i) reacting a compound having the formula (III) with an alkyl halide in the presence of a base to form a compound having the formula (IV):

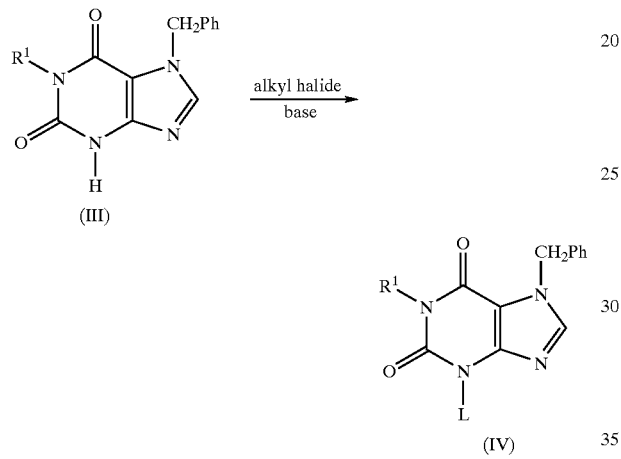

(III)

(IV)

where,
(a) R$^1$ is a hydrogen atom or a C$_{1-15}$ alkyl group, branched or straight chain, with or without one or more substituents, a C$_{2-15}$ alkenyl group, branched or straight chain, with or without one or more substituents, a C$_{2-15}$ alkynyl group, branched or straight chain, with or without one or more substituents, a C$_{3-15}$ cycloalkyl group, with or without one or more substituents, an arylalkyl group, with or without one or more substituents, an aryl group, with or without one or more substituents, a heteroaryl group, with or without one or more substituents, —OR$^5$, —COOR$^5$, —C(O)R$^5$ or —C(O)N(R$^5$)$_2$, where R$^5$ is a hydrogen atom or a hydrocarbon radical, branched or straight-chain, with or without one or more substituents
(b) L is R$^2$ or a protected form of R$^2$; and
(c) Ph is a phenyl group;

(ii) debenzylating and then alkylating the compound having the formula (IV) with an alkyl halide, XCH$_2$R$^3$, to form the compound having the formula (V):

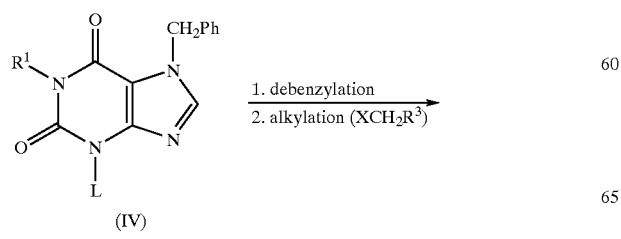

(IV)

88

-continued

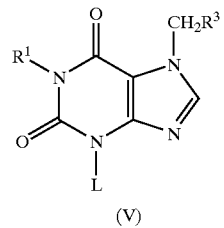

(V)

where,
X is a halogen atom (e.g., a chlorine or bromine atom) and
R$^3$ is an aryl group, with or without one or more substituents, a heteroaryl group, with or without one or more substituents, or a heterocyclic group having 1 to 3 heteroatoms fused to a 5 or 6 membered aryl ring, with or without one or more substituents, with the proviso that R$^3$ is not an aryl group substituted at its para position with a —Y-aryl group, where Y is a carbon—carbon single bond, —CO—, —O—, —S—, —N(R$^{21}$)—, —CON(R$^{22}$)—, —N(R$^{22}$)CO—, —OCH$_2$—, —CH$_2$—, —SCH$_2$—, —CH$_2$S—, —NHC(R$^{23}$)(R$^{24}$)—, —NR$^{23}$SO$_2$—, —SO$_2$NR$^{23}$—, —C(R$^{23}$)(R$^{24}$)NH—, —CH=CH—, —CF=CF—, —CH=CF—, —CF=CH—, —CH$_2$CH$_2$—, —CF$_2$CF$_2$—,

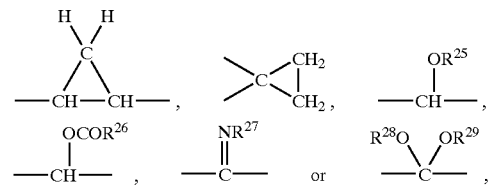

where,
R$^{21}$ is a hydrogen atom or a —CO(C$_{1-4}$ alkyl), C$_{1-6}$ alkyl, allyl, C$_{3-6}$ cycloalkyl, phenyl or benzyl group;
R$^{22}$ is a hydrogen atom or a C$_{1-6}$ alkyl group;
R$^{23}$ is a hydrogen atom or a C$_{1-5}$ alkyl, aryl or —CH$_2$-aryl group;
R$^{24}$ is a hydrogen atom or a C$_{1-4}$ alkyl group;
R$^{25}$ is a hydrogen atom or a C$_{1-8}$ alkyl, C$_{1-8}$ perfluoroalkyl, C$_{3-6}$ cycloalkyl, phenyl or benzyl group;
R$^{26}$ is a hydrogen atom or a C$_{1-6}$ alkyl, C$_{3-6}$ cycloalkyl, phenyl or benzyl group;
R$^{27}$ is —N R$^{23}$R$^{24}$, —OR$^{24}$, —NHCONH$_2$, —NHCSNH$_2$,

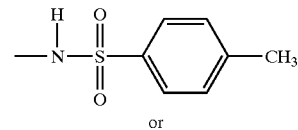

or

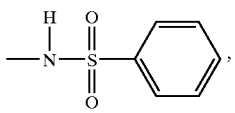

and
R$^{28}$ and R$^{29}$ are, independently of one another, each a C$_{1-4}$ alkyl group, or R$^{28}$ and R$^{29}$, taken together with each other, are a —(CH$_2$)$_q$ group, where q is 2 or 3;

wherein, $R^{21}$ through $R^{29}$ are optionally substituted with any of the groups defined above for the one or more substituents; and (iii) deprotonating and then halogenating the compound having the formula (V) to form a compound having the formula (VI):

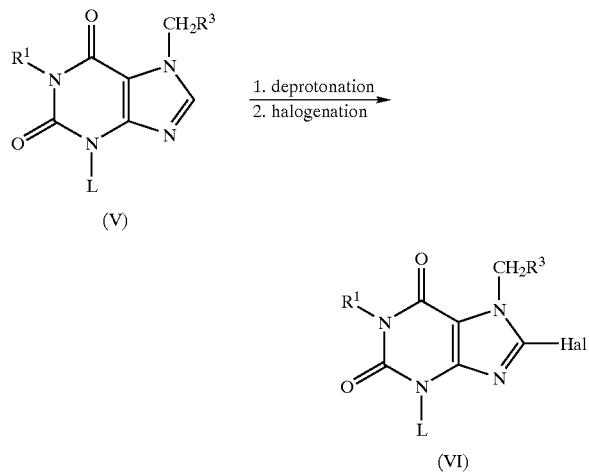

(V)

1. deprotonation
2. halogenation (VI)

where,

Hal is a halogen atom;

(iv) reacting the compound having the formula (VI) with an amine having the formula $R^4NH_2$ to form a compound having the formula (VII):

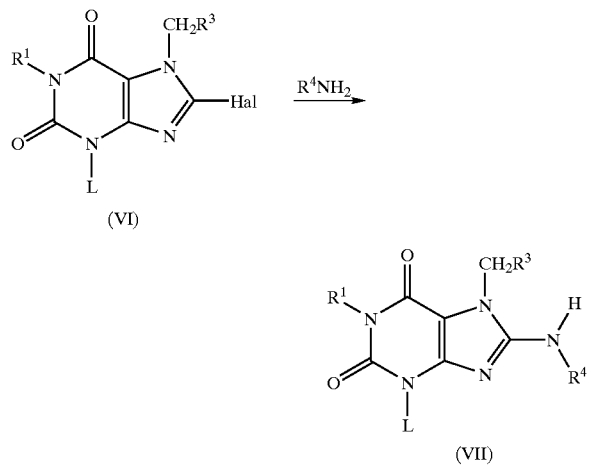

(VI)

$R^4NH_2$ (VII)

where, $R^4$ is a $C_{3-15}$ cycloalkyl group, with or without one or more substituents, a $C_{3-15}$ cycloalkenyl group, with or without one or more substituents, or a heterocycloalkyl group of 3 to 15 members, with or without one or more substituents; and (v) removing the protecting portion of L, when L is the protected form of $R^2$, on the compound having the formula (VII) to form the compound having the formula (I):

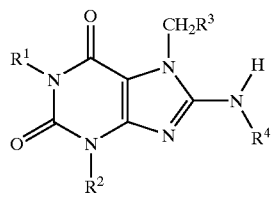

(I)

where,
$R^2$ is defined the same as $R^1$ above, with the proviso that at least one of $R^1$ and $R^2$ is not a hydrogen atom;
wherein, the one or more substituents are defined the same as for the one or more substituents of formula (I) above.

Pharmaceutically-Acceptable Dosage Forms

The compounds of the present invention may be administered to humans or other mammals by a variety of routes, including oral dosage forms and injections (intravenous, intramuscular, intraperitoneal, subcutaneous, and the like). Numerous other dosage forms containing the compounds of the present invention can be readily formulated by one skilled in the art, utilizing the suitable pharmaceutical excipients as defined below. For considerations of patient compliance, oral dosage forms are generally most preferred.

The rate of systemic delivery can be satisfactorily controlled by one skilled in the art, by manipulating any one or more of the following:

(a) the active ingredient proper;

(b) the pharmaceutically-acceptable excipient(s), so long as the variants do not interfere in the activity of the particular active ingredient selected;

(c) the type of excipient(s), and the concomitant desirable thickness and permeability (swelling properties) of the excipient(s);

(d) the time-dependent conditions of the excipient(s);

(e) the particle size of the granulated active ingredient; and (f) the pH-dependent conditions of the excipient(s).

Pharmaceutically-acceptable excipients include flavoring agents, pharmaceutical-grade dyes or pigments, solvents, co-solvents, buffer systems, surfactants, preservatives, sweetener agents, viscosity agents, fillers, lubricants, glidants, disintegrants, binders and resins.

Conventional flavoring agents may be used, such as those described in *Remington's Pharmaceutical Sciences*, 18th Ed., Mack Publishing Co., pp. 1288–1300 (1990), which is incorporated in its entirety by reference herein. The pharmaceutical compositions of the invention generally contain from about 0 to 2% of flavoring agents.

Conventional dyes and/or pigments may also be used, such as those described in the *Handbook of Pharmaceutical Excipients*, by the American Pharmaceutical Association & the Pharmaceutical Society of Great Britain, pp. 81–90 (1986), which is incorporated in its entirety by reference herein. The pharmaceutical compositions of the invention generally contain from about 0 to 2% of dyes and/or pigments.

The pharmaceutical compositions of the invention generally contain from about 0.1 to 99.9% of solvent(s). A preferred solvent is water. Preferred co-solvents include ethanol, glycerin, propylene glycol, polyethylene glycol, and the like. The pharmaceutical compositions of the invention may include from about 0 to 50% of co-solvents.

Preferred buffer systems include acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred buffers are phosphoric, tartaric, citric and acetic acids and salts thereof. The pharmaceutical compositions of the invention generally contain from about 0 to 5% of a buffer.

Preferred surfactants include polyoxyethylene sorbitan fatty acid esters, polyoxyethylene monoalkyl ethers, sucrose monoesters and lanolin esters and ethers, alkyl sulfate salts and sodium, potassium and ammonium salts of fatty acids. The pharmaceutical compositions of the invention generally contain from about 0 to 2% of surfactants.

Preferred preservatives include phenol, alkyl esters of parahydroxybenzoic acid, o-phenylphenol benzoic acid and salts thereof, boric acid and salts thereof, sorbic acid and salts thereof, chlorobutanol, benzyl alcohol, thimerosal, phenylmercuric acetate and nitrate, nitromersol, benzalkonium chloride, cetylpyridinium chloride, methyl paraben and propyl paraben. Particularly preferred preservatives are the salts of benzoic acid, cetylpyridinium chloride, methyl paraben and propyl paraben. The pharmaceutical compositions of the invention generally include from about 0 to 2% of preservatives.

Preferred sweeteners include sucrose, glucose, saccharin, sorbitol, mannitol and aspartame. Particularly preferred sweeteners are sucrose and saccharin. Pharmaceutical compositions of the invention generally include from about 0 to 5% of sweeteners.

Preferred viscosity agents include methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred viscosity agents are methylcellulose, carbomer, xanthan gum, guar gum, povidone, sodium carboxymethylcellulose, and magnesium aluminum silicate. Pharmaceutical compositions of the invention generally include from about 0 to 5% of viscosity agents.

Preferred fillers include lactose, mannitol, sorbitol, tribasic calcium phosphate, diabasic calcium phosphate, compressible sugar, starch, calcium sulfate, dextro and microcrystalline cellulose. Pharmaceutical compositions of the invention generally contain from about 0 to 75% of fillers.

Preferred lubricants/glidants include magnesium stearate, stearic acid and talc. Pharmaceutical compositions of the invention generally include from about 0 to 7%, preferably, about 1 to 5% of lubricants/glidants.

Preferred disintegrants include starch, sodium starch glycolate, crospovidone and croscarmelose sodium and microcrystalline cellulose. Pharmaceutical compositions of the invention generally include from about 0 to 20%, preferably, about 4 to 15% of disintegrants.

Preferred binders include acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. Pharmaceutical compositions of the invention generally include from about 0 to 12%, preferably, about 1 to 10% of binders.

Additional agents known to a skilled formulator may be combined with the compounds of the invention to create a single dosage form. Alternatively, additional agents may be separately administered to a mammal as part of a multiple dosage form.

For preparing pharmaceutical compositions containing the inventive compounds, inert, pharmaceutically acceptable carriers can be either solid or liquid. Solid form preparations include powders, tablets, dispersible granules, capsules, cachets and suppositories. The powders and tablets may be comprised of from about 5 to 95 weight percent of active ingredient. Suitable solid carriers are known in the art, for example, magnesium carbonate, magnesium stearate, talc, sugar and lactose. Tablets, powders, cachets and capsules can be used as solid dosage forms suitable for oral administration. Examples of pharmaceutically-acceptable carriers and methods of manufacture for various compositions may be found in *Remington's Pharmaceutical Sciences,* 18$^{th}$ Ed., Mack Publishing Co. (1990), which is incorporated in its entirety by reference herein.

Liquid form preparations include solutions, suspensions and emulsions. Common liquid form preparations include water and water-propylene glycol solutions for parenteral injection or addition of sweeteners and opacifiers for oral solutions, suspensions and emulsions. Liquid form preparations may also include solutions for intranasal administration.

Aerosol preparations suitable for inhalation include solutions and solids in powder form, which may be combined with a pharmaceutically acceptable carrier, such as an inert compressed gas (e.g., nitrogen).

Also included are solid form preparations that may be converted, shortly before use, to liquid form preparations for either oral or parenteral administration. Such liquid forms include solutions, suspensions and emulsions.

The compounds of the invention may also be delivered transdermally. The transdermal compositions can take the form of creams, lotions, aerosols and emulsions and may be included in a transdermal patch of a matrix or reservoir type as is conventional in the art for this purpose.

The preferred mode of administering the compounds of the invention is oral. Preferably, the pharmaceutical preparation is in a unit dosage form. In such a form, the preparation is subdivided into suitable sized unit doses containing appropriate quantities of the active component, for example, an effective amount to achieve the desired purpose.

The quantity of active ingredient (compound) in a unit dose of preparation may be varied or adjusted from about 0.01 to 4,000 mg, preferably, from about 0.02 to 1,000 mg, more preferably, from about 0.3 to 500 mg, and most preferably, from about 0.04 to 250 mg, according to the particular application. A typical recommended daily dosage regimen for oral administration can range from about 0.02 to 2,000 mg/day, in two to four divided doses. For convenience, the total daily dosage may be divided and administered in portions during the day as required. Typically, pharmaceutical compositions of the invention will be administered from about 1 to 5 times per day, or alternatively, as a continuous infusion. Such administration can be used as a chronic or acute therapy. The amount of active ingredient that may be combined with carrier materials to produce a single dosage form will vary depending upon the host treated and the particular mode of administration. A typical preparation will contain from about 5 to 95% of active compound (w/w). Preferably, such preparations will contain from about 20 to 80 wt. % of active compound.

The pharmaceutically-acceptable carriers employed in conjunction with the compounds of the present invention are used at a concentration sufficient to provide a practical size to dosage relationship. The pharmaceutically-acceptable carriers, in total, may comprise from about 0.1 to 99.9% by weight of the pharmaceutical compositions of the invention, preferably, from about 20 to 80% by weight.

Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art. The amount and frequency of the administration of compounds of the invention or their pharmaceutically acceptable salts may be regulated according to the judgment of the attending clinician, based on the factors recited above. As a skilled artisan will appreciate, lower or higher doses than those recited above may be required.

For example, it is often the case that a proper dosage level is based on the weight of the patient. For instance, dosage levels of between about 0.01 and 100 mg/kg of body weight per day, preferably, between about 0.5 and 75 mg/kg of body weight per day, and more preferably, between about 1 and 50 mg/kg of body weight per day, of the inventive compounds, compositions and salts thereof described herein, are therapeutically useful for the treatment of a variety of biological disorders, particularly, male and female sexual dysfunction. Between two patients of differing weights, a higher dosage will be used for the heavier patient, all other things being equal.

The inventive compounds are understood to provide efficacious treatment of (male) erectile dysfunction, including a reasonable time of onset upon administration, and a reasonable duration after administration. For example, in the treatment of erectile dysfunction, a dosage of the inventive compound may be taken about an hour before a sex act is to be undertaken. Particular dosages will work within about thirty minutes of their administration. Ideal dosages will affect a patient within about fifteen minutes of their administration. While food, diet, pre-existing conditions, alcohol and other systemic conditions could lengthen the time delay for an inventive drug to work after its administration, it is understood that optimum dosages in combination with sexual stimulation will result in an efficacious drug treatment within and for a reasonable amount of time.

The inventive compounds can exist in unsolvated as well as solvated forms, including hydrated forms. In general, the solvated forms, with pharmaceutically-acceptable solvents, such as water, ethanol and the like, are equivalent to the unsolvated forms for purposes of this invention.

The inventive compounds may form pharmaceutically-acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention.

The invention comprises a compound having the formula (I) or (II), a method for making an inventive compound, a method for making a pharmaceutical composition from at least one inventive compound and at least one pharmaceutically-acceptable carrier, and a method of using one or more inventive compounds to treat a variety of disorders, symptoms and diseases.

The inventive compounds and their pharmaceutically-acceptable salt and neutral compositions may be formulated together with a pharmaceutically-acceptable carrier. The resulting composition may be administered in vivo to mammals, such as men or women, to treat a variety of disorders, symptoms and diseases. For example, the inventive compounds and compositions may be used to treat diseases of the urogenital system, specifically, male erectile dysfunction (e.g., impotence) and female sexual dysfunction. Male erectile dysfunction may be defined as an inability of the male to sufficiently obtain and/or sustain an erection to have intercourse with his mate. In the treatment of erectile dysfunction, it is believed that the inventive PDE V inhibitors of formulas (I) and (II) are beneficial therapeutic agents because they elevate cGMP levels in the human body. This action facilitates corpus cavernosum smooth muscle relaxation, which provides an increased flow of blood therein and results in an erection. This makes the inventive compounds especially useful for treating impotence and other types of diseases that are affected by cGMP levels.

Accordingly, another aspect of the invention is a method for treating erectile dysfunction in a mammal in need of such treatment, comprising administering to the mammal at least one compound having the formula (I) or (II) or a pharmaceutical composition thereof in an amount effective to ameliorate and/or reduce one or more of the symptoms associated with erectile dysfunction sufficiently enough so that the mammal can complete intercourse with another mammal.

Introduced in 1998 as the first pill to treat impotence, Viagra® today is the most commonly prescribed medication to treat physiologically-caused erectile dysfunction ("ED"). Certain patients, however, can experience undesirable side effects while taking Viagra®. For instance, the use of Viagra® is contraindicated to patients who are using organic nitrates, either regularly or intermittently. *Physicians' Desk Reference®*, $55^{th}$ Ed, pp. 2534–37 (2001). Combining Viagra® with nitrates can cause a hypotensive episode or suddenly reduce blood pressure to dangerous levels, which may cause a heart attack. Id. Accordingly, men who have a heart condition that requires the use of nitrate drugs should not use Viagra®. Id. It has also been reported that Viagra® can cause a vision side effect by impairing the patient's color discrimination (blue/green), causing a "blue-halo" light visual alteration. Id. This side effect is presumably due to inhibition of the PDE VI isoenzyme (found in a retina). Id.

An advantage of the inventive compounds is that they can be particularly selective for the PDE V isoenzyme in comparison to other types of PDE isoenzymes, such as the PDE VI isoenzyme. It is believed that this increased selectivity will ameliorate side effects associated with the use of Viagra®. In particular, the high selectivity of the inventive compounds should minimize, and may even prevent, the occurrence of a "blue-halo" light visual alteration. It is believed that the increased isoenzyme selectivity in inhibiting PDE V isoenzyme (found in a penis) versus PDE VI isoenzyme (found in a retina) accounts for obviating the "blue-halo" visual side effect.

The compounds of the present invention may be employed alone or in combination with other agents, particularly, other types of PDE inhibitors (especially cGMP PDE V inhibitors), prostanoids, α-adrenergic receptor, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, renin inhibitors, serotonin 5-HT$_{2c}$ receptor agonists, nociceptin receptor agonists, rho kinase inhibitors, potassium channel modulators and inhibitors of multidrug resistance protein 5.

Examples of therapeutic agents that may be used in combination with compounds of the invention are the following: PDE V inhibitors, such as sildenafil citrate (Viagra®, Pfizer, Conn., United States), Vardenafil™ (Bayer, Germany) and IC-351 (Cialis™, Lilly-ICOS, Washington and Indiana, United States); prostanoids, such as prostaglandin E$_1$; α-adrenergic agonists, such as phentolamine mesylate; dopamine receptor agonists, such as apomorphine; angiotensin II antagonists, such as losartan, irbesartan, valsartan and candesartan; and ET$_A$ antagonists, such as bosentan and ABT-627.

It is understood that other combinations may be undertaken while remaining within the scope of the invention. While one or more of the inventive compounds may be used in an application of monotherapy to treat erectile dysfunction, they also may be used in combination therapy, in which the inventive compounds are combined with one or more other pharmaceutical compounds that are useful for treating erectile dysfunction and/or other types of disorders, symptoms and diseases.

As discussed above, due to their cGMP-PDE V inhibitory activities, the inventive compounds are useful for treating urological disorders, in particular, female and male sexual dysfunctions. Other physiological disorders, symptoms and diseases can also benefit from cGMP-PDE V inhibition. More specifically, the inventive compounds, salts and derivatives thereof may be used to treat cardiovascular and cerebrovascular diseases, angina pectoris, hypertension, restenosis post angioplasty, endarterectomy, stent introduction, peripheral vascular diseases, cerebral stroke, respiratory tract disorders, such as reversible airway obstruction, chronic asthma and bronchitis, allergic disorders associated with atopy, such as urticaria, eczema, and rinitis, pulmonary hypertension, ischemic heart diseases, impaired glucose tolerance, diabetes and related complications, insulin resistance syndrome, hyperglycemia, polycystic ovarian syndrome, glomerular diseases, renal insufficiency, nephritis, tubular interstitial disease, autoimmune diseases, glaucoma, intestinal motility disorders, cachexia and cancer.

Another aspect of this invention is to provide a kit comprising separate containers in a single package, wherein the inventive pharmaceutical compounds, compositions and/or salts thereof are used in combination with pharmaceutically-acceptable carriers to treat disorders, symptoms and diseases where cGMP-PDE V inhibition plays a role.

It is understood that other combinations may be undertaken while remaining within the scope of the invention. While one or more of the inventive compounds may be used in an application of monotherapy to treat erectile dysfunction, they also may be used in combination therapy, in which the inventive compounds are combined with one or more other pharmaceutical compounds that are useful for treating erectile dysfunction and/or other types of disorders, symptoms and diseases.

As discussed above, due to their cGMP-PDE V inhibitory activities, the inventive compounds are useful for treating urological disorders, in particular, female and male sexual dysfunctions. Other physiological disorders, symptoms and diseases can also benefit from cGMP-PDE V inhibition. More specifically, the inventive compounds, salts and derivatives thereof may be used to treat cardiovascular and cerebrovascular diseases, angina pectoris, hypertension, restenosis post angioplasty, endarterectomy, stent introduction, peripheral vascular diseases, cerebral stroke, respiratory tract disorders, such as reversible airway obstruction, chronic asthma and bronchitis, allergic disorders associated with atopy, such as urticaria, eczema, and rinitis, pulmonary hypertension, ischemic heart diseases, impaired glucose tolerance, diabetes and related complications, insulin resistance syndrome, hyperglycemia, polycystic ovarian syndrome, glomerular diseases, renal insufficiency, nephritis, tubular interstitial disease, autoimmune diseases, glaucoma, intestinal motility disorders, cachexia and cancer.

Another aspect of this invention is to provide a kit comprising separate containers in a single package, wherein the inventive pharmaceutical compounds, compositions and/or salts thereof are used in combination with pharmaceutically-acceptable carriers to treat disorders, symptoms and diseases where cGMP-PDE V inhibition plays a role.

The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A compound of Formula (I), an enantiomer, stereoisomer, rotomer, tautomer or a pharmaceutically acceptable salt thereof:

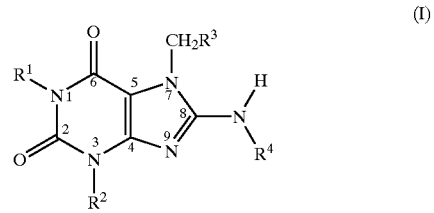

(I)

where,
(a) $R^1$ and $R^2$ are, independently of one another, each a $C_{1-15}$ alkyl group, branched or straight chain, unsubstituted or substituted with one or more substituents, a $C_{2-15}$ alkenyl group, branched or straight chain, unsubstituted or substituted with one or more substituents, a $C_{2-15}$ alkynyl group, branched or straight chain, unsubstituted or substituted with one or more substituents, a $C_{3-15}$ cycloalkyl group, unsubstituted or substituted with one or more substituents, an arylalkyl group, unsubstituted or substituted with one or more substituents, an aryl group, unsubstituted or substituted with one or more substituents, a heteroaryl group, unsubstituted or substituted with one or more substituents, —OR$^5$, —COOR$^5$, —C(O)R$^5$ or —C(O)N(R$^5$)$_2$, where, $R^5$ is a hydrogen atom or a hydrocarbon radical, unsubstituted or substituted with one or more substituents, or one of $R^1$ and $R^2$ is a hydrogen atom and the other one of $R^1$ and $R^2$ is defined the same as above;

(b) $R^3$ is an aryl group, unsubstituted or substituted with one or more substituents, a heteroaryl group, unsubstituted or substituted with one or more substituents, or a heterocyclic group having 1 to 3 heteroatoms fused to a 5- or 6-membered aryl ring, unsubstituted or substituted with one or more substituents, with the proviso that $R^3$ is not an aryl group substituted at its para position with a —Y-aryl group, where, Y is a carbon—carbon single bond, —C(O)—, —O—, —S—, —N($R^{21}$)—, —C(O)N ($R^{22}$)—, —N($R^{22}$)C(O)—, —OCH$_2$—, —CH$_2$O—, —SCH$_2$—, —CH$_2$S—, —N(H)C($R^{23}$)($R^{24}$)—, —N($R^{23}$)S(O$_2$)—, —S(O$_2$)N($R^{23}$)—, —($R^{23}$)($R^{24}$) N(H)—, —CH=CH—, —CF=CF—, —CH=CF—, —CF=CH—, —CH$_2$CH$_2$—, —CF$_2$CF$_2$—,

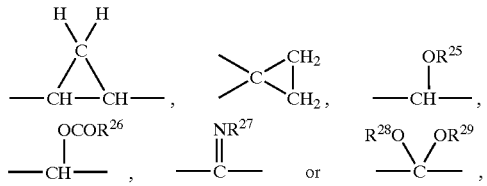

where, $R^{21}$ is a hydrogen atom or a —CO(C$_{1-4}$ alkyl), C$_{1-6}$ alkyl, allyl, C$_{3-6}$ cycloalkyl, phenyl or benzyl group;

$R^{22}$ is a hydrogen atom or a C$_{1-6}$ alkyl group;

$R^{23}$ is a hydrogen atom or a C$_{1-5}$ alkyl, aryl or —CH$_2$-aryl group;

$R^{24}$ is a hydrogen atom or a C$_{1-4}$ alkyl group;

$R^{25}$ is a hydrogen atom or a C$_{1-8}$ alkyl, C$_{1-8}$ perfluoroalkyl, C$_{3-6}$ cycloalkyl, phenyl or benzyl group;

$R^{26}$ is a hydrogen atom or a C$_{1-6}$ alkyl, C$_{3-6}$ cycloalkyl, phenyl or benzyl group;

$R^{27}$ is —NR$^{23}$R$^{24}$, —OR$^{24}$, —NHCONH$_2$, —NHCSNH$_2$,

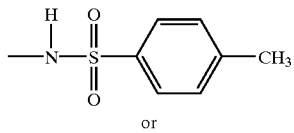

or

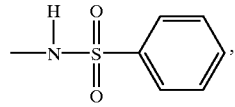

and $R^{28}$ and $R^{29}$ are, independently of one another, each a C$_{1-4}$ alkyl group or, taken together with each other, a —(CH$_2$)$_q$ group, where q is 2 or 3; and (c) $R^4$ is a C$_{3-15}$ cycloalkyl group, with or without unsubstituted or substituted with one or more substituents, or a C$_{3-15}$ cycloalkenyl group, unsubstituted or substituted with one or more substituents;

wherein, the one or more substituents for all the groups are chemically-compatible and are, independently of one another, each an: alkyl, cycloalkyl, alkenyl, cycloalkenyl, alkynyl, arylalkyl, alkylaryl, aryl, heteroaryl, heterocycloalkyl, hydroxyalkyl, arylalkyl, aminoalkyl, haloalkyl, thioalkyl, alkylthioalkyl, carboxyalkyl, imidazolylalkyl, indolylalkyl, mono-, di- and trihaloalkyl, mono-, di- and trihaloalkoxy, amino, alkylamino, dialkylamino, alkoxy, hydroxy, halo, nitro, oximino, —COOR$^{50}$, —COR$^{50}$, —SO$_2$R$^{50}$, —SO$_2$NR$^{50}$R$^{51}$, NR$^{52}$SO$_2$R$^{50}$, =C(R$^{50}$R$^{51}$), =N—OR$^{50}$, =N—CN, =C(halo)$_2$, =S, =O, —CON(R$^{50}$R$^{51}$), —OCOR$^{50}$, —OCON(R$^{50}$R$^{51}$), —N(R$^{52}$)CO(R$^{50}$), —N(R$^{52}$)COOR$^{50}$ or —N(R$^{52}$) CON(R$^{50}$R$^{51}$) group, where:

$R^{50}$, $R^{51}$ and $R^{52}$ are, independently of one another, each a hydrogen atom or a branched or straight-chain, optionally substituted, C$_{1-6}$ alkyl, C$_{3-6}$ cycloalkyl, C$_{4-6}$ heterocycloalkyl, heteroaryl or aryl group, or $R^{50}$ and $R^{51}$ are joined together to form a carbocyclic or heterocyclic ring system, or $R^{50}$, $R^{51}$ and $R^{52}$ are, independently of one another, each:

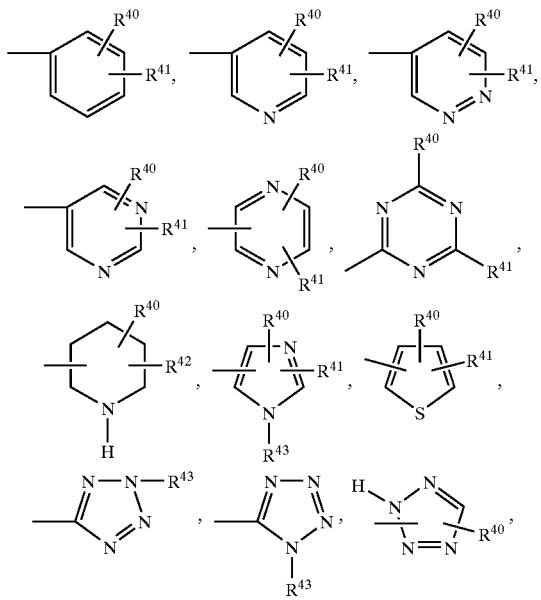

where, $R^{40}$ and $R^{41}$ are, independently of one another, each a hydrogen atom or a branched or straight-chain, optionally substituted, alkyl, cycloalkyl, heterocycloalkyl, halo, aryl, imidazolylalkyl, indolylalkyl, heteroaryl, arylalkyl, arylalkoxy, heteroarylalkyl, heteroarylalkoxy, aminoalkyl, haloalkyl, mono-, di- or trihaloalkyl, mono-, di- or trihaloalkoxy, nitro, cyano, alkoxy, hydroxy, amino, phosphino, phosphate, alkylamino, dialkylamino, formyl, alkylthio, trialkylsilyl, alkylsulfonyl, arylsulfonyl, alkylsulfinyl, aminoalkyl, alkylaminoalkyl, dialkylaminoalkyl, hydroxyalkyl, morpholino, thioalkyl, alkylthioalkyl, carboxyalkyl, oximino, —COOR$^{50}$, —COR$^{50}$, —SO$_{0-2}$R$^{50}$, —SO$_2$NR$^{50}$R$^{51}$, —NR$^{52}$SO$_2$R$^{50}$, —CON(R$^{50}$R$^{51}$), —OCON(R$^{50}$R$^{51}$), —N(R$^{52}$)CO(R$^{50}$), —N(R$^{52}$) COOR$^{50}$, —N(R$^{52}$)CON(R$^{50}$R$^{51}$) or —OCONR$^{50}$ group, where, $R^{50}$, $R^{51}$ and $R^{52}$ are defined the same as above;

$R^{42}$ is a hydrogen atom or a branched or straight-chain, optionally substituted, alkyl, alkenyl, arylalkyl or acyl group; and $R^{43}$ is a hydrogen atom or a branched or straight-chain, optionally substituted, alkyl or aryl group;

wherein, the optional substituents are defined the same as above for the one or more substituents.

2. The compound according to claim 1, where, $R^1$ is an alkyl or aryl group, with or without the one or more substituents.

3. The compound according to claim 2, where, $R^1$ is a methyl, ethyl or benzyl group, with or without the one or more substituents.

4. The compound according to claim 1, where, $R^2$ is an alkyl group, with or without the one or more substituents.

5. The compound according to claim 4, where, $R^2$ is a methyl, ethyl, iso-butyl or hydroxyethyl group, with or without the one or more substituents.

6. The compound according to claim 1, where, $R^3$ is an aryl group, with or without the one or more substituents.

7. The compound according to claim 6, where, $R^3$ is a hydroxyaryl, alkoxyaryl or aminosulfonylaryl group, with or without the one or more substituents.

8. The compound according to claim 7, where, the hydroxyaryl, alkoxyaryl or aminosulfonylaryl group for $R^3$ is substituted with at least one halogen atom on the aryl ring.

9. The compound according to claim 1, where, $R^4$ is a cycloalkyl, with or without the one or more substituents.

10. The compound or pharmaceutical composition according to claim 9, where, $R^4$ is a cyclohexyl, hydroxycyclopentyl or tetrahydropyranyl group, with or without the one or more substituents.

11. The compound or pharmaceutical composition according to claim 1, where, $R^1$ is a methyl or ethyl group, $R^2$ is a methyl, ethyl or hydroxyethyl group, $R^3$ is a 3-chloro-4-hydroxyphenyl, 3-bromo-4-hydroxyphenyl, 3-chloro-4-methoxyphenyl, 3-bromo-4-methoxyphenyl, or 4-aminosulfonylphenyl group and $R^4$ is a cyclohexyl, tetrahydropyranyl or 2(R)-hydroxy-1(R)-cyclopentyl group.

12. The compound according to claim 1,
where, $R^1$ is an alkyl or aryl group, with or without the one or more substituents, $R^2$ is an alkyl group, with or without the one or more substituents, and $R^3$ is a 4-hydroxyphenyl, 3-chloro-4-hydroxyphenyl, 3-bromo-4-hydroxyphenyl, 4-methoxyphenyl, 3-chloro-4-methoxyphenyl, 3-bromo-4-methoxyphenyl, 4-aminosulfonylphenyl, 3-chloro-4-aminosulfonylphenyl or 3-bromo-4-aminosulfonylphenyl group.

13. The compound according to claim 1, which is:

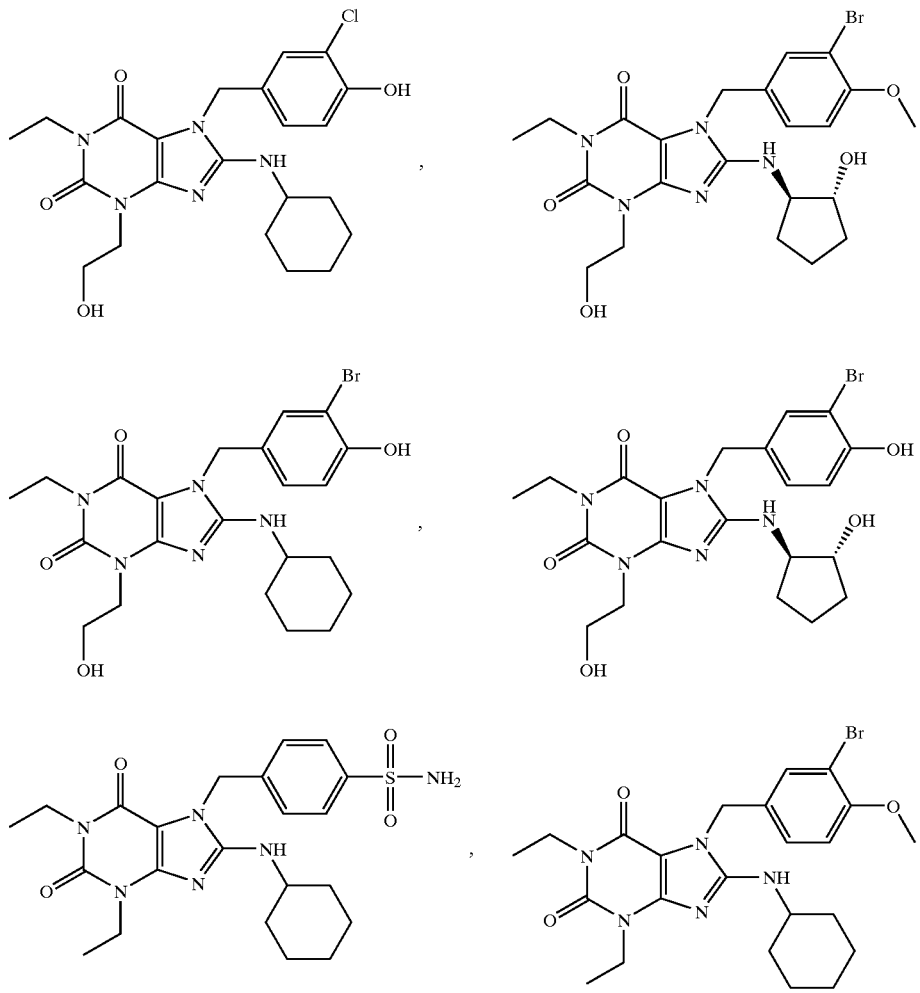

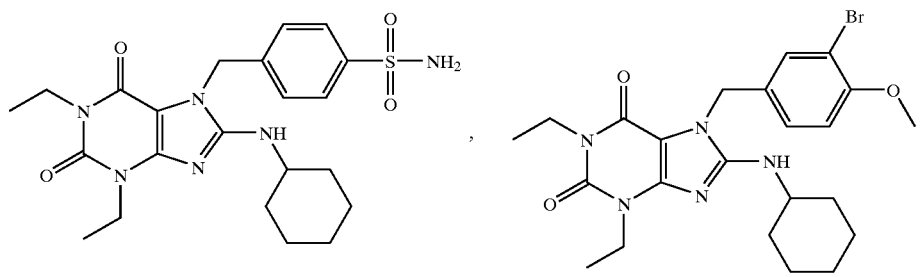

-continued
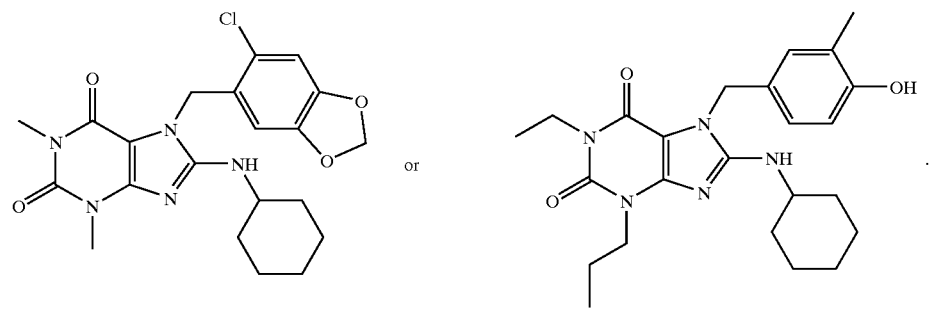
14. The compound according to claim 1, which is:
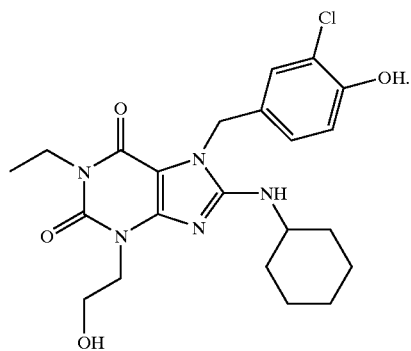
15. The compound according to claim 1, which is:
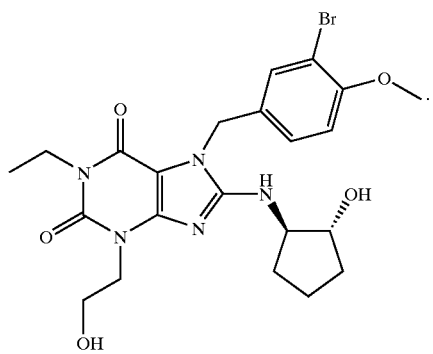
16. The compound according to claim 1, which is:
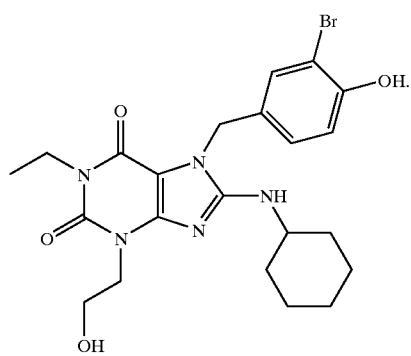
17. The compound according to claim 1, which is:
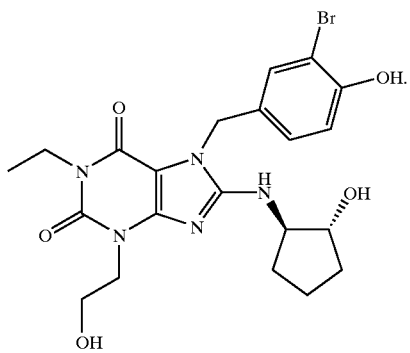
18. The compound according to claim 1, which is:
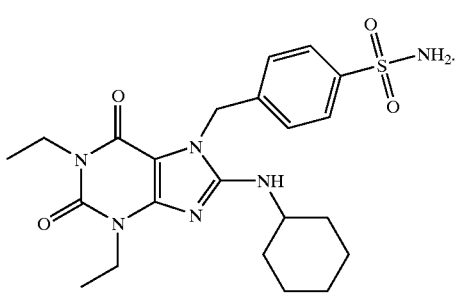
19. The compound according to claim 1, which is:
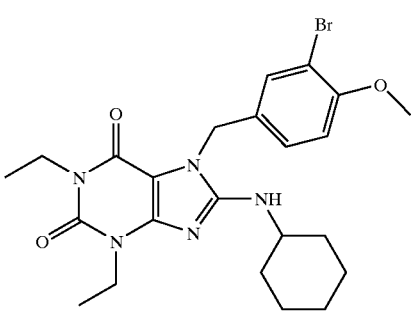

20. The compound according to claim 1, which is:

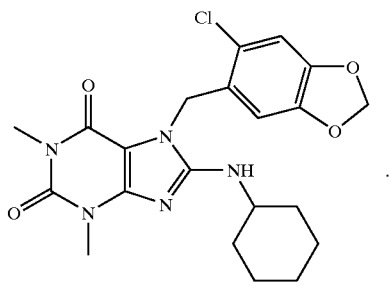

21. The compound according to claim 1, which is:

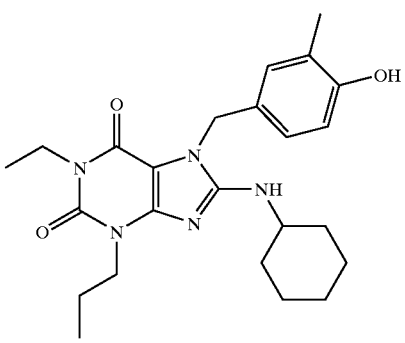

22. The compound according to claim 1, where, $R^4$ is:

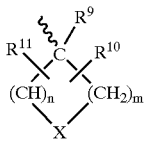

where,
$R^1$, $R^2$ and $R^3$, independently of one another, are each defined the same as above for the compound of formula (I);
$R^9$ is a hydrogen atom or an optionally substituted, oximino, carboxyalkyl, —COOH, ester, $C_{1-6}$ alkyl, $C_{3-6}$ cycloalkyl, $C_{3-6}$ heterocyclic, hydroxy $C_{1-6}$ alkyl, aryl or heteroaryl group;
$R^{10}$ and $R^{11}$ are substituents on the same or different carbon atoms of the ring and, independently of one another, are each:
(a) defined the same as above for $R^9$;
(b) a hydroxy group or an ester group derived from a hydroxy group with a $C_{1-6}$ carboxylic acid; or
(c) a $C_{1-6}$ alkoxy, amino, $C_{1-6}$ mono- or dialkylamino, $C_{1-6}$ alkylacylamino, $C_{1-6}$ alkylsulfonylamino or —NHCON($R^{14}$)$_2$ group, unsubstituted or substituted with one or more substituents, where $R_{1-4}$ is a hydrogen atom or an optionally substituted, $C_{1-6}$ alkyl or aryl group, or
$R^{10}$ and $R^{11}$, taken together with each other and, optionally, with one or more carbon or hetero atoms of the ring, form an optionally substituted, spiro- or linearly fused, bi- or tri-cyclic ring system of from 8 to 12 members, including from 0 to 4 hetero atoms;
m and n, independently of one other, are each from 1 to 3; and
X is a chemically-compatible group, which is —C($R^{10}R^{11}$)—, where:
$R^{10}$ and $R^{11}$ are defined as above;

wherein, the optional substituents are defined the same as for the one or more substituents of formula (I) above.

23. The compound according to claim 22, where, $R^3$ is an optionally substituted, hydroxyaryl, alkoxyaryl or aminosulfonylaryl group, wherein, the optional substituents are defined the same as for the one or more substituents of formula (I) above.

24. The compound according to claim 22, where, $R^9$ is a hydrogen atom.

25. The compound according to claim 22, where, one of $R^{10}$ and $R^{11}$ is a hydrogen atom, and the other one of $R^{10}$ and $R^{11}$ is a hydrogen atom or a hydroxy group.

26. A method for producing a compound having the formula (I), comprising:

(i) reacting a compound having the formula (III) with an alkyl halide in the presence of a base to form a compound having the formula (IV):

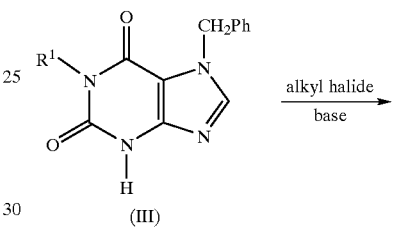

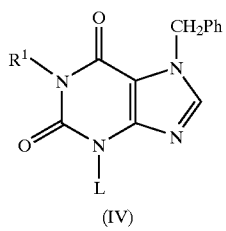

where,
(a) $R^1$ is a hydrogen atom or a $C_{1-15}$ alkyl group, branched or straight chain, unsubstituted or substituted with one or more substituents, a $C_{2-15}$ alkenyl group, branched or straight chain, unsubstituted or substituted with one or more substituents, a $C_{2-15}$ alkynyl group, branched or straight chain, with or without unsubstituted or substituted with one or more substituents, a $C_{3-5}$ cycloalkyl group, unsubstituted or substituted with one or more substituents, an arylalkyl group, unsubstituted or substituted with one or more substituents, an aryl group, unsubstituted or substituted with one or more substituents, a heteroaryl group, unsubstituted or substituted with one or more substituents, —OR$^5$, —COOR$^5$, —C(O)R$^5$ or —C(O)N(R$^5$)$_2$, where R$^5$ is a hydrogen atom or a hydrocarbon radical, branched or straight-chain, with or without unsubstituted or substituted with one or more substituents;
(b) L is $R^2$ or a protected form of $R^2$; and
(c) Ph is a phenyl group;
(ii) debenzylating and then alkylating the compound having the formula (IV) with an alkyl halide having the formula XCH$_2$R$^3$ to form the compound having the formula (V):

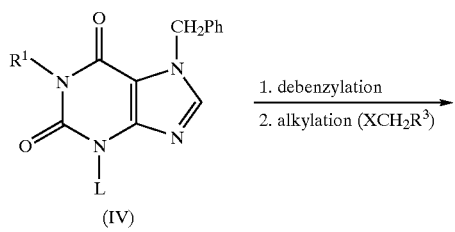

(IV)

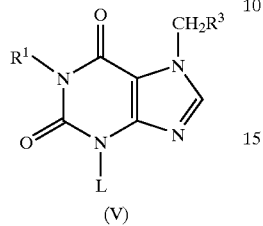

(V)

where,
X is a halogen atom and
R³ is an aryl group, unsubstituted or substituted with one or more substituents, a heteroaryl group, unsubstituted or substituted with one or more substituents, or a heterocyclic group having 1 to 3 heteroatoms fused to a 5- or 6-membered aryl ring, unsubstituted or substituted with one or more substituents, with the proviso that R³ is not an aryl group substituted at its para position with a —Y-aryl group, where Y is a carbon—carbon single bond, —CO—, —O—, —S—, —N($R^{21}$)—, —CON($R^{22}$)—, —N($R^{22}$)CO—, —OCH₂—, —CH₂O—, —SCH₂—, —CH₂S—, —NHC($R^{23}$)($R^{24}$)—, —NR²³SO₂—, —SO₂NR²³—, —C($R^{23}$)($R^{24}$)NH—, —CH=CH—, —CF=CF—, —CH=CF—, —CF=CH—, —CH₂CH₂—, —CF₂CF₂—,

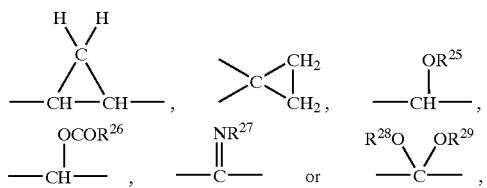

where,
$R^{21}$ is a hydrogen atom or a —CO($C_{1-4}$alkyl), $C_{1-6}$ alkyl, allyl, $C_{3-6}$ cycloalkyl, phenyl or benzyl group;
$R^{22}$ is a hydrogen atom or a $C_{1-6}$ alkyl group;
$R^{23}$ is a hydrogen atom or a $C_{1-5}$ alkyl, aryl or —CH₂-aryl group;
$R^{24}$ is a hydrogen atom or a $C_{1-4}$ alkyl group;
$R^{25}$ is a hydrogen atom or a $C_{1-8}$ alkyl, $C_{1-8}$ perfluoroalkyl; $C_{3-6}$ cycloalkyl, phenyl or benzyl group;
$R^{26}$ is a hydrogen atom or a $C_{1-6}$ alkyl, $C_{3-6}$ cycloalkyl, phenyl or benzyl group;
$R^{27}$ is —NR²³R²⁴, —OR²⁴, —NHCONH₂, —NHCSNH₂,

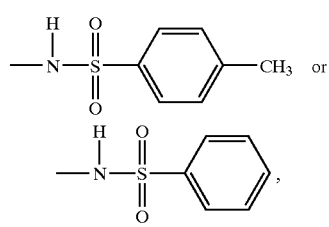

and $R^{28}$ and $R^{29}$ are, independently of one another, each a $C_{1-4}$ alkyl group, or $R^{28}$ and $R^{29}$, taken together with each other, are a —CH₂)$_q$ group, where q is 2 or 3;
wherein, $R^{21}$ through $R^{29}$ are optionally substituted with one or more substituents; and (iii) deprotonating and then halogenating the compound having the formula (V) to form a compound having the formula (VI):

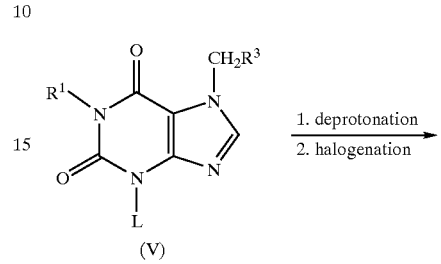

(V)

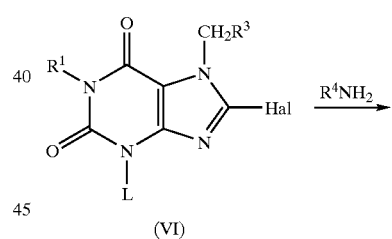

(VI)

where,
Hal is a halogen atom;

(iv) reacting the compound having the formula (VI) with an amine having the formula R⁴NH₂ to form a compound having the formula (VII):

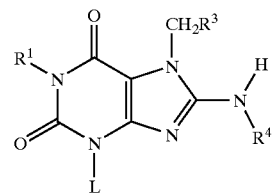

(VI)

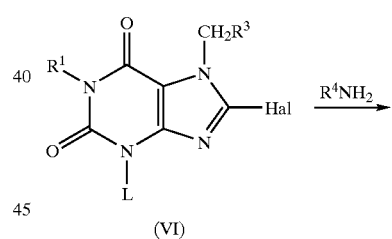

(VII)

where,
R⁴ is a $C_{3-15}$ cycloalkyl group, with or without one or more substituents, or a $C_{3-15}$ cycloalkenyl group, with or without unsubstituted or substituted with one or more substituents; and (v) removing the protecting portion of L, when L is the protected form of R², on the compound having the formula (VII) to form the compound having the formula (I):

(I)

[Structure of formula (I): xanthine-like core with R¹ on N1, R² on N3, CH₂R³ on N7, and NHR⁴ at C8]

where,
R² is defined the same as R¹ above, with the proviso that at least one of R¹ and R² is not a hydrogen atom;
wherein, the one or more substituents for all the groups are chemically-compatible and are, independently of one another, each an: alkyl, cycloalkyl, alkenyl, cycloalkenyl, alkynyl, arylalkyl, alkylaryl, aryl, heteroaryl, heterocycloalkyl, hydroxyalkyl, arylalkyl, aminoalkyl, haloalkyl, thioalkyl, alkylthioalkyl, carboxyalkyl, imidazolylalkyl, indolylalkyl, mono-, di- and trihaloalkyl, mono-, di- and trihaloalkoxy, amino, alkylamino, dialkylamino, alkoxy, hydroxy, halo, nitro, oximino, —COOR$^{50}$, —COR$^{50}$, —SO$_{0-2}$R$^{50}$, —SO$_2$NR$^{50}$R$^{51}$, NR$^{52}$SO$_2$R$^{50}$, =C(R$^{50}$R$^{51}$), =N—OR$^{50}$, =N—CN, C(halo)$_2$, S, O, —CON(R$^{50}$R$^{51}$), —OCOR$^{50}$, —OCON(R$^{50}$R$^{51}$), —N(R$^{52}$)CO(R$^{50}$), —N(R$^{52}$)COOR$^{50}$ or —N(R$^{52}$)CON(R$^{50}$R$^{51}$) group, where:
R$^{50}$, R$^{51}$ and R$^{52}$ are, independently of one another, each a hydrogen atom or a C$_{1-6}$ alkyl, C$_{3-6}$ cycloalkyl, C$_{4-6}$ heterocycloalkyl, heteroaryl and aryl group, or R$^{50}$ and R$^{51}$ are joined together to form a carbocyclic or heterocyclic ring system, or R$^{50}$, R$^{51}$ and R$^{52}$ are, independently of one another, each:

[Structures showing various aryl and heteroaryl ring systems with R⁴⁰, R⁴¹, R⁴², R⁴³ substituents: benzene, pyridines, pyridazine, pyrazine, pyrimidine, triazine, piperidine, imidazole, thiophene, triazoles, tetrazole]

where,
R$^{40}$ and R$^{41}$ are, independently of one another, each a hydrogen atom or an alkyl, cycloalkyl, heterocycloalkyl, halo, aryl, imidazolylalkyl, indolylalkyl, heteroaryl, arylalkyl, arylalkoxy, heteroarylalkyl, heteroarylalkoxy, aminoalkyl, haloalkyl, mono-, di- or trihaloalkyl, mono-, di- or trihaloalkoxy, nitro, cyano, alkoxy, hydroxy, amino, phosphino, phosphate, alkylamino, dialkylamino, formyl, alkylthio, trialkylsilyl, alkylsulfonyl, arylsulfonyl, alkylsulfinyl, aminoalkyl, alkylaminoalkyl, dialkylaminoalkyl, hydroxyalkyl, morpholino, thioalkyl, alkylthioalkyl, carboxyalkyl, oximino, —COOR$^{50}$, —COR$^{50}$, —SO$_{0-2}$R$^{50}$, —SO$_2$NR$^{50}$R$^{51}$, —NR$^{52}$SO$_2$R$^{50}$, —CON(R$^{50}$R$^{51}$), —OCON(R$^{50}$R$^{51}$), —N(R$^{52}$)CO(R$^{50}$), —N(R$^{52}$)COOR$^{50}$, —N(R$^{52}$)CON(R$^{50}$R$^{51}$) or —OCONR$^{50}$ group, where, R$^{50}$, R$^{51}$ and R$^{52}$ are defined the same as above;
R$^{42}$ is a hydrogen atom or an alkyl, alkenyl, arylalkyl or acyl group; and
R$^{43}$ is a hydrogen atom or an alkyl or aryl group;
where, R$^{40}$ through R$^{43}$ and R$^{50}$ through R$^{52}$ are, independently of one another, each optionally substituted with any one of the groups defined above for the one or more substituents.

27. A pharmaceutical composition comprising a compound, enantiomer, stereoisomer, rotomer or tautomer of claim 1 or pharmaceutically acceptable salt thereof and a pharmaceutically acceptable carrier.

28. A method for treating a physiological disorder, symptom or disease in a patient, comprising administering to the patient an effective amount of the compound according to claim 1, wherein the physiological disorder, symptom or disease is urogenital, cardiovascular, cerebrovascular, peripheral vascular, angina pectoris, hypertension, restenosis post angioplasty, endarterectomy, stent introduction, cerebral stroke, respiratory tract, allergic associated with atopy, pulmonary hypertension, ischemic heart, impaired glucose tolerance, diabetes and its related complications, insulin resistance syndrome, hyperglycemia, polycystic ovarian syndrome, glomerular, renal insufficiency, nephritis, tubular interstitial, autoimmune, glaucoma, intestinal motility, cachexia or cancer.

29. The method according to claim 28, wherein the physiological disorder is a urogenital disorder.

30. The method according to claim 29, wherein the urogenital disorder is an erectile dysfunction.

31. A method for elevating a cGMP level in a patient in need of the treatment, comprising administering to the patient an effective amount of the compound according to claim 1.

32. A method for treating an erectile dysfunction in a patient in need of the treatment, comprising administering to the patient an effective amount of at least one of the compound according to claim 1.

33. A method for treating an erectile dysfunction in a patient in need of the treatment, comprising administering to the patient an effective amount of at least one of the compound according to claim 22.

34. A method for treating an erectile dysfunction or another symptom, disease or disorder in a patient in need of the treatment, comprising administering to the patient a combination therapy, comprising a therapeutically effective amount of at least one compound according to claim 1 and at least one compound selected from the group consisting of: a prostanoid, α-adrenergic receptor, dopamine receptor agonist, melanocortin receptor agonist, endothelin receptor antagonist, endothelin converting enzyme inhibitor, angiotensin II receptor antagonist, angiotensin converting enzyme inhibitor, neutral metalloendopeptidase inhibitor, renin inhibitor, serotonin 5-HT$_{2c}$ receptor agonist, nociceptin receptor agonist, rho kinase inhibitor, potassium channel modulator and multidrug resistance protein 5 inhibitor.

* * * * *

UNITED STATES PATENT AND TRADEMARK OFFICE
CERTIFICATE OF CORRECTION

| | | |
|---|---|---|
| PATENT NO. | : 6,821,978 B2 | Page 1 of 2 |
| APPLICATION NO. | : 09/940760 | |
| DATED | : November 23, 2004 | |
| INVENTOR(S) | : Samuel Chackalamannil | |

It is certified that error appears in the above-identified patent and that said Letters Patent is hereby corrected as shown below:

On the face of the patent, at item (74) Attorney, Agent or Firm, please replace "Gerald E. Reinhardt" with -- Gerard E. Reinhardt --.

In Column 97, Claim 1, line 18, please replace "-(R23)(R24)N(H)-" with -- -C(R23)(R24)N(H)- --.

In Column 97, Claim 1, line 62, please delete "with or without".

In Column 98, Claim 1, line 8, please replace "-SO2R5O" with -- -SO0-2R50 --.

In Column 98, Claim 1, line 25, please replace,

" 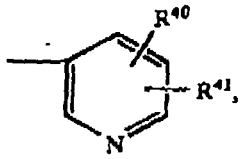 "

with

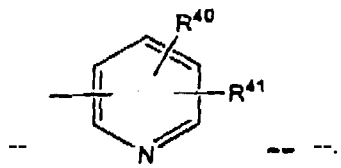

-- --.

In Column 100, Claim 10, line 3, please delete "or pharmaceutical composition".

In Column 100, Claim 10, lines 4-5, please replace "R4 is a cyclohexyl, hydroxy-cyclopentyl or tetrahydropyranyl group" with -- R4 is a cyclohexyl or hydroxy-cyclopentyl group --.

In Column 100, Claim 11, line 7, please delete "or pharmaceutical composition".

In Column 100, Claim 11, lines 12-13, please replace "R4 is a cyclohexyl, tetrahydropyranyl group or 2(R)-hydroxy-1(R)-cyclopentyl group" with -- R4 is a cyclohexyl or 2(R)-hydroxy-1(R)-cyclopentyl group --.

In Column 103, Claim 22, line 57, please replace "R1-4" with -- R14 --.

UNITED STATES PATENT AND TRADEMARK OFFICE
CERTIFICATE OF CORRECTION

PATENT NO.      : 6,821,978 B2                                               Page 2 of 2
APPLICATION NO. : 09/940760
DATED           : November 23, 2004
INVENTOR(S)     : Samuel Chackalamannil It is certified that error appears in the above-identified patent and that said Letters Patent is hereby corrected as shown below:

In Column 104, Claim 26, lines 46-49, please delete "with or without".

In Column 104, Claim 26, line 50, please replace "C3-5 " with -- C3-15 --.

In Column 104, Claim 26, line 60, please delete "with or without".

In Column 106, Claim 26, line 3, please replace "a -CH2)q group" with -- a -(CH 2)q group- --.

In Column 106, Claim 26, line 61, please delete "with or without".

In Column 107, Claim 26, line 40, please replace
" 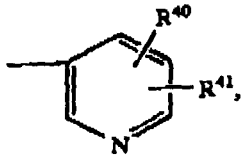 " with

-- 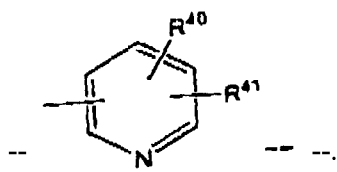 -- --.

Signed and Sealed this

Seventeenth Day of October, 2006

JON W. DUDAS
*Director of the United States Patent and Trademark Office*